(12) United States Patent
Andreini et al.

(10) Patent No.: US 8,188,079 B2
(45) Date of Patent: May 29, 2012

(54) 3-AMINO-5-PHENYL-5,6-DIHYDRO-2H-[1,4]OXAZINES

(75) Inventors: Matteo Andreini, Siena (IT); David Banner, Basel (CH); Wolfgang Guba, Muellheim (DE); Hans Hilpert, Muenchenstein (CH); Harald Mauser, Birsfelden (CH); Alexander V. Mayweg, Basel (CH); Robert Narquizian, Saint Louis (FR); Eoin Power, Siena (IT); Mark Rogers-Evans, Bottmingen (CH); Massimiliano Travagli, Siena (IT); Michela Valacchi, Siena (IT); Thomas Woltering, Freiburg (DE); Wolfgang Wostl, Grenzach-Wyhlen (DE)

(73) Assignees: Hoffman-La Roche Inc., Nutley, NJ (US); Siena Biotech S.p.A., Siena (IT)

( * ) Notice: Subject to any disclaimer, the term of this patent is extended or adjusted under 35 U.S.C. 154(b) by 0 days.

(21) Appl. No.: 12/852,538

(22) Filed: Aug. 9, 2010

(65) Prior Publication Data
US 2011/0046122 A1 Feb. 24, 2011

(30) Foreign Application Priority Data
Aug. 19, 2009 (EP) .................................... 09168132

(51) Int. Cl.
*A61K 31/535* (2006.01)
*C07D 413/12* (2006.01)
(52) U.S. Cl. ..................................... 514/235.5; 544/131
(58) Field of Classification Search .................. 544/131; 514/235.5
See application file for complete search history.

(56) References Cited

U.S. PATENT DOCUMENTS

| 5,691,336 A | 11/1997 | Dorn |
| 2007/0225267 A1 | 9/2007 | Broughton |
| 2011/0021520 A1* | 1/2011 | Badiger et al. ............. 514/233.2 |

OTHER PUBLICATIONS

Patani et al., "Bioisosterism: A Rational Approach in Drug Design" Chemical Reviews, 1996, vol. 96, pp. 3147-3176.*
Hardy et al., Science (2002) vol. 297 pp. 353-356.
Selkoe, Annu. Rev. Cell Biol. (1994) vol. 10 pp. 373-403.
Vassar et al., Bace, Science (1999) vol. 286 p. 735.
Luo et al., Nat Neurosci. (2001) vol. 4(3) pp. 231-232.
Roberds et al., Hum. Mol. Genet. (2001) vol. 10 (12) pp. 1317-1324.
McConlogue et al., J. Biol. Chem. (2007) vol. 282 p. 26326.
Prentki et al., J. Clin. Investig. (2006) vol. 116(7) pp. 1802-1812.
Wild et al., Diabetes Care (2004) vol. 27 pp. 1047-1053.
Zimmet et al., Nature (2001) vol. 414 pp. 782-787.
Baggio et al., Annu. Rev. Med. (2006) vol. 57 pp. 265-281.
Akpinar et al., Cell Metab. (2005) vol. 2 pp. 385-397.
Fukui et al., Cell Metab. (2005) vol. 2 pp. 373-384.
Finzi et al., Ultrastruct. Pathol. (2008) vol. 32 pp. 246-251.
Hussain et al., Mol. Cell Neurosci. (2000) vol. 16 pp. 609-619.
Kuhn et al., J. Biol. Chem. (2007) vol. 282 pp. 11982-11995.
Vattemi et al., Lancet (2001) vol. 358 pp. 1962-1964.
Barbiero et al., Exp. Neurol. (2003) vol. 182 pp. 335-345.
Sugimoto et al., J. Biol. Chem. (2007) vol. 282 pp. 34896-34903.
Desnues et al., Clin. Vaccine Immunol. (2006) vol. 13 pp. 170-178.
Gatchel et al., Proc. Natl. Acad. Sci. USA (2008) vol. 105 pp. 1291-1296.
Greenberg et al., Ann. Neurol. (2005) vol. 57 pp. 664-678.
Lagos et al., Blood (2007) vol. 109 pp. 1550-1558.
Koistinen et al., Muscle Nerve (2006) vol. 34 pp. 444-450.
Li et al., Aging Cell (2006) vol. 5 pp. 153-165.
Kim et al., Neurobiol. Dis. (2006) vol. 22 pp. 346-356.
Hodges et al., Hum. Mol. Genet (2006) vol. 15 pp. 965-977.
Kihara et al., Proc. Natl. Acad. Sci. USA (2009) vol. 106 pp. 21807-21812.
Talantov et al., Clin. Cancer Res. (2005) vol. 11 pp. 7234-7242.
Basset et al., Scand. J. Immunol. (2000) vol. 51 pp. 307-311.
Grewal et al., Mol. Cell Biol. (2006) vol. 26 pp. 4970-4981.
Hedlund et al., Cancer Research (2008) vol. 68(2) pp. 388-394.
Kondoh et al., Breast Cancer Research Treatment (2003) vol. 78(1) pp. 37-44.
Hoffmeister et al., JOP (2009) vol. 10(5) pp. 501-506.
Woodard-Grice et al., J. Biol. Chem. (2008) vol. 283 pp. 26364-26373.
Toegel et al., Osteoarthritis Cartilage (2010) vol. 18 pp. 240-248.
Lichtenthaler et al., J. Biol. Chem. (2003) vol. 278 pp. 48713-48719.
Merten et al., (2004) vol. 93 pp. 855-863.
Maugeri t al., Srp. Arch. Celok Iek (2010) Suppl. 1 pp. 50-52.
Kilijanski et al., Thyroid (2005) vol. 15 pp. 645-652.
International Search Report dated Oct. 29, 2010.

* cited by examiner

*Primary Examiner* — Rebecca Anderson
(74) *Attorney, Agent, or Firm* — George W. Johnston; Patricia S. Rocha-Tramaloni; Kimberly J. Prior

(57) ABSTRACT

The present invention relates to 3-Amino-5-phenyl-5,6-dihydro-2H-[1,4]oxazines of formula I

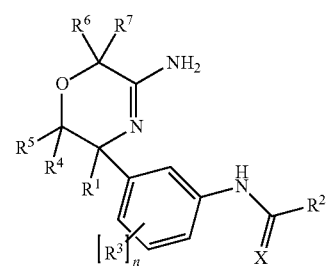

having BACE1 and/or BACE2 inhibitory activity, their manufacture, pharmaceutical compositions containing them and their use as therapeutically active substances. The active compounds of the present invention are useful in the therapeutic and/or prophylactic treatment of e.g. Alzheimer's disease and type 2 diabetes.

19 Claims, No Drawings

3-AMINO-5-PHENYL-5,6-DIHYDRO-2H-[1,4]OXAZINES

PRIORITY TO RELATED APPLICATION(S)

This application claims the benefit of European Patent Application No. 09168132.0, filed Aug. 19, 2009, which is hereby incorporated by reference in its entirety.

TECHNICAL FIELD

The present invention is concerned with 3-Amino-5-phenyl-5,6-dihydro-2H-[1,4]oxazines having BACE1 and/or BACE2 inhibitory properties, their manufacture, pharmaceutical compositions containing them and their use as therapeutically active substances.

BACKGROUND OF THE INVENTION

Alzheimer's disease (AD) is a neurodegenerative disorder of the central nervous system and the leading cause of a progressive dementia in the elderly population. Its clinical symptoms are impairment of memory, cognition, temporal and local orientation, judgment and reasoning but also severe emotional disturbances. There are currently no treatments available which can prevent the disease or its progression or stably reverse its clinical symptoms. AD has become a major health problem in all societies with high life expectancies and also a significant economic burden for their health systems.

AD is characterized by 2 major pathologies in the central nervous system (CNS), the occurrence of amyloid plaques and neurofibrillar tangles (Hardy et al., The amyloid hypothesis of Alzheimer's disease: progress and problems on the road to therapeutics, *Science*. 2002 Jul. 19; 297(5580):353-6, Selkoe, Cell biology of the amyloid β-protein precursor and the mechanism of Alzheimer's disease, *Annu Rev Cell Biol.* 1994; 10:373-403). Both pathologies are also commonly observed in patients with Down's syndrome (trisomy 21), which also develop AD-like symptoms in early life. Neurofibrillar tangles are intracellular aggregates of the microtubule-associated protein tau (MAPT). Amyloid plaques occur in the extracellular space; their principal components are Aβ-peptides. The latter are a group of proteolytic fragments derived from the β-amyloid precursor protein (APP) by a series of proteolytic cleavage steps. Several forms of APP have been identified of which the most abundant are proteins of 695, 751 and 770 amino acids length. They all arise from a single gene through differential splicing. The Aβ-peptides are derived from the same domain of the APP but differ at their N- and C-termini, the main species are of 40 and 42 amino-acid length. There are several lines of evidence which strongly suggest that aggregated Aβ-peptides are the essential molecules in the pathogenesis of AD: 1) amyloid plaques formed of Aβ-peptides are invariably part of the AD pathology; 2) Aβ-peptides are toxic for neurons; 3) in Familial Alzheimer's Disease (FAD) the mutations in the disease genes APP, PSN1, PSN2 lead to increased levels of Aβ-peptides and early brain amyloidosis; 4) transgenic mice which express such FAD genes develop a pathology which bears many resemblances to the human disease. Aβ-peptides are produced from APP through the sequential action of 2 proteolytic enzymes termed β- and γ-secretase. β-Secretase cleaves first in the extracellular domain of APP approximately 28 amino acids outside of the trans-membrane domain (TM) to produce a C-terminal fragment of APP containing the TM- and the cytoplasmatic domain (CTFβ). CTFβ is the substrate for γ-secretase which cleaves at several adjacent positions within the TM to produce the Aβ peptides and the cytoplasmic fragment. The γ-secretase is a complex of at least 4 different proteins, its catalytic subunit is very likely a presenilin protein (PSEN1, PSEN2). The β-secretase (BACE1, Asp2; BACE stands for β-site APP-cleaving enzyme) is an aspartyl protease which is anchored into the membrane by a transmembrane domain (Vassar et al., Beta-secretase cleavage of Alzheimer's amyloid precursor protein by the transmembrane aspartic protease BACE, *Science*. 1999 Oct. 22; 286(5440):735). It is expressed in many tissues of the human organism but its level is especially high in the CNS. Genetic ablation of the BACE1 gene in mice has clearly shown that its activity is essential for the processing of APP which leads to the generation of Aβ-peptides, in the absence of BACE1 no Aβ-peptides are produced (Luo et al., Mice deficient in BACE1, the Alzheimer's beta-secretase, have normal phenotype and abolished beta-amyloid generation, *Nat. Neurosci.* 2001 March; 4(3):231-2, Roberds et al., BACE knockout mice are healthy despite lacking the primary beta-secretase activity in brain: implications for Alzheimer's disease therapeutics, *Hum Mol. Genet.* 2001 Jun. 1; 10(12): 1317-24). Mice which have been genetically engineered to express the human APP gene and which form extensive amyloid plaques and Alzheimer's disease like pathologies during aging fail to do so when β-secretase activity is reduced by genetic ablation of one of the BACE1 alleles (McConlogue et al., Partial reduction of BACE1 has dramatic effects on Alzheimer plaque and synaptic pathology in APP Transgenic Mice. *J Biol Chem.* 2007 Sep. 7; 282(36):26326). It is thus presumed that inhibitors of BACE1 activity can be useful agents for therapeutic intervention in AD.

Type 2 diabetes (T2D) is caused by insulin resistance and inadequate insulin secretion from pancreatic β-cells leading to poor blood-glucose control and hyperglycemia (M Prentki & CJ Nolan, "Islet beta-cell failure in type 2 diabetes." J. Clin. Investig. 2006, 116(7), 1802-1812). Patients with T2D have an increased risk of microvascular and macrovascular disease and a range of related complications including diabetic nephropathy, retinopathy and cardiovascular disease. In 2000, an estimated 171 million people had the condition with the expectation that this figure will double by 2030 (S Wild, G Roglic, A Green, R. Sicree & H King, "Global prevalence of diabetes", Diabetes Care 2004, 27(5), 1047-1053), making the disease a major healthcare problem. The rise in prevalence of T2D is associated with an increasingly sedentary lifestyle and high-energy food intake of the world's population (P Zimmet, KGMM Alberti & J Shaw, "Global and societal implications of the diabetes epidemic" Nature 2001, 414, 782-787).

β-Cell failure and consequent dramatic decline in insulin secretion and hyperglycemia marks the onset of T2D. Most current treatments do not prevent the loss of β-cell mass characterizing overt T2D. However, recent developments with GLP-1 analogues, gastrin and other agents show that preservation and proliferation of β-cells is possible to achieve, leading to an improved glucose tolerance and slower progression to overt T2D (L L Baggio & D J Drucker, "Therapeutic approaches to preserve islet mass in type 2 diabetes", Annu Rev. Med. 2006, 57, 265-281).

Tmem27 has been identified as a protein promoting beta-cell proliferation (P Akpinar, S Kuwajima, J Krützfeldt, M Stoffel, "Tmem27: A cleaved and shed plasma membrane protein that stimulates pancreatic β cell proliferation", Cell Metab. 2005, 2, 385-397) and insulin secretion (K Fukui, Q Yang, Y Cao, N Takahashi et al., "The HNF-1 target Collectrin controls insulin exocytosis by SNARE complex formation", Cell Metab. 2005, 2, 373-384). Tmem27 is a 42 kDa membrane glycoprotein which is constitutively shed from the surface of β-cells, resulting from a degradation of the full-length cellular Tmem27. Overexpression of Tmem27 in a transgenic mouse increases β-cell mass and improves glucose tolerance in a diet-induced obesity (DIO) model of diabetes. Furthermore, siRNA knockout of Tmem27 in a rodent β-cell proliferation assay (e.g. using INS1e cells) reduces the proliferation rate, indicating a role for Tmem27 in control of β-cell mass.

In the same proliferation assay, BACE2 inhibitors also increase proliferation. However, BACE2 inhibition combined with Tmem27 siRNA knockdown results in low proliferation rates. Therefore, it is concluded that BACE2 is the protease responsible for the degradation of Tmem27. Furthermore, in vitro, BACE2 cleaves a peptide based on the sequence of Tmem27. The closely related protease BACE1 does not cleave this peptide and selective inhibition of BACE1 alone does not enhance proliferation of β-cells.

The close homolog BACE2 is a membrane-bound aspartyl protease and is co-localized with Tmem27 in human pancreatic β-cells (G Finzi, F Franzi, C Placidi, F Acquati et al., "BACE2 is stored in secretory granules of mouse and rat pancreatic beta cells", Ultrastruct Pathol. 2008, 32(6), 246-251). It is also known to be capable of degrading APP (1Hussain, D Powell, D Howlett, G Chapman et al., "ASP1 (BACE2) cleaves the amyloid precursor protein at the β-secretase site" Mol Cell Neurosci. 2000, 16, 609-619), IL-1R2 (P Kuhn, E Marjaux, A Imhof, B De Strooper et al., "Regulated intramembrane proteolysis of the interleukin-1 receptor II by alpha-, beta-, and gamma-secretase" J. Biol. Chem. 2007, 282(16), 11982-11995) and ACE2. The capability to degrade ACE2 indicates a possible role of BACE2 in the control of hypertension.

Inhibition of BACE2 is therefore proposed as a treatment for T2D with the potential to preserve and restore β-cell mass and stimulate insulin secretion in pre-diabetic and diabetic patients. It is therefore an object of the present invention to provide selective BACE2 inhibitors. Such compounds are useful as therapeutically active substances, particularly in the treatment and/or prevention of diseases which are associated with the inhibition of BACE2.

Furthermore, the formation, or formation and deposition, of β-amyloid peptides in, on or around neurological tissue (e.g., the brain) are inhibited by the present compounds, i.e. inhibition of the Aβ-production from APP or an APP fragment.

Inhibitors of BACE1 and/or BACE2 can in addition be used to treat the following diseases:
IBM (inclusion body myositis) (Vattemi G. et al., Lancet. 2001 Dec. 8; 358(9297):1962-4), Down's Syndrome (Barbiero L. et al, Exp Neurol. 2003 August; 182(2):335-45), Wilson's Disease (Sugimoto I. et al., J Biol Chem. 2007 Nov. 30; 282(48):34896-903), Whipple's disease (Desnues B. et al., Clin Vaccine Immunol. 2006 February; 13(2):170-8), SpinoCerebellar Ataxia 1 and SpinoCerebellar Ataxia 7 (Gatchel J. R. et al., *Proc Natl Acad Sci USA* 2008 Jan. 29; 105(4):1291-6), Dermatomyositis (Greenberg S. A. et al., Ann Neurol. 2005 May; 57(5):664-78 and Greenberg S. A. et al., *Neurol* 2005 May; 57(5):664-78), Kaposi Sarcoma (Lagos D. et al, Blood, 2007 Feb. 15; 109(4):1550-8), Glioblastoma multiforme (E-MEXP-2576, http://www.ebi.ac.uk/microarray-as/aer/result?queryFor=PhysicalArrayDesign&aAccession=A-MEXP-258), Rheumatoid arthritis (Ungethuem U. et al, GSE2053), Amyotrophic lateral sclerosis (Koistinen H. et al., Muscle Nerve. 2006 October; 34(4):444-50 and Li Q. X. et al, Aging Cell. 2006 April; 5(2):153-65), Huntington's Disease (Kim Y. J. et al., Neurobiol Dis. 2006 May; 22(2):346-56. Epub 2006 Jan. 19 and Hodges A. et al., Hum Mol Genet. 2006 Mar. 15; 15(6):965-77. Epub 2006 Feb. 8), Multiple Mieloma (Kihara Y. et al, Proc Natl Acad Sci USA. 2009 Dec. 22; 106(51):21807-12), Malignant melanoma (Talantov D. et al, Clin Cancer Res. 2005 Oct. 15; 11(20):7234-42), Sjogren syndrome (Basset C. et al., Scand J Immunol. 2000 March; 51(3):307-11), Lupus erythematosus (Grewal P. K. et al, Mol Cell Biol. 2006, July; 26(13):4970-81), Macrophagic myofasciitis, juvenile idiopathic arthritis, granulomatous arthritis, Breast cancer (Hedlund M. et al, Cancer Res. 2008 Jan. 15; 68(2):388-94 and Kondoh K. et al., Breast Cancer Res Treat. 2003 March; 78(1):37-44), Gastrointestinal diseases (Hoffmeister A. et al, JOP. 2009 Sep. 4; 10(5):501-6), Autoimmune/inflammatory diseases (Woodard-Grice A. V. et al., J Biol Chem. 2008 Sep. 26; 283(39):26364-73. Epub 2008 Jul. 23), Rheumatoid Arthritis (Toegel S. et al, Osteoarthritis Cartilage. 2010 February; 18(2):240-8. Epub 2009 Sep. 22), Inflammatory reactions (Lichtenthaler S. F. et al., J Biol Chem. 2003 Dec. 5; 278(49):48713-9. Epub 2003 Sep. 24), Arterial Thrombosis (Merten M. et al., Z Kardiol. 2004 November; 93(11):855-63), Cardiovascular diseases such as Myocardial infarction and stroke (Maugeri N. et al., Srp Arh Celok Lek. 2010 January; 138 Suppl 1:50-2) and Graves disease (Kiljański J. et al, Thyroid. 2005 July; 15(7):645-52).

SUMMARY OF THE INVENTION

The present invention provides compounds of formula I,

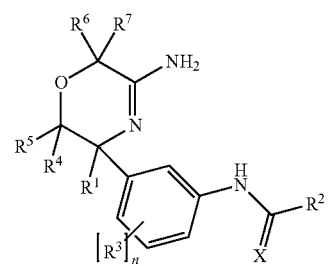

wherein the substituents and variables are as described below, and pharmaceutically acceptable salts thereof.

The present invention also provides pharmaceutical compositions containing a compound of formula I or a pharmaceutically acceptable salt thereof. The invention also provides methods for the manufacture of the compounds and compositions of the invention. Further, the invention provides methods for the control or prevention of illnesses such as Alzheimer's disease and type 2 diabetes. Furthermore, the formation, or formation and deposition, of β-amyloid plaques in, on or around neurological tissue (e.g., the brain) are inhibited by the present compounds by inhibiting the Aβ production from APP or an APP fragment.

The present compounds have Asp2 (β-secretase, BACE1 or Memapsin-2) inhibitory activity and can therefore be used in the therapeutic and/or prophylactic treatment of diseases and disorders that exhibit elevated β-amyloid levels and/or β-amyloid oligomers and/or β-amyloid plaques and further deposits, particularly Alzheimer's disease. The present compounds have BACE2 inhibitory activity and can therefore be used in the therapeutic and/or prophylactic treatment of diseases and disorders such as type 2 diabetes and other metabolic disorders.

Furthermore the use of compounds of formula I in the treatment of amyotrophic lateral sclerosis (ALS), arterial thrombosis, autoimmune/inflammatory diseases, cancer such as breast cancer, cardiovascular diseases such as myocardial infarction and stroke, dermatomyositis, Down's Syndrome, gastrointestinal diseases, Glioblastoma multiforme, Graves Disease, Huntington's Disease, inclusion body myositis (IBM), inflammatory reactions, Kaposi Sarcoma, Kostmann Disease, lupus erythematosus, macrophagic myofasciitis, juvenile idiopathic arthritis, granulomatous arthritis, malignant melanoma, multiple mieloma, rheumatoid arthritis, Sjogren syndrome, SpinoCerebellar Ataxia 1, SpinoCerebellar Ataxia 7, Whipple's Disease and Wilson's Disease.

DETAILED DESCRIPTION OF THE INVENTION

The present invention provides a compound of formula I and pharmaceutically acceptable salts thereof, the preparation of such compounds, medicaments, i.e. pharmaceutical compositions, containing them and their manufacture. The invention also provides methods for the therapeutic and/or prophylactic treatment of diseases and disorders that are associated by inhibition of BACE1 and/or BACE2 activity, such as Alzheimer's disease and type 2 diabetes, by administering a compound of the invention. The invention also provides methods for the therapeutic and/or prophylactic treatment of diseases such as amyotrophic lateral sclerosis (ALS), arterial thrombosis, autoimmune/inflammatory diseases, cancer such as breast cancer, cardiovascular diseases such as myocardial infarction and stroke, dermatomyositis, Down's Syndrome, gastrointestinal diseases, Glioblastoma multiforme, Graves Disease, Huntington's Disease, inclusion body myositis (IBM), inflammatory reactions, Kaposi Sarcoma, Kostmann Disease, lupus erythematosus, macrophagic myofasciitis, juvenile idiopathic arthritis, granulomatous arthritis, malignant melanoma, multiple mieloma, rheumatoid arthritis, Sjogren syndrome, SpinoCerebellar Ataxia 1, SpinoCerebellar Ataxia 7, Whipple's Disease and Wilson's Disease.

The following definitions of the general terms used in the present description apply irrespectively of whether the terms in question appear alone or in combination with other groups.

The term "lower alkyl", alone or in combination with other groups, stands for a hydrocarbon radical which can be linear or branched, with single or multiple branching, whereby the alkyl group in general comprises 1 to 6 carbon atoms, for example, methyl (Me), ethyl (Et), propyl, isopropyl (i-propyl), n-butyl, i-butyl (iso-butyl), 2-butyl (sec-butyl), t-butyl (tent-butyl) and the like. Preferred alkyl groups are groups with 1 to 4 carbon atoms, for example methyl, ethyl and isopropyl. Most preferred is methyl.

The phrase "lower alkyl substituted by", alone or in combination with other groups, refers to lower alkyl as defined above, which is substituted by one or multiple substituents, preferably 1-5 substituents, individually selected from the group of substituents consisting of acetamidyl, acetyl, amido, amino, carboxy, cyano, cycloalkyl, halogen, halogen-lower alkoxy, heterocyclyl, hydroxy, (lower alkyl,H)N—, (lower alkyl,lower alkyl)N—, lower alkyl-S(O)$_2$—, lower alkoxy, nitro and the like. Preferred "lower alkyl substituted by" are lower alkyl substituted by 1-5 substituents individually selected from cycloalkyl, halogen, halogen-lower alkoxy and lower alkoxy. More preferred are trifluoro-lower alkyl, halogen-methyl and halogen-ethyl. More preferred are trifluoro-methyl, trifluoro-ethyl and pentafluoro-ethyl. Most preferred are methoxy-methyl, 3,3,3-trifluoro-1-(tetrahydro-furan-2-yl-propyl, 1,1,2,2,2-pentafluoro-ethyl, 1,1,2,2-tetrafluoro-ethyl, 1,1,1,2-tetrafluoro-ethyl, 2,2,2-trifluoroethyl, 2,2-difluoro-ethyl, 2-fluoro-ethyl, difluoro-methyl and fluoro-isopropyl.

The term "halogen-lower alkyl", alone or in combination with other groups, refers to lower alkyl, which is substituted by one or multiple halogens. Preferred are trifluoro-lower alkyl, halogen-methyl and halogen-ethyl. More preferred "halogen-lower alkyl" is trifluoro-methyl, trifluoro-ethyl and pentafluoro-ethyl. Most preferred are 1,1,2,2,2-pentafluoro-ethyl, 1,1,2,2-tetrafluoro-ethyl, 1,1,1,2-tetrafluoro-ethyl, 2,2,2-trifluoroethyl, 2,2-difluoro-ethyl, 2-fluoro-ethyl, difluoro-methyl and fluoro-isopropyl.

The term "lower alkoxy-lower alkyl", alone or in combination with other groups, refers to lower alkyl, which is substituted by one or multiple lower alkoxy as defined herewithin. Examples are MeO-Me (methoxy-methyl, H$_3$C—O—CH$_2$—), 1MeO-Et, 2MeO-Et, 1MeO-2EtO-propyl and the like. Preferred is MeO-Me.

The term "cyano-lower alkyl", alone or in combination with other groups, refers to lower alkyl, which is substituted by one or multiple cyano as defined herewithin. Examples are NC-Me (cyano-methyl, H$_3$C—O—CH$_2$—, 1NC-Et, 2NC-propyl, and the like.

The term "cyano", alone or in combination with other groups, refers to N≡C— (NC—).

The term "halogen", alone or in combination with other groups, denotes chloro (Cl), iodo (I), fluoro (F) and bromo (Br). Preferred "halogen" is chloro and fluoro. Most preferred is fluoro.

The term "aryl", alone or in combination with other groups, refers to an aromatic carbocyclic group comprising 6 to 14, preferably 6 to 10, carbon atoms and having at least one aromatic ring or multiple condensed rings in which at least one ring is aromatic. Examples of "aryl" include benzyl, biphenyl, indanyl, naphthyl, phenyl (Ph) and the like. Preferred "aryl" are phenyl and benzyl. Most preferred is phenyl.

The phrase "aryl substituted by", alone or in combination with other groups, refers to an aryl group which is substituted by one or multiple substituents, preferably 1-4 substituents, whereby substitution at each ring atom individually substituted with a substituent individually selected from the group consisting of amino, amino-lower alkyl, carboxy, carboxy-lower alkyl, lower alkyl-N(lower alkyl)-CO—, NH$_2$—CO—, lower alkyl-NH—CO—, cyano, cyano-lower alkyl, halogen, halogen-lower alkoxy, halogen-lower alkyl, hydroxy, hydroxy-lower alkyl, lower alkoxy, lower alkoxy-lower alkyl, lower alkyl, lower alkyl-CO—, lower alkyl-COO-lower alkyl, (lower alkyl,H)N—, (lower alkyl,lower alkyl)N—, lower alkyl-S(O)$_2$—, N(lower alkyl,H)-lower alkyl, N(lower alkyl,lower alkyl)-lower alkyl, nitro and the like. Preferred "aryl substituted by" are aryl substituted by 1-4 substituents individually selected from cyano, cyano-lower alkyl, halogen, halogen-lower alkoxy, halogen-lower alkyl, lower alkoxy, lower alkoxy-lower alkyl and lower alkyl. More preferred are halogens, most preferred are F, Cl and I. Also preferred are halogen-aryl, halogen-phenyl, fluoro-phenyl, fluoro-aryl, chloro-phenyl, chloro-aryl, fluoro-chloro-aryl and fluoro-chloro-phenyl, iodo-chloro-aryl and iodo-chloro-phenyl. Most preferred are 2,4-dichloro-phenyl, 2,5-difluoro-phenyl, 3-chloro-phenyl, 4-chloro-2-fluoro-phenyl, 4-chloro-2-iodo-phenyl, 4-chloro-phenyl, 4-cyano-2-fluoro-phenyl and 4-oxazol-5-yl-phenyl.

The term "heteroaryl", alone or in combination with other groups, refers to an aromatic carbocyclic group of having a single 5 to 8 membered ring or multiple condensed rings comprising 6 to 14, more preferably 6 to 10, ring atoms and containing 1, 2 or 3 heteroatoms, in which group at least one heterocyclic ring is aromatic and the heteroatoms are individually selected from O, S and N. Examples of "heteroaryl" include benzofuryl, benzoimidazolyl, benzooxazinyl, benzothiazinyl, benzothiazolyl, benzothienyl, benzotriazolyl, furyl, imidazolyl, indazolyl, indolyl, isoquinolinyl, isothiazolyl, isoxazolyl, oxazolyl, pyrazinyl, pyrazolyl (pyrazyl), pyrazolo[1,5-a]pyridinyl, pyridazinyl, pyridinyl, pyrimidinyl, pyrrolyl, quinolinyl, tetrazolyl, thiazolyl, thienyl, triazolyl and the like. Preferred heteroaryls are furyl, indazolyl, oxazolyl, pyrazinyl, pyrazolo[1,5-a]pyridinyl, pyrazolyl, pyridinyl, thiazolyl and thienyl. Most preferred are 1H-indazol-3-yl, 1H-pyrazol-3-yl, fur-3-yl, isoxazol-3-yl, oxazol-2-yl, oxazol-4-yl, pyrazin-2-yl, pyrazolo[1,5-a]pyridin-2-yl, pyridin-2-yl, pyrimidin-2-yl, pyrimidin-4-yl, thiazol-4-yl, thiazol-5-yl, thien-2-yl, thien-3-yl and thiophen-2-yl.

The phrase "heteroaryl substituted by", alone or in combination with other groups, refers to a heteroaryl which is substituted by one or multiple substituents, preferably 1-4 substituents, whereby substitution at each ring atom individually is selected from the group consisting of amino, amino-lower alkyl, carboxy, carboxy-lower alkyl, lower alkyl-N(lower alkyl)-CO—, $NH_2$—CO—, lower alkyl-NH—CO—, cyano, cyano-lower alkyl, halogen, halogen-lower alkoxy, halogen-lower alkyl, hydroxy, hydroxy-lower alkyl, lower alkoxy, lower alkoxy-lower alkyl, lower alkyl, lower alkyl-CO—, lower alkyl-COO-lower alkyl, (lower alkyl,H)N—, (lower alkyl, lower alkyl)N—, lower alkyl-S(O)$_2$—, N(lower alkyl,H)-lower alkyl, N(lower alkyl,lower alkyl)-lower alkyl, nitro and the like. Preferred substituents are halogen, lower alkyl, halogen-lower alkyl and halogen-lower alkoxy, most preferred are methyl, dimethyl, trifluoro-methyl, trifluoro-ethyl, trifluoro-ethoxy, chloro, dichloro and difluoro. Preferred "heteroaryl substituted by" are heteroaryl substituted by 1-4 substituents individually selected from cyano, cyano-lower alkyl, halogen, halogen-lower alkoxy, halogen-lower alkyl, lower alkoxy, lower alkoxy-lower alkyl and lower alkyl. More preferred are lower alkyl-heteroaryl, halogen-lower alkyl-heteroaryl, halogen-lower alkoxy-heteroaryl, halogen-pyridinyl, halogen-thienyl, lower alkyl-thienyl, lower alkyl-thiazolyl, lower alkyl-oxazolyl, lower alkyl-furyl, halogen-lower alkyl-pyrazolyl, lower alkyl-indazolyl, halogen-lower alkoxy-pyridinyl and halogen-halogen-lower alkyl-pyridinyl. Most preferred are 5-phenyl-oxazol-4-yl, 5-cyano-pyridin-2-yl, 5-chloro-pyridin-2-yl, 3,5-dichloro-pyridin-2-yl, 3,5-difluoro-pyridin-2-yl, 5-chloro-thien-2-yl, 5-chloro-pyrimidin-2-yl, 3-fluoro-pyridin-2-yl, 3-chloro-thiophen-2-yl, 5-chloro-3-fluoro-pyridin-2-yl, 5-fluoro-pyridin-2-yl, 5-(2,2,2-trifluoro-ethoxy)-pyridin-2-yl, 3-(2,2,2-trifluoro-ethoxy)-pyridin-2-yl, 5-(2-fluoro-ethoxy)-pyridin-2-yl, 5-(2,2-difluoro-ethoxy)-pyridin-2-yl, 5-difluoromethoxy-pyridin-2-yl, 1-(2,2,2-trifluoro-ethyl)-1H-pyrazol-3-yl, 5-trifluoromethyl-pyrazin-2-yl, 5-trifluoromethyl-pyrimidin-2-yl, 5-cyclopropylmethoxy-pyridin-2-yl, 5-but-3-enyloxy-pyridin-2-yl, 5-benzyloxy-pyridin-2-yl, 5-furan-2-yl-isoxazole-3-yl, 5-furan-2-yl-pyridin-2-yl, 5-thiophen-2-yl-isoxazole-3-yl, 5-pyrrolidin-1-yl-pyridin-2-yl, 2,5-dimethyl-fur-3-yl, 2,5-dimethyl-oxazol-4-yl, 2,5-dimethyl-thien-3-yl, 5-methyl-pyrazine-2-yl, 1-methyl-1H-indazol-3-yl, 2-methyl-oxazol-4-yl, 2-methyl-thiazol-4-yl, 5-butyl-pyridin-2-yl, 1,1-difluoromethyl-1H-pyrazol-3-yl, 3,5-difluoro-pyridin-2-yl, 3-chloro-5-trifluoromethyl-pyridin-2-yl, 4-chloro-1-methyl-1H-pyrazole-3-yl, 5-chloro-3-ethyl-pyridin-2-yl, 3-sec-butyl-5-chloro-pyridin-2-yl, 5-chloro-3-methyl-pyridin-2-yl, 3-chloro-5-cyano-pyridin-2-yl and 2-methyl-4-trifluoromethyl-thiazol-5-yl.

The term "cycloalkyl", alone or in combination with other groups, refers to a 3 to 6 membered carbon ring, for example cyclopropyl, cyclobutyl, cyclopentyl or cyclohexyl. Preferred cycloalkyl are cyclopropyl and cyclobutyl. Most preferred is cyclopropyl.

The phrase "cycloalkyl substituted by", alone or in combination with other groups, refers to a cycloalkyl group which is substituted by one or multiple substituents, preferably 1-4 substituents, whereby substitution at each ring atom individually is selected from the group consisting of amino, amino-lower alkyl, carboxy, carboxy-lower alkyl, lower alkyl-N(lower alkyl,H)—CO—, lower alkyl-N(lower alkyl,lower alkyl)-CO—, lower alkyl-$NH_2$—CO—, cyano, cyano-lower alkyl, halogen, halogen-lower alkoxy, halogen-lower alkyl, hydroxy, hydroxy-lower alkyl, lower alkoxy, lower alkoxy-lower alkyl, lower alkyl, lower alkyl-CO—, lower alkyl-COO-lower alkyl, (lower alkyl,H)N—, (lower alkyl,lower alkyl)N—, lower alkyl-S(O)$_2$—, N(lower alkyl,H)-lower alkyl, N(lower alkyl,lower alkyl)-lower alkyl, nitro and the like. Preferred "cycloalkyl substituted by" are cycloalkyl substituted by 1-4 substituents individually selected from cyano, cyano-lower alkyl, halogen, halogen-lower alkoxy, halogen-lower alkyl, lower alkoxy, lower alkoxy-lower alkyl and lower alkyl. Preferred are, lower alkoxy-lower alkyl, halogen and halogen-lower alkyl. Most preferred are 2,2-difluoro-cycloprop-1-yl, 3-chloro-cyclobut-1-yl, 3,3-difluoro-cyclobut-1-yl, 1-trifluoromethyl-cycloprop-1-yl and 1-methoxymethyl-cycloprop-1-yl.

The term "lower alkoxy", alone or in combination with other groups, stands for an —O-lower alkyl radical which can be linear or branched, with single or multiple branching, whereby the alkyl group in general comprises 1 to 6 carbon atoms, for example, methoxy (OMe, MeO), ethoxy (OEt), propoxy, isopropoxy (i-propoxy), n-butoxy, i-butoxy (iso-butoxy), 2-butoxy (sec-butoxy), t-butoxy (tert-butoxy), iso-pentyloxy (i-pentyloxy) and the like. Preferred "lower alkoxy" are groups with 1 to 4 carbon atoms. Most preferred are ethoxy and methoxy.

The term "halogen-lower alkoxy", alone or in combination with other groups, refers to lower alkoxy, which is substituted by one or multiple halogens. Preferred "halogen-lower alkoxy" are fluoro-lower alkoxy, fluoro-ethoxy and halogen-ethoxy.

The term "heterocyclyl", alone or in combination with other groups, refers to a 4 to 8 membered ring containing 1, 2 or 3 ring heteroatoms individually selected from N, O or S. 1 or 2 ring heteroatoms are preferred. Preferred are 4 to 6 membered "heterocyclyl", more preferred 5 to 6 membered "heterocyclyl", each containing 1 or 2 ring heteroatoms selected from N, O or S. Examples of "heterocyclyl" include azepanyl, azetidyl, diazepanyl, morpholinyl, oxazepanyl, oxazolidyl, oxetanyl, piperazinyl, piperidyl, pyrrolidinyl, tetrahydrofuryl, tetrahydropyridyl, tetrahydropyrryl, tetrahydrothienyl, thiazolidyl, thiomorpholinyl and the like. Preferred is tetrahydro-furan-3-yl.

The phrase "heterocyclyl substituted by", alone or in combination with other groups, refers to a heterocyclyl which is substituted by one or multiple substituents, preferably 1-4 substituents, whereby substitution at each ring atom individually is selected from the group consisting of amino, amino-lower alkyl, carboxy, carboxy-lower alkyl, lower alkyl-N(lower alkyl,H)—CO—, lower alkyl-N(lower alkyl,lower alkyl)-CO—, lower alkyl-$NH_2$—CO—, cyano, cyano-lower alkyl, halogen, halogen-lower alkoxy, halogen-lower alkyl, hydroxy, hydroxy-lower alkyl, lower alkoxy, lower alkoxy-lower alkyl, lower alkyl, lower alkyl-CO—, lower alkyl-COO-lower alkyl, (lower alkyl,H)N—, (lower alkyl,lower alkyl)N—, lower alkyl-S(O)$_2$—, N(lower alkyl,H)-lower alkyl, N(lower alkyl,lower alkyl)-lower alkyl, nitro and the like. Preferred "heterocyclyl substituted by" are heterocyclyl substituted by 1-4 substituents individually selected from cyano, cyano-lower alkyl, halogen, halogen-lower alkoxy, halogen-lower alkyl, lower alkoxy, lower alkoxy-lower alkyl and lower alkyl.

The term "pharmaceutically acceptable salts" refers to salts that are suitable for use in contact with the tissues of humans and animals. Examples of suitable salts with inorganic and organic acids are, but are not limited to acetic acid, citric acid, formic acid, fumaric acid, hydrochloric acid, lactic acid, maleic acid, malic acid, methane-sulfonic acid, nitric acid, phosphoric acid, p-toluenesulphonic acid, succinic acid, sulfuric acid, sulphuric acid, tartaric acid, trifluoroacetic acid and the like. Preferred are formic acid and hydrochloric acid. Most preferred is hydrochloric acid.

"Pharmaceutically acceptable," such as pharmaceutically acceptable carrier, excipient, etc., means pharmacologically acceptable and substantially non-toxic to the subject to which the particular compound is administered.

The terms "pharmaceutically acceptable carrier" and "pharmaceutically acceptable auxiliary substance" refer to carriers and auxiliary substances such as diluents or excipients that are compatible with the other ingredients of the formulation.

Substituents at a double bond or a ring can be present in cis (=Z—) or trans (=E-) form, unless the stereochemistry is explicitly depicted in the corresponding compound formula I.

The term "pharmaceutical composition" encompasses a product comprising specified ingredients in pre-determined amounts or proportions, as well as any product that results, directly or indirectly, from combining specified ingredients in specified amounts. Preferably it encompasses a product comprising one or more active ingredients, and an optional carrier comprising inert ingredients, as well as any product that results, directly or indirectly, from combination, complexation or aggregation of any two or more of the ingredients, or from dissociation of one or more of the ingredients, or from other types of reactions or interactions of one or more of the ingredients.

"Therapeutically effective amount" means an amount that is effective to prevent, alleviate or ameliorate symptoms of disease or prolong the survival of the subject being treated.

The following table lists abbreviations used within the present document.

TABLE 1

| | abbreviations |
|---|---|
| HPLC | high performance liquid chromatography |
| Huenig's base | N,N-diisopropylethylamine |
| Lawesson's reagent | 2,4-bis(4-methoxyphenyl)-1,3-dithia-2,4-diphosphetane-2,4-disulfide |
| NMR | nuclear magnetic resonance |
| tert-butyl-x-phos | 2-di-tert-butylphosphino-2',4',6'-triisopropylbiphenyl |

The invention also provides pharmaceutical compositions, methods of using, and methods of preparing the aforementioned compounds.

All separate embodiments can be combined.

One embodiment of the invention is a compound of formula I,

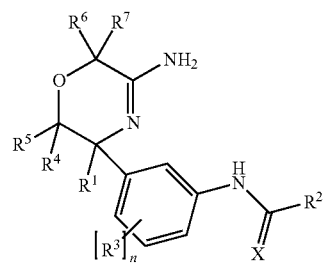

wherein
X is O or S,
R$^1$ is selected from the group consisting of
  i) lower alkyl,
  ii) lower alkyl substituted by 1-5 substituents individually selected from cycloalkyl, halogen, halogen-lower alkoxy and lower alkoxy, and
  iii) cycloalkyl,
R$^2$ is selected from the group consisting of
  i) H,
  ii) lower alkyl,
  iii) lower alkyl substituted by 1-5 substituents individually selected from cycloalkyl, halogen, halogen-lower alkoxy, heterocyclyl and lower alkoxy,
  iv) aryl,
  v) aryl substituted by 1-4 substituents individually selected from cyano, cyano-lower alkyl, halogen, halogen-lower alkoxy, halogen-lower alkyl, heteroaryl, lower alkoxy, lower alkoxy-lower alkyl and lower alkyl,
  vi) cycloalkyl,
  vii) cycloalkyl substituted by 1-4 substituents individually selected from cyano, cyano-lower alkyl, halogen, halogen-lower alkoxy, halogen-lower alkyl, lower alkoxy, lower alkoxy-lower alkyl and lower alkyl, viii) heteroaryl,
  ix) heteroaryl substituted by 1-4 substituents individually selected from aryl, cyano, cyano-lower alkyl, halogen, halogen-lower alkoxy, halogen-lower alkyl, cycloalkyl-lower alkoxy, lower alkenyl-lower alkoxy, aryl-lower alkoxy, heteroaryl, heterocyclyl, lower alkoxy, lower alkoxy-lower alkyl and lower alkyl,
  x) heterocyclyl, and
  xi) heterocyclyl, substituted by 1-4 substituents individually selected from amino, cyano, cyano-lower alkyl, halogen, halogen-lower alkoxy, halogen-lower alkyl, lower alkoxy, lower alkoxy-lower alkyl and lower alkyl,
R$^3$ is individually selected from the group consisting of
  i) halogen and
  ii) lower alkyl,
R$^4$ is individually selected from the group consisting of
  i) H and
  ii) lower alkyl,
R$^5$ is individually selected from the group consisting of
  i) H and
  ii) lower alkyl,
R$^6$ is individually selected from the group consisting of
  i) H and
  ii) lower alkyl,
R$^7$ is individually selected from the group consisting of
  i) H,
  ii) aryl, and
  iii) lower alkyl, and
n is 0, 1 or 2,
or pharmaceutically acceptable salts thereof.

One embodiment of the invention is a compound of formula I, wherein
X is O or S,
$R^1$ is selected from the group consisting of
  i) lower alkyl and
  ii) cycloalkyl,
$R^2$ is selected from the group consisting of
  i) H,
  ii) lower alkyl substituted by 1-5 substituents individually selected from cycloalkyl, halogen, heterocyclyl and lower alkoxy,
  iii) aryl substituted by 1-4 substituents individually selected from cyano, halogen and heteroaryl,
  iv) cycloalkyl,
  v) cycloalkyl substituted by 1-4 substituents individually selected from halogen, halogen-lower alkyl, lower alkoxy-lower alkyl and lower alkyl,
  vi) heteroaryl,
  vii) heteroaryl substituted by 1-4 substituents individually selected from aryl, cyano, halogen, halogen-lower alkoxy, halogen-lower alkyl, cycloalkyl-lower alkoxy, lower alkenyl-lower alkoxy, aryl-lower alkoxy, heteroaryl, heterocyclyl, and lower alkyl, and
  viii) heterocyclyl,
$R^3$ is halogen,
$R^4$ is H or lower alkyl,
$R^5$ is H or lower alkyl,
$R^6$ is H or lower alkyl,
$R^7$ is H, aryl or lower alkyl, and
n is 0 or 1.

One embodiment of the invention is a compound of formula I, which is a compound of formula Ix,

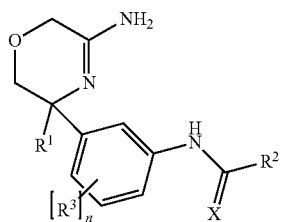

wherein
X is O or S,
$R^1$ is selected from the group consisting of
  i) lower alkyl,
  ii) lower alkyl substituted by 1-5 substituents individually selected from cycloalkyl, halogen, halogen-lower alkoxy and lower alkoxy,
  iii) cycloalkyl, and
$R^2$ is selected from the group consisting of
  i) lower alkyl substituted by 1-5 halogen,
  ii) aryl,
  iii) aryl substituted by 1-4 substituents individually selected from cyano, cyano-lower alkyl, halogen, halogen-lower alkoxy, halogen-lower alkyl, lower alkoxy, lower alkoxy-lower alkyl and lower alkyl,
  iv) heteroaryl, and
  v) heteroaryl substituted by 1-4 substituents individually selected from cyano, cyano-lower alkyl, halogen, halogen-lower alkoxy, halogen-lower alkyl, lower alkoxy, lower alkoxy-lower alkyl and lower alkyl,
$R^3$ is individually selected from the group consisting of
  i) halogen and
  ii) lower alkyl, and
n is 0, 1 or 2,
or pharmaceutically acceptable salts thereof.

One embodiment of the invention is a compound of formula Ix, wherein
X is O or S,
$R^1$ is selected from the group consisting of
  i) lower alkyl,
  ii) lower alkyl substituted by 1-5 substituents individually selected from cycloalkyl, halogen, halogen-lower alkoxy and lower alkoxy,
  iii) cycloalkyl, and
$R^2$ is selected from the group consisting of
  i) lower alkyl substituted by 1-5 halogen,
  ii) aryl,
  iii) aryl substituted by 1-4 substituents individually selected from cyano, cyano-lower alkyl, halogen, halogen-lower alkoxy, halogen-lower alkyl, lower alkoxy, lower alkoxy-lower alkyl and lower alkyl,
  iv) cycloalkyl,
  v) cycloalkyl substituted by 1-4 substituents individually selected from cyano, cyano-lower alkyl, halogen, halogen-lower alkoxy, halogen-lower alkyl, lower alkoxy, lower alkoxy-lower alkyl and lower alkyl,
  vi) heteroaryl,
  vii) heteroaryl substituted by 1-4 substituents individually selected from cyano, cyano-lower alkyl, halogen, halogen-lower alkoxy, halogen-lower alkyl, lower alkoxy, lower alkoxy-lower alkyl and lower alkyl,
  viii) heterocyclyl, and
  ix) heterocyclyl, substituted by 1-4 substituents individually selected from cyano, cyano-lower alkyl, halogen, halogen-lower alkoxy, halogen-lower alkyl, lower alkoxy, lower alkoxy-lower alkyl and lower alkyl,
$R^3$ is individually selected from the group consisting of
  i) halogen and
  ii) lower alkyl, and
n is 0, 1 or 2,
or pharmaceutically acceptable salts thereof.

One embodiment of the invention is a compound of formula Ix, wherein
X is O or S,
$R^1$ is lower alkyl or cycloalkyl,
$R^2$ is selected from the group consisting of
  i) lower alkyl substituted by 1-5 halogen,
  ii) aryl,
  iii) aryl substituted by 1-4 halogen,
  iv) heteroaryl, and
  v) heteroaryl substituted by 1-4 substituents individually selected from halogen, halogen-lower alkoxy, halogen-lower alkyl and lower alkyl,
$R^3$ is halogen, and
n is 0 or 1,
or pharmaceutically acceptable salts thereof.

One embodiment of the invention is a compound of formula I or Ix, where X is O, $R^1$ is methyl, $R^2$ is pyridinyl or pyridinyl substituted by 1 or 2 halogens, selected independently from fluoro and chloro, $R^3$ is fluoro and n is 1.

One embodiment of the invention is a compound of formula I or Ix, where X is O, $R^1$ is methyl, $R^2$ is pyridinyl or pyridinyl substituted by 1 or 2 halogens, selected independently from fluoro and chloro and n is 0.

One embodiment of the invention is a compound of formula I or Ix, where X is O, $R^1$ is methyl, $R^2$ is phenyl or phenyl substituted by 1 or 2 halogens, selected independently from fluoro and chloro, $R^3$ is fluoro and n is 1.

One embodiment of the invention is a compound of formula I or Ix, where X is O, R¹ is methyl, R² is phenyl or phenyl substituted by 1 or 2 halogens, selected independently from fluoro and chloro and n is 0.

One embodiment of the invention is a compound of formula I or Ix, where X is O.

One embodiment of the invention is a compound of formula I or Ix, where X is S.

One embodiment of the invention is a compound of formula I or Ix, where R¹ is selected from the group consisting of lower alkyl and cycloalkyl.

One embodiment of the invention is a compound of formula I or Ix, where R¹ is selected from the group consisting of methyl and cyclopropyl.

One embodiment of the invention is a compound of formula I or Ix, where R¹ is lower alkyl.

One embodiment of the invention is a compound of formula I or Ix, where R¹ is methyl.

One embodiment of the invention is a compound of formula I or Ix, where R¹ is cycloalkyl.

One embodiment of the invention is a compound of formula I or Ix, where R¹ is cyclopropyl.

One embodiment of the invention is a compound of formula I or Ix, where R² is selected from the group consisting of
i) H,
ii) lower alkyl substituted by 1-5 substituents individually selected from cycloalkyl, halogen, heterocyclyl and lower alkoxy,
iii) aryl substituted by 1-4 substituents individually selected from cyano, halogen and heteroaryl,
iv) cycloalkyl,
v) cycloalkyl substituted by 1-4 substituents individually selected from halogen, halogen-lower alkyl and lower alkoxy-lower alkyl,
vi) heteroaryl,
vii) heteroaryl substituted by 1-4 substituents individually selected from aryl, cyano, halogen, halogen-lower alkoxy, halogen-lower alkyl, cycloalkyl-lower alkoxy, lower alkenyl-lower alkoxy, aryl-lower alkoxy, heteroaryl, heterocyclyl, and lower alkyl, and
vi) heterocyclyl.

One embodiment of the invention is a compound of formula I or Ix, where R² is lower alkyl substituted by 1-5 halogens, aryl substituted by 1-4 halogens, heteroaryl or heteroaryl substituted by 1-4 substituents individually selected from halogen, halogen-lower alkoxy, halogen-lower alkyl and lower alkyl.

One embodiment of the invention is a compound of formula I or Ix, where R² is heteroaryl substituted by 1-4 substituents individually selected from halogen, halogen-lower alkoxy, halogen-lower alkyl and lower alkyl.

One embodiment of the invention is a compound of formula I or Ix, where R² is 1-methyl-1H-indazol-3-yl, 2-methyl-oxazol-4-yl, 2-methyl-thiazol-4-yl, 3-chloro-phenyl, 4-chloro-2-fluoro-phenyl, 4-chloro-2-iodo-phenyl, 4-chlorophenyl, 5-chloro-pyridin-2-yl, 5-chloro-thien-2-yl, 1-(2,2,2-trifluoro-ethyl)-1H-pyrazol-3-yl, 1,1,2,2,2-pentafluoroethyl, 5-(2,2,2-trifluoro-ethoxy)-pyridin-2-yl, pyrazin-2-yl, pyrazolo[1,5-a]pyridin-2-yl, 2,4-dichloro-phenyl, 2,5-difluoro-phenyl, 2,5-dimethyl-fur-3-yl, 2,5-dimethyl-oxazol-4-yl, 2,5-dimethyl-thien-3-yl, 3,5-dichloro-pyridin-2-yl, 3,5-difluoro-pyridin-2-yl.

One embodiment of the invention is a compound of formula I or Ix, where R² is 1-(2,2,2-trifluoro-ethyl)-1H-pyrazol-3-yl, 1,1,1,2-tetrafluoro-ethyl, 1,1,2,2,2-pentafluoroethyl, 1,1,2,2-tetrafluoro-ethyl, 1,1-difluoromethyl-1H-pyrazole-3-yl, 1-methoxymethyl-cycloprop-1-yl, 1-methyl-1H-indazol-3-yl, 1-trifluoromethyl-cycloprop-1-yl, 2,2,2-trifluoroethyl-, 2,2-difluoro-cycloprop-1-yl, 2,2-difluoroethyl, 2,4-dichloro-phenyl, 2,5-difluoro-phenyl, 2,5-dimethyl-fur-3-yl, 2,5-dimethyl-oxazol-4-yl, 2,5-dimethyl-thien-3-yl, 2-fluoro-ethyl, 2-methyl-4-trifluoromethyl-thiazole-5-yl, 2-methyl-oxazol-4-yl, 2-methyl-thiazol-4-yl, 3-(2,2,2-trifluoro-ethoxy)-pyridin-2-yl, 3,3,3-trifluoro-1-(tetrahydro-furan-2-yl)-propyl, 3,3-difluoro-cyclobut-1-yl, 3,5-dichloro-pyridin-2-yl, 3,5-difluoro-pyridin-2-yl, 3-chloro-5-cyano-pyridin-2-yl, 3-chloro-5-trifluoromethyl-pyridin-2-yl, 3-chloro-cyclobut-1-yl, 3-chloro-phenyl, 3-chloro-thiophen-2-yl, 3-fluoro-pyridin-2-yl, 3-methyl-thiophen-2-yl, 3-sec-butyl-5-chloro-pyridin-2-yl, 4-chloro-1-methyl-1H-pyrazol-3-yl, 4-chloro-2-fluoro-phenyl, 4-chloro-2-iodo-phenyl, 4-chloro-phenyl, 4-cyano-2-fluoro-phenyl, 4-oxazol-5-yl-phenyl, 5-(2,2,2-trifluoro-ethoxy)-pyridin-2-yl, 5-(2,2-difluoro-ethoxy)-pyridin-2-yl, 5-(2-fluoro-ethoxy)-pyridin-2-yl, 5-benzyloxy-pyridin-2-yl, 5-but-3-enyloxy-pyridin-2-yl, 5-butyl-pyridin-2-yl, 5-chloro-3-ethyl-pyridin-2-yl, 5-chloro-3-fluoro-pyridin-2-yl, 5-chloro-3-methyl-pyridin-2-yl, 5-chloro-pyridin-2-yl, 5-chloro-pyrimidin-2-yl, 5-chloro-thien-2-yl, 5-cyano-pyridin-2-yl, 5-cyclopropylmethoxy-pyridin-2-yl, 5-difluoromethoxy-pyridin-2-yl, 5-fluoro-pyridin-2-yl, 5-furan-2-yl-isoxazol-3-yl, 5-furan-2-yl-pyridin-2-yl, 5-methyl-pyrazin-2-yl, 5-phenyl-oxazol-4-yl, 5-pyrrolidin-1-yl-pyridin-2-yl, 5-thiophen-2-yl-isoxazol-3-yl, 5-trifluoromethyl-pyrazin-2-yl, 5-trifluoromethyl-pyrimidin-2-yl, cyclopropyl, difluoro-methyl, ethyl, fluoro-isopropyl, H, isopropyl, methyl, methoxy-methyl, oxazole-2-yl, pyrazin-2-yl, pyrazolo[1,5-a]pyridin-2-yl, pyrimidin-4-yl or tetrahydro-furan-3-yl.

One embodiment of the invention is a compound of formula I or Ix, where R² is 1-methyl-1H-indazol-3-yl, 2-methyl-oxazol-4-yl, 2-methyl-thiazol-4-yl, 3-chloro-phenyl, 4-chloro-2-fluoro-phenyl, 4-chloro-2-iodo-phenyl, 4-chlorophenyl, 5-chloro-pyridin-2-yl, 5-chloro-thien-2-yl, 1-(2,2,2-trifluoro-ethyl)-1H-pyrazol-3-yl, 1,1,2,2,2-pentafluoroethyl, 5-(2,2,2-trifluoro-ethoxy)-pyridin-2-yl, pyrazin-2-yl, pyrazolo[1,5-a]pyridin-2-yl, 2,4-dichloro-phenyl, 2,5-difluoro-phenyl, 2,5-dimethyl-fur-3-yl, 2,5-dimethyl-oxazol-4-yl, 2,5-dimethyl-thien-3-yl, 3,5-dichloro-pyridin-2-yl or 3,5-difluoro-pyridin-2-yl.

One embodiment of the invention is a compound of formula I or Ix, where R² is 1-(2,2,2-trifluoro-ethyl)-1H-pyrazol-3-yl, 1,1,1,2-tetrafluoro-ethyl, 1,1,2,2,2-pentafluoroethyl, 1,1,2,2-tetrafluoro-ethyl, 1,1-difluoromethyl-1H-pyrazole-3-yl, 1-methoxymethyl-cycloprop-1-yl, 1-methyl-1H-indazol-3-yl, 1-trifluoromethyl-cycloprop-1-yl, 2,2,2-trifluoroethyl-, 2,2-difluoro-cycloprop-1-yl, 2,2-difluoroethyl, 2,4-dichloro-phenyl, 2,5-difluoro-phenyl, 2,5-dimethyl-fur-3-yl, 2,5-dimethyl-oxazol-4-yl, 2,5-dimethyl-thien-3-yl, 2-fluoro-ethyl, 2-methyl-4-trifluoromethyl-thiazole-5-yl, 2-methyl-oxazol-4-yl, 2-methyl-thiazol-4-yl, 3-(2,2,2-trifluoro-ethoxy)-pyridin-2-yl, 3,3,3-trifluoro-1-(tetrahydro-furan-2-yl)-propyl, 3,3-difluoro-cyclobut-1-yl, 3,5-dichloro-pyridin-2-yl, 3,5-difluoro-pyridin-2-yl, 3-chloro-5-cyano-pyridin-2-yl, 3-chloro-5-trifluoromethyl-pyridin-2-yl, 3-chloro-cyclobut-1-yl, 3-chloro-phenyl, 3-chloro-thiophen-2-yl, 3-fluoro-pyridin-2-yl, 3-methyl-thiophen-2-yl, 3-sec-butyl-5-chloro-pyridin-2-yl, 4-chloro-1-methyl-1H-pyrazol-3-yl, 4-chloro-2-fluoro-phenyl, 4-chloro-2-iodo-phenyl, 4-chloro-phenyl, 4-chloro-phenyl, 4-cyano-2-fluoro-phenyl, 4-oxazol-5-yl-phenyl, 5-(2,2,2-trifluoro-ethoxy)-pyridin-2-yl, 5-(2,2-difluoro-ethoxy)-pyridin-2-yl, 5-(2-fluoro-ethoxy)-pyridin-2-yl, 5-benzyloxy-pyridin-2-yl, 5-but-3-enyloxy-pyridin-2-yl, 5-butyl-pyridin-2-yl, 5-chloro-3-ethyl-pyridin-2-yl, 5-chloro-3-fluoro-pyridin- 2-yl, 5-chloro-3-methyl-pyridin-2-yl, 5-chloro-pyridin-2-yl, 5-chloro-pyrimidin-2-yl, 5-chloro-thien-2-yl, 5-cyano-pyridin-2-yl, 5-cyclopropylmethoxy-pyridin-2-yl, 5-difluoromethoxy-pyridin-2-yl, 5-fluoro-pyridin-2-yl, 5-furan-2-yl-isoxazole-3-yl, 5-furan-2-yl-pyridin-2-yl, 5-methyl-pyrazine-2-yl, 5-phenyl-oxazole-4-yl, 5-pyrrolidin-1-yl-pyridin-2-yl or 5-thiophen-2-yl-isoxazole-3-yl.

One embodiment of the invention is a compound of formula I or Ix, where $R^2$ is H.

One embodiment of the invention is a compound of formula I or Ix where $R^2$ is lower alkyl.

One embodiment of the invention is a compound of formula I or Ix, where $R^2$ is methyl.

One embodiment of the invention is a compound of formula I or Ix, where $R^2$ is ethyl.

One embodiment of the invention is a compound of formula I or Ix, where $R^2$ is isopropyl.

One embodiment of the invention is a compound of formula I or Ix where $R^2$ is lower alkyl substituted by 1-5 halogens.

One embodiment of the invention is a compound of formula I or Ix where $R^2$ is 1,1,2,2,2-pentafluoro-ethyl.

One embodiment of the invention is a compound of formula I or Ix where $R^2$ is 1,1,2,2-tetrafluoro-ethyl.

One embodiment of the invention is a compound of formula I or Ix where $R^2$ is 1,1,1,2-tetrafluoro-ethyl.

One embodiment of the invention is a compound of formula I or Ix where $R^2$ is 2,2,2-trifluoroethyl.

One embodiment of the invention is a compound of formula I or Ix where $R^2$ is 2,2-difluoro-ethyl.

One embodiment of the invention is a compound of formula I or Ix where $R^2$ is 2-fluoro-ethyl.

One embodiment of the invention is a compound of formula I or Ix where $R^2$ is difluoro-methyl.

One embodiment of the invention is a compound of formula I or Ix where $R^2$ is fluoro-isopropyl.

One embodiment of the invention is a compound of formula I or Ix where $R^2$ is lower alkyl substituted by lower alkoxy.

One embodiment of the invention is a compound of formula I or Ix where $R^2$ is methoxy-methyl.

One embodiment of the invention is a compound of formula I or Ix where $R^2$ is lower alkyl substituted by halogen and heterocyclyl.

One embodiment of the invention is a compound of formula I or Ix where $R^2$ is 3,3,3-trifluoro-1-(tetrahydro-furan-2-yl-propyl.

One embodiment of the invention is a compound of formula I or Ix where $R^2$ is cycloalkyl.

One embodiment of the invention is a compound of formula I or Ix where $R^2$ is cyclopropyl.

One embodiment of the invention is a compound of formula I or Ix where $R^2$ is cycloalkyl substituted by halogen.

One embodiment of the invention is a compound of formula I or Ix where $R^2$ is 2,2-difluoro-cycloprop-1-yl.

One embodiment of the invention is a compound of formula I or Ix where $R^2$ is 3-chloro-cyclobut-1-yl.

One embodiment of the invention is a compound of formula I or Ix where $R^2$ is 3,3-difluoro-cyclobut-1-yl.

One embodiment of the invention is a compound of formula I or Ix where $R^2$ is cycloalkyl substituted by halogen-lower alkyl.

One embodiment of the invention is a compound of formula I or Ix where $R^2$ is 1-trifluoromethyl-cycloprop-1-yl.

One embodiment of the invention is a compound of formula I or Ix where $R^2$ is cycloalkyl substituted by lower alkoxy-lower alkyl.

One embodiment of the invention is a compound of formula I or Ix where $R^2$ is 1-methoxymethyl-cycloprop-1-yl.

One embodiment of the invention is a compound of formula I or Ix where $R^2$ is aryl substituted by 1-4 halogens.

One embodiment of the invention is a compound of formula I or Ix where $R^2$ is phenyl substituted by 1-4 halogens.

One embodiment of the invention is a compound of formula I or Ix where $R^2$ is 2,4-dichloro-phenyl.

One embodiment of the invention is a compound of formula I or Ix where $R^2$ is 2,5-difluoro-phenyl.

One embodiment of the invention is a compound of formula I or Ix where $R^2$ is 3-chloro-phenyl.

One embodiment of the invention is a compound of formula I or Ix where $R^2$ is 4-chloro-2-fluoro-phenyl.

One embodiment of the invention is a compound of formula I or Ix where $R^2$ is 4-chloro-2-iodo-phenyl.

One embodiment of the invention is a compound of formula I or Ix where $R^2$ is 4-chloro-phenyl.

One embodiment of the invention is a compound of formula I or Ix where $R^2$ is aryl substituted by halogen and cyano.

One embodiment of the invention is a compound of formula I or Ix where $R^{24}$-cyano-2-fluoro-phenyl.

One embodiment of the invention is a compound of formula I or Ix where $R^2$ is aryl substituted by heteroaryl.

One embodiment of the invention is a compound of formula I or Ix where $R^2$ is 4-oxazol-5-yl-phenyl.

One embodiment of the invention is a compound of formula I or Ix where $R^2$ is aryl substituted by 1-4 substituents individually selected from halogen, halogen-lower alkoxy, halogen-lower alkyl and lower alkyl.

One embodiment of the invention is a compound of formula I or Ix where $R^2$ is heteroaryl.

One embodiment of the invention is a compound of formula I or Ix where $R^2$ is pyrazin-2-yl.

One embodiment of the invention is a compound of formula I or Ix where $R^2$ is pyrazolo[1,5-a]pyridin-2-yl.

One embodiment of the invention is a compound of formula I or Ix where $R^2$ is pyrimidin-4-yl.

One embodiment of the invention is a compound of formula I or Ix where $R^2$ is oxazole-2-yl.

One embodiment of the invention is a compound of formula I or Ix where $R^2$ is heteroaryl substituted by aryl.

One embodiment of the invention is a compound of formula I or Ix where $R^2$ is 5-phenyl-oxazol-4-yl.

One embodiment of the invention is a compound of formula I or Ix where $R^2$ is heteroaryl substituted by cyano.

One embodiment of the invention is a compound of formula I or Ix where $R^2$ is 5-cyano-pyridin-2-yl.

One embodiment of the invention is a compound of formula I or Ix where $R^2$ is heteroaryl substituted by halogen.

One embodiment of the invention is a compound of formula I or Ix where $R^2$ is 5-chloro-pyridin-2-yl.

One embodiment of the invention is a compound of formula I or Ix where $R^2$ is 3,5-dichloro-pyridin-2-yl.

One embodiment of the invention is a compound of formula I or Ix where $R^2$ is 3,5-difluoro-pyridin-2-yl.

One embodiment of the invention is a compound of formula I or Ix where $R^2$ is 5-chloro-thien-2-yl.

One embodiment of the invention is a compound of formula I or Ix where $R^2$ is 5-chloro-pyrimidin-2-yl.

One embodiment of the invention is a compound of formula I or Ix where $R^2$ is 3-fluoro-pyridin-2-yl.

One embodiment of the invention is a compound of formula I or Ix where $R^2$ is 3-chloro-thiophen-2-yl.

One embodiment of the invention is a compound of formula I or Ix where $R^2$ is 5-chloro-3-fluoro-pyridin-2-yl.

One embodiment of the invention is a compound of formula I or Ix where $R^2$ is 5-fluoro-pyridin-2-yl.

One embodiment of the invention is a compound of formula I or Ix where $R^2$ is heteroaryl substituted by halogen-lower alkoxy.

One embodiment of the invention is a compound of formula I or Ix where $R^2$ is 5-(2,2,2-trifluoro-ethoxy)-pyridin-2-yl.

One embodiment of the invention is a compound of formula I or Ix where $R^2$ is 3-(2,2,2-trifluoro-ethoxy)-pyridin-2-yl.

One embodiment of the invention is a compound of formula I or Ix where $R^2$ is 5-(2-fluoro-ethoxy)-pyridin-2-yl.

One embodiment of the invention is a compound of formula I or Ix where $R^2$ is 5-(2,2-difluoro-ethoxy)-pyridin-2-yl.

One embodiment of the invention is a compound of formula I or Ix where $R^2$ is 5-difluoromethoxy-pyridin-2-yl.

One embodiment of the invention is a compound of formula I or Ix where $R^2$ is heteroaryl substituted by halogen-lower alkyl.

One embodiment of the invention is a compound of formula I or Ix where $R^2$ is 1-(2,2,2-trifluoro-ethyl)-1H-pyrazol-3-yl.

One embodiment of the invention is a compound of formula I or Ix where $R^2$ is 5-trifluoromethyl-pyrazin-2-yl.

One embodiment of the invention is a compound of formula I or Ix where $R^2$ is 5-trifluoromethyl-pyrimidin-2-yl.

One embodiment of the invention is a compound of formula I or Ix where $R^2$ is heteroaryl substituted by cycloalkyl-lower alkoxy.

One embodiment of the invention is a compound of formula I or Ix where $R^2$ is 5-cyclopropylmethoxy-pyridin-2-yl.

One embodiment of the invention is a compound of formula I or Ix where $R^2$ is heteroaryl substituted by lower alkenyl-lower alkoxy.

One embodiment of the invention is a compound of formula I or Ix where $R^2$ is 5-but-3-enyloxy-pyridin-2-yl.

One embodiment of the invention is a compound of formula I or Ix where $R^2$ is heteroaryl substituted by aryl-lower alkoxy.

One embodiment of the invention is a compound of formula I or Ix where $R^2$ is 5-benzyloxy-pyridin-2-yl.

One embodiment of the invention is a compound of formula I or Ix where $R^2$ is heteroaryl substituted by heteroaryl.

One embodiment of the invention is a compound of formula I or Ix where $R^2$ is 5-furan-2-yl-isoxazole-3-yl.

One embodiment of the invention is a compound of formula I or Ix where $R^2$ is 5-furan-2-yl-pyridin-2-yl.

One embodiment of the invention is a compound of formula I or Ix where $R^2$ is 5-thiophen-2-yl-isoxazole-3-yl.

One embodiment of the invention is a compound of formula I or Ix where $R^2$ is heteroaryl substituted by heterocyclyl.

One embodiment of the invention is a compound of formula I or Ix where $R^2$ is 5-pyrrolidin-1-yl-pyridin-2-yl.

One embodiment of the invention is a compound of formula I or Ix where $R^2$ is heteroaryl substituted by lower alkyl.

One embodiment of the invention is a compound of formula I or Ix where $R^2$ is 2,5-dimethyl-fur-3-yl.

One embodiment of the invention is a compound of formula I or Ix where $R^2$ is 2,5-dimethyl-oxazol-4-yl.

One embodiment of the invention is a compound of formula I or Ix where $R^2$ is 2,5-dimethyl-thien-3-yl.

One embodiment of the invention is a compound of formula I or Ix where $R^2$ is 5-methyl-pyrazine-2-yl.

One embodiment of the invention is a compound of formula I or Ix where $R^2$ is 1-methyl-1H-indazol-3-yl.

One embodiment of the invention is a compound of formula I or Ix where $R^2$ is 2-methyl-oxazol-4-yl.

One embodiment of the invention is a compound of formula I or Ix where $R^2$ is 2-methyl-thiazol-4-yl.

One embodiment of the invention is a compound of formula I or Ix where $R^2$ is 5-butyl-pyridin-2-yl.

One embodiment of the invention is a compound of formula I or Ix where $R^2$ is 1,1-difluoromethyl-1H-pyrazol-3-yl.

One embodiment of the invention is a compound of formula I or Ix where $R^2$ is 3,5-difluoro-pyridin-2-yl.

One embodiment of the invention is a compound of formula I or Ix where $R^2$ is 3-methyl-thiophen-2-yl.

One embodiment of the invention is a compound of formula I or Ix where $R^2$ is heteroaryl substituted by halogen and lower alkyl.

One embodiment of the invention is a compound of formula I or Ix where $R^2$ is 3-chloro-5-trifluoromethyl-pyridin-2-yl.

One embodiment of the invention is a compound of formula I or Ix where $R^2$ is 4-chloro-1-methyl-1H-pyrazole-3-yl.

One embodiment of the invention is a compound of formula I or Ix where $R^2$ is 5-chloro-3-ethyl-pyridin-2-yl.

One embodiment of the invention is a compound of formula I or Ix where $R^2$ is 3-sec-butyl-5-chloro-pyridin-2-yl.

One embodiment of the invention is a compound of formula I or Ix where $R^2$ is 5-chloro-3-methyl-pyridin-2-yl.

One embodiment of the invention is a compound of formula I or Ix where $R^2$ is heteroaryl substituted by halogen and cyano.

One embodiment of the invention is a compound of formula I or Ix where $R^2$ is 3-chloro-5-cyano-pyridin-2-yl.

One embodiment of the invention is a compound of formula I or Ix where $R^2$ is heteroaryl substituted by halogen-lower alkyl and lower alkyl.

One embodiment of the invention is a compound of formula I or Ix where $R^2$ is 2-methyl-4-trifluoromethyl-thiazol-5-yl.

One embodiment of the invention is a compound of formula I or Ix where $R^2$ is heterocyclyl.

One embodiment of the invention is a compound of formula I or Ix where $R^2$ is tetrahydro-furan-3-yl.

One embodiment of the invention is a compound of formula I or Ix where n is 0.

One embodiment of the invention is a compound of formula I or Ix where n is 1.

One embodiment of the invention is a compound of formula I or Ix where $R^3$ is halogen.

One embodiment of the invention is a compound of formula I or Ix where $R^3$ is F.

One embodiment of the invention is a compound of formula I or Ix selected from the group consisting of 3,5-Difluoro-pyridine-2-carboxylic acid [3-((RS)-5-amino-3-methyl-3,6-dihydro-2H-[1,4]oxazin-3-yl)-phenyl]-amide, 3,5-Dichloro-pyridine-2-carboxylic acid [3-((RS)-5-amino-3-methyl-3,6-dihydro-2H-[1,4]oxazin-3-yl)-phenyl]-amide, (RS)-N-[3-(5-Amino-3-methyl-3,6-dihydro-2H-[1,4]oxazin-3-yl)-phenyl]-4-chloro-2-fluoro-benzamide, (RS)-N-[3-(5-Amino-3-methyl-3,6-dihydro-2H-[1,4]oxazin-3-yl)-phenyl]-2,4-dichloro-benzamide, (RS)-N-[3-(5-Amino-3-methyl-3,6-dihydro-2H-[1,4]oxazin-3-yl)-phenyl]-2,5-difluoro-benzamide, (RS)-N-[3-(5-Amino-3-methyl-3,6-dihydro-2H-[1,4]oxazin-3-yl)-phenyl]-3-chloro-benzamide, 5-Chloro-pyridine-2-carboxylic acid [3-((RS)-5-amino-3-methyl-3,6-dihydro-2H-[1,4]oxazin-3-yl)-phenyl]-amide,
5-Chloro-thiophene-2-carboxylic acid [3-((RS)-5-amino-3-methyl-3,6-dihydro-2H-[1,4]oxazin-3-yl)-phenyl]-amide,
2,5-Dimethyl-thiophene-3-carboxylic acid [3-((RS)-5-amino-3-methyl-3,6-dihydro-2H-[1,4]oxazin-3-yl)-phenyl]-amide,
2-Methyl-thiazole-4-carboxylic acid [3-((RS)-5-amino-3-methyl-3,6-dihydro-2H-[1,4]oxazin-3-yl)-phenyl]-amide,
2,5-Dimethyl-oxazole-4-carboxylic acid [3-((RS)-5-amino-3-methyl-3,6-dihydro-2H-[1,4]oxazin-3-yl)-phenyl]-amide,
2-Methyl-oxazole-4-carboxylic acid [3-((RS)-5-amino-3-methyl-3,6-dihydro-2H-[1,4]oxazin-3-yl)-phenyl]-amide,
2,5-Dimethyl-furan-3-carboxylic acid [3-((RS)-5-amino-3-methyl-3,6-dihydro-2H-[1,4]oxazin-3-yl)-phenyl]-amide,
1-(2,2,2-Trifluoro-ethyl)-1H-pyrazole-3-carboxylic acid [3-((RS)-5-amino-3-methyl-3,6-dihydro-2H-[1,4]oxazin-3-yl)-phenyl]-amide,
1-Methyl-1H-indazole-3-carboxylic acid [3-((RS)-5-amino-3-methyl-3,6-dihydro-2H-[1,4]oxazin-3-yl)-phenyl]-amide,
Pyrazolo[1,5-a]pyridine-2-carboxylic acid [3-((RS)-5-amino-3-methyl-3,6-dihydro-2H-[1,4]oxazin-3-yl)-phenyl]-amide,
(RS)-N-[3-(5-Amino-3-methyl-3,6-dihydro-2H-[1,4]oxazin-3-yl)-phenyl]-4-chloro-2-iodo-benzamide,
5-Chloro-pyridine-2-carboxylic acid [3-((R)-5-amino-3-methyl-3,6-dihydro-2H-[1,4]oxazin-3-yl)-phenyl]-amide,
(RS)-N-[3-(5-Amino-3-methyl-3,6-dihydro-2H-[1,4]oxazin-3-yl)-4-fluoro-phenyl]-4-chloro-benzamide,
5-Chloro-pyridine-2-carboxylic acid [3-((RS)-5-amino-3-methyl-3,6-dihydro-2H-[1,4]oxazin-3-yl)-4-fluoro-phenyl]-amide,
5-Chloro-pyridine-2-carboxylic acid [3-((R)-5-amino-3-methyl-3,6-dihydro-2H-[1,4]oxazin-3-yl)-4-fluoro-phenyl]-amide,
5-Chloro-pyridine-2-carboxylic acid [3-((RS)-5-amino-3-cyclopropyl-3,6-dihydro-2H-[1,4]oxazin-3-yl)-4-fluoro-phenyl]-amide,
5-(2,2,2-Trifluoro-ethoxy)-pyridine-2-carboxylic acid [3-((RS)-5-amino-3-cyclopropyl-3,6-dihydro-2H-[1,4]oxazin-3-yl)-4-fluoro-phenyl]-amide,
5-(2,2,2-Trifluoro-ethoxy)-pyridine-2-carboxylic acid [3-((RS)-5-amino-3-methyl-3,6-dihydro-2H-[1,4]oxazin-3-yl)-phenyl]-amide,
Pyrazine-2-carboxylic acid [3-((RS)-5-amino-3-methyl-3,6-dihydro-2H-[1,4]oxazin-3-yl)-phenyl]-amide,
(RS)-N-[3-(5-Amino-3-methyl-3,6-dihydro-2H-[1,4]oxazin-3-yl)-4-fluoro-phenyl]-2,2,3,3,3-pentafluoro-propionamide,
(RS)-N-[3-(5-Amino-3-methyl-3,6-dihydro-2H-[1,4]oxazin-3-yl)-4-fluoro-phenyl]-4-chloro-thiobenzamide,
5-Chloro-pyridine-2-carboxylic acid [3-((3R,6R) and (3S,6S)-5-amino-6-benzyl-3-methyl-3,6-dihydro-2H-[1,4]oxazin-3-yl)-4-fluoro-phenyl]-amide,
5-Chloro-pyridine-2-carboxylic acid [3-((3R,6S)- and (3S,6R)-5-amino-6-benzyl-3-methyl-3,6-dihydro-2H-[1,4]oxazin-3-yl)-4-fluoro-phenyl]-amide,
5-Chloro-pyridine-2-carboxylic acid [3-((3R,6R)-5-amino-3-methyl-6-phenyl-3,6-dihydro-2H-[1,4]oxazin-3-yl)-4-fluoro-phenyl]-amide,
5-Chloro-pyridine-2-carboxylic acid [3-((3R,6S)-5-amino-3-methyl-6-phenyl-3,6-dihydro-2H-[1,4]oxazin-3-yl)-4-fluoro-phenyl]-amide,
5-Butyl-pyridine-2-carboxylic acid [3-((RS)-5-amino-3-methyl-3,6-dihydro-2H-[1,4]oxazin-3-yl)-phenyl]-amide,
3-Chloro-5-trifluoromethyl-pyridine-2-carboxylic acid [3-((RS)-5-amino-3-methyl-3,6-dihydro-2H-[1,4]oxazin-3-yl)-phenyl]-amide,
3,5-Dichloro-pyridine-2-carboxylic acid [3-((R)-5-amino-3-methyl-3,6-dihydro-2H-[1,4]oxazin-3-yl)-4-fluoro-phenyl]-amide,
5-Chloro-pyrimidine-2-carboxylic acid [3-((R)-5-amino-3-methyl-3,6-dihydro-2H-[1,4]oxazin-3-yl)-4-fluoro-phenyl]-amide,
5-Trifluoromethyl-furan-3-carboxylic acid [3-((R)-5-amino-3-methyl-3,6-dihydro-2H-[1,4]oxazin-3-yl)-4-fluoro-phenyl]-amide,
3-Fluoro-pyridine-2-carboxylic acid [3-((R)-5-amino-3-methyl-3,6-dihydro-2H-[1,4]oxazin-3-yl)-4-fluoro-phenyl]-amide,
3-Chloro-5-trifluoromethyl-pyridine-2-carboxylic acid [3-((R)-5-amino-3-methyl-3,6-dihydro-2H-[1,4]oxazin-3-yl)-4-fluoro-phenyl]-amide,
2-Methyl-oxazole-4-carboxylic acid [3-((R)-5-amino-3-methyl-3,6-dihydro-2H-[1,4]oxazin-3-yl)-4-fluoro-phenyl]-amide,
1-Difluoromethyl-1H-pyrazole-3-carboxylic acid [3-((R)-5-amino-3-methyl-3,6-dihydro-2H-[1,4]oxazin-3-yl)-4-fluoro-phenyl]-amide,
3,5-Difluoro-pyridine-2-carboxylic acid [3-((R)-5-amino-3-methyl-3,6-dihydro-2H-[1,4]oxazin-3-yl)-4-fluoro-phenyl]-amide,
N-[3-((R)-5-Amino-3-methyl-3,6-dihydro-2H-[1,4]oxazin-3-yl)-4-fluoro-phenyl]-4-cyano-2-fluoro-benzamide,
4-Chloro-1-methyl-1H-pyrazole-3-carboxylic acid [3-((R)-5-amino-3-methyl-3,6-dihydro-2H-[1,4]oxazin-3-yl)-4-fluoro-phenyl]-amide,
3-Methyl-thiophene-2-carboxylic acid [3-((R)-5-amino-3-methyl-3,6-dihydro-2H-[1,4]oxazin-3-yl)-4-fluoro-phenyl]-amide,
5-Phenyl-oxazole-4-carboxylic acid [3-((R)-5-amino-3-methyl-3,6-dihydro-2H-[1,4]oxazin-3-yl)-4-fluoro-phenyl]-amide,
3-Chloro-thiophene-2-carboxylic acid [3-((R)-5-amino-3-methyl-3,6-dihydro-2H-[1,4]oxazin-3-yl)-4-fluoro-phenyl]-amide,
2-Methyl-4-trifluoromethyl-thiazole-5-carboxylic acid [3-((R)-5-amino-3-methyl-3,6-dihydro-2H-[1,4]oxazin-3-yl)-4-fluoro-phenyl]-amide,
3-(2,2,2-Trifluoro-ethoxy)-pyridine-2-carboxylic acid [3-((R)-5-amino-3-methyl-3,6-dihydro-2H-[1,4]oxazin-3-yl)-4-fluoro-phenyl]-amide,
5-Chloro-pyridine-2-carboxylic acid [3-((R)-5-amino-2,2,3-trimethyl-3,6-dihydro-2H-[1,4]oxazin-3-yl)-4-fluoro-phenyl]-amide,
5-(2,2,2-Trifluoro-ethoxy)-pyridine-2-carboxylic acid [3-((R)-5-amino-2,2,3-trimethyl-3,6-dihydro-2H-[1,4]oxazin-3-yl)-4-fluoro-phenyl]-amide,
5-Chloro-pyridine-2-carboxylic acid [3-((R)-5-amino-3,6,6-trimethyl-3,6-dihydro-2H-[1,4]oxazin-3-yl)-phenyl]-amide,
(RS)-N-[3-(5-Amino-3-methyl-3,6-dihydro-2H-[1,4]oxazin-3-yl)-4-fluoro-phenyl]-4-oxazol-5-yl-benzamide,
(RS)-2,2-Difluoro-cyclopropanecarboxylic acid [3-((R)-5-amino-3-methyl-3,6-dihydro-2H-[1,4]oxazin-3-yl)-4-fluoro-phenyl]-amide,
Cyclopropanecarboxylic acid [3-((R)-5-amino-2,2,3-trimethyl-3,6-dihydro-2H-[1,4]oxazin-3-yl)-4-fluoro-phenyl]-amide,
1-Trifluoromethyl-cyclopropanecarboxylic acid [3-((R)-5-amino-2,2,3-trimethyl-3,6-dihydro-2H-[1,4]oxazin-3-yl)-4-fluoro-phenyl]-amide, (RS)-2,2-Difluoro-cyclopropanecarboxylic acid [3-((R)-5-amino-2,2,3-trimethyl-3,6-dihydro-2H-[1,4]oxazin-3-yl)-4-fluoro-phenyl]-amide,
1-Trifluoromethyl-cyclopropanecarboxylic acid [3-((RS)-5-amino-3-methyl-3,6-dihydro-2H-[1,4]oxazin-3-yl)-4-fluoro-phenyl]-amide,
3-Chloro-cyclobutanecarboxylic acid [3-((R)-5-amino-3-methyl-3,6-dihydro-2H-[1,4]oxazin-3-yl)-4-fluoro-phenyl]-amide,
3,3-Difluoro-cyclobutanecarboxylic acid [3-((R)-5-amino-3-methyl-3,6-dihydro-2H-[1,4]oxazin-3-yl)-4-fluoro-phenyl]-amide,
5-Cyclopropylmethoxy-pyridine-2-carboxylic acid [3-((RS)-5-amino-3-methyl-3,6-dihydro-2H-[1,4]oxazin-3-yl)-phenyl]-amide,
5-(2-Fluoro-ethoxy)-pyridine-2-carboxylic acid [3-((RS)-5-amino-3-methyl-3,6-dihydro-2H-[1,4]oxazin-3-yl)-phenyl]-amide,
5-(2,2-Difluoro-ethoxy)-pyridine-2-carboxylic acid [3-((RS)-5-amino-3-methyl-3,6-dihydro-2H-[1,4]oxazin-3-yl)-phenyl]-amide,
Pyrimidine-4-carboxylic acid [3-((RS)-5-amino-3-methyl-3,6-dihydro-2H-[1,4]oxazin-3-yl)-phenyl]-amide,
5-But-3-enyloxy-pyridine-2-carboxylic acid [3-((RS)-5-amino-3-methyl-3,6-dihydro-2H-[1,4]oxazin-3-yl)-phenyl]-amide,
5-Methyl-pyrazine-2-carboxylic acid [3-((RS)-5-amino-3-methyl-3,6-dihydro-2H-[1,4]oxazin-3-yl)-phenyl]-amide,
5-Benzyloxy-pyridine-2-carboxylic acid [3-((RS)-5-amino-3-methyl-3,6-dihydro-2H-[1,4]oxazin-3-yl)-phenyl]-amide,
3-Chloro-5-cyano-pyridine-2-carboxylic acid [3-((R)-5-amino-3-methyl-3,6-dihydro-2H-[1,4]oxazin-3-yl)-4-fluoro-phenyl]-amide,
5-Chloro-3-fluoro-pyridine-2-carboxylic acid [3-((RS)-5-amino-3-methyl-3,6-dihydro-2H-[1,4]oxazin-3-yl)-phenyl]-amide,
5-Cyano-pyridine-2-carboxylic acid[3-((RS)-5-amino-3-methyl-3,6-dihydro-2H-[1,4]oxazin-3-yl)-4-fluoro-phenyl]-amide,
5-Chloro-3-ethyl-pyridine-2-carboxylic acid [3-((R)-5-amino-3-methyl-3,6-dihydro-2H-[1,4]oxazin-3-yl)-4-fluoro-phenyl]-amide,
3 (RS)-sec-Butyl-5-chloro-pyridine-2-carboxylic acid [3-((R)-5-amino-3-methyl-3,6-dihydro-2H-[1,4]oxazin-3-yl)-4-fluoro-phenyl]-amide,
5-Cyano-pyridine-2-carboxylic acid [3-((R)-5-amino-3-methyl-3,6-dihydro-2H-[1,4]oxazin-3-yl)-4-fluoro-phenyl]-amide,
5-Difluoromethoxy-pyridine-2-carboxylic acid [3-((R)-5-amino-3-methyl-3,6-dihydro-2H-[1,4]oxazin-3-yl)-4-fluoro-phenyl]-amide,
5-Chloro-3-fluoro-pyridine-2-carboxylic acid [3-((R)-5-amino-3-methyl-3,6-dihydro-2H-[1,4]oxazin-3-yl)-4-fluoro-phenyl]-amide,
5-Furan-2-yl-isoxazole-3-carboxylic acid [3-((RS)-5-amino-3-methyl-3,6-dihydro-2H-[1,4]oxazin-3-yl)-4-fluoro-phenyl]-amide,
5-Furan-2-yl-pyridine-2-carboxylic acid [3-((RS)-5-amino-3-methyl-3,6-dihydro-2H-[1,4]oxazin-3-yl)-4-fluoro-phenyl]-amide,
5-Pyrrolidin-1-yl-pyridine-2-carboxylic acid [3-((RS)-5-amino-3-methyl-3,6-dihydro-2H-[1,4]oxazin-3-yl)-4-fluoro-phenyl]-amide,
5-Thiophen-2-yl-isoxazole-3-carboxylic acid [3-((RS)-5-amino-3-methyl-3,6-dihydro-2H-[1,4]oxazin-3-yl)-4-fluoro-phenyl]-amide,
(RS)-N-[3-(5-Amino-3-methyl-3,6-dihydro-2H-[1,4]oxazin-3-yl)-4-fluoro-phenyl]-3,3,3-trifluoro-propionamide,
Oxazole-2-carboxylic acid [3-((R)-5-amino-3-methyl-3,6-dihydro-2H-[1,4]oxazin-3-yl)-4-fluoro-phenyl]-amide,
5-Trifluoromethyl-pyrazine-2-carboxylic acid [3-((R)-5-amino-3-methyl-3,6-dihydro-2H-[1,4]oxazin-3-yl)-4-fluoro-phenyl]-amide,
5-Trifluoromethyl-pyrimidine-2-carboxylic acid [3-((R)-5-amino-3-methyl-3,6-dihydro-2H-[1,4]oxazin-3-yl)-4-fluoro-phenyl]-amide,
N-[3-((R)-5-Amino-3-methyl-3,6-dihydro-2H-[1,4]oxazin-3-yl)-4-fluoro-phenyl]-2,2,3,3-tetrafluoro-propionamide,
N-[3-((R)-5-Amino-3-methyl-3,6-dihydro-2H-[1,4]oxazin-3-yl)-4-fluoro-phenyl]-2-methoxy-acetamide,
(RS)-N-[3-((R)-5-Amino-3-methyl-3,6-dihydro-2H-[1,4]oxazin-3-yl)-4-fluoro-phenyl]-3,3,3-trifluoro-2-[(RS)-1-(tetrahydro-furan-2-yl)methyl]-propionamide,
1-Methoxymethyl-cyclopropanecarboxylic acid the 1-methoxymethyl-cyclopropanecarboxylic acid [3-((R)-5-amino-3-methyl-3,6-dihydro-2H-[1,4]oxazin-3-yl)-4-fluoro-phenyl]-amide,
(RS)-N-[3-((R)-5-Amino-3-methyl-3,6-dihydro-2H-[1,4]oxazin-3-yl)-4-fluoro-phenyl]-2-fluoro-propionamide,
N-[3-((R)-5-Amino-3-methyl-3,6-dihydro-2H-[1,4]oxazin-3-yl)-4-fluoro-phenyl]-isobutyramide,
(RS)-N-[3-((R)-5-Amino-3-methyl-3,6-dihydro-2H-[1,4]oxazin-3-yl)-4-fluoro-phenyl]-2-fluoro-propionamide,
N-[3-((R)-5-Amino-3-methyl-3,6-dihydro-2H-[1,4]oxazin-3-yl)-4-fluoro-phenyl]-2,2-difluoro-propionamide,
N-[3-((R)-5-Amino-3-methyl-3,6-dihydro-2H-[1,4]oxazin-3-yl)-4-fluoro-phenyl]-2,2-difluoro-acetamide,
(R)-N-(3-(5-Amino-3-methyl-3,6-dihydro-2H-1,4-oxazin-3-yl)-4-fluorophenyl)-2-fluoro-2-methylpropanamide,
N-[3-((R)-5-Amino-3-methyl-3,6-dihydro-2H-[1,4]oxazin-3-yl)-4-fluoro-phenyl]-acetamide,
N-[3-((R)-5-Amino-3-methyl-3,6-dihydro-2H-[1,4]oxazin-3-yl)-4-fluoro-phenyl]-propionamide,
N-[3-((R)-5-Amino-3-methyl-3,6-dihydro-2H-[1,4]oxazin-3-yl)-4-fluoro-phenyl]-3-methyl-butyramide,
(RS)-Tetrahydro-furan-3-carboxylic acid [3-((R)-5-amino-3-methyl-3,6-dihydro-2H-[1,4]oxazin-3-yl)-4-fluoro-phenyl]-amide,
N-[3-((R)-5-Amino-3-methyl-3,6-dihydro-2H-[1,4]oxazin-3-yl)-4-fluoro-phenyl]-formamide,
5-Chloro-3-methyl-pyridine-2-carboxylic acid [3-((R)-5-amino-3-methyl-3,6-dihydro-2H-[1,4]oxazin-3-yl)-4-fluoro-phenyl]-amide, and
5-Fluoro-pyridine-2-carboxylic acid [3-((R)-5-amino-3-methyl-3,6-dihydro-2H-[1,4]oxazin-3-yl)-4-fluoro-phenyl]-amide,
or pharmaceutically acceptable salts thereof.

One embodiment of the invention is a compound of formula I or Ix selected from the group consisting of
5-Chloro-pyridine-2-carboxylic acid [3-((R)-5-amino-3-methyl-3,6-dihydro-2H-[1,4]oxazin-3-yl)-4-fluoro-phenyl]-amide,
5-Chloro-pyridine-2-carboxylic acid [3-(5-amino-3-cyclopropyl-3,6-dihydro-2H-[1,4]oxazin-3-yl)-4-fluoro-phenyl]-amide,
5-Chloro-pyridine-2-carboxylic acid [3-((3R,6R) and (3S,6S)-5-amino-6-benzyl-3-methyl-3,6-dihydro-2H-[1,4]oxazin-3-yl)-4-fluoro-phenyl]-amide,
5-Chloro-pyridine-2-carboxylic acid [3-((3R,6S)- and (3S,6R)-5-amino-6-benzyl-3-methyl-3,6-dihydro-2H-[1,4]oxazin-3-yl)-4-fluoro-phenyl]-amide, 3,5-Dichloro-pyridine-2-carboxylic acid [3-((R)-5-amino-3-methyl-3,6-dihydro-2H-[1,4]oxazin-3-yl)-4-fluoro-phenyl]-amide,
1-Difluoromethyl-1H-pyrazole-3-carboxylic acid [3-((R)-5-amino-3-methyl-3,6-dihydro-2H-[1,4]oxazin-3-yl)-4-fluoro-phenyl]-amide,
1-Difluoromethyl-1H-pyrazole-3-carboxylic acid [3-((R)-5-amino-3-methyl-3,6-dihydro-2H-[1,4]oxazin-3-yl)-4-fluoro-phenyl]-amide,
5-Chloro-pyridine-2-carboxylic acid [3-((R)-5-amino-2,2,3-trimethyl-3,6-dihydro-2H-[1,4]oxazin-3-yl)-4-fluoro-phenyl]-amide,
5-(2,2,2-Trifluoro-ethoxy)-pyridine-2-carboxylic acid [3-((R)-5-amino-2,2,3-trimethyl-3,6-dihydro-2H-[1,4]oxazin-3-yl)-4-fluoro-phenyl]-amide,
5-Chloro-pyridine-2-carboxylic acid [3-((R)-5-amino-3,6,6-trimethyl-3,6-dihydro-2H-[1,4]oxazin-3-yl)-phenyl]-amide,
3-Chloro-5-cyano-pyridine-2-carboxylic acid [3-((R)-5-amino-3-methyl-3,6-dihydro-2H-[1,4]oxazin-3-yl)-4-fluoro-phenyl]-amide,
5-Cyano-pyridine-2-carboxylic acid [3-((R)-5-amino-3-methyl-3,6-dihydro-2H-[1,4]oxazin-3-yl)-4-fluoro-phenyl]-amide,
5-Difluoromethoxy-pyridine-2-carboxylic acid [3-((R)-5-amino-3-methyl-3,6-dihydro-2H-[1,4]oxazin-3-yl)-4-fluoro-phenyl]-amide, and
5-Chloro-3-fluoro-pyridine-2-carboxylic acid [3-((R)-5-amino-3-methyl-3,6-dihydro-2H-[1,4]oxazin-3-yl)-4-fluoro-phenyl]-amide,
or pharmaceutically acceptable salts thereof.

One embodiment of the invention is a compound of formula I or Ix selected from the group consisting of
1-(2,2,2-Trifluoro-ethyl)-1H-pyrazole-3-carboxylic acid [3-(5-amino-3-methyl-3,6-dihydro-2H-[1,4]oxazin-3-yl)-phenyl]-amide,
1-Methyl-1H-indazole-3-carboxylic acid [3-(5-amino-3-methyl-3,6-dihydro-2H-[1,4]oxazin-3-yl)-phenyl]-amide,
2,5-Dimethyl-furan-3-carboxylic acid [3-(5-amino-3-methyl-3,6-dihydro-2H-[1,4]oxazin-3-yl)-phenyl]-amide,
2,5-Dimethyl-oxazole-4-carboxylic acid [3-(5-amino-3-methyl-3,6-dihydro-2H-[1,4]oxazin-3-yl)-phenyl]-amide,
2,5-Dimethyl-thiophene-3-carboxylic acid [3-(5-amino-3-methyl-3,6-dihydro-2H-[1,4]oxazin-3-yl)-phenyl]-amide,
2-Methyl-oxazole-4-carboxylic acid [3-(5-amino-3-methyl-3,6-dihydro-2H-[1,4]oxazin-3-yl)-phenyl]-amide,
2-Methyl-thiazole-4-carboxylic acid [3-(5-amino-3-methyl-3,6-dihydro-2H-[1,4]oxazin-3-yl)-phenyl]-amide,
3,5-Dichloro-pyridine-2-carboxylic acid [3-(5-amino-3-methyl-3,6-dihydro-2H-[1,4]oxazin-3-yl)-phenyl]-amide,
3,5-Difluoro-pyridine-2-carboxylic acid [3-(5-amino-3-methyl-3,6-dihydro-2H-[1,4]oxazin-3-yl)-phenyl]-amide,
3-Chloro-5-trifluoromethyl-pyridine-2-carboxylic acid [3-(5-amino-3-methyl-3,6-dihydro-2H-[1,4]oxazin-3-yl)-phenyl]-amide,
5-(2,2,2-Trifluoro-ethoxy)-pyridine-2-carboxylic acid [3-(5-amino-3-cyclopropyl-3,6-dihydro-2H-[1,4]oxazin-3-yl)-4-fluoro-phenyl]-amide,
5-(2,2,2-Trifluoro-ethoxy)-pyridine-2-carboxylic acid [3-(5-amino-3-methyl-3,6-dihydro-2H-[1,4]oxazin-3-yl)-phenyl]-amide hydrochloride,
5-Chloro-pyridine-2-carboxylic acid [3-((R)-5-amino-3-methyl-3,6-dihydro-2H-[1,4]oxazin-3-yl)-phenyl]-amide,
5-Chloro-pyridine-2-carboxylic acid [3-((R)-5-amino-3-methyl-3,6-dihydro-2H-[1,4]oxazin-3-yl)-4-fluoro-phenyl]-amide,
5-Chloro-pyridine-2-carboxylic acid [3-(5-amino-3-cyclopropyl-3,6-dihydro-2H-[1,4]oxazin-3-yl)-4-fluoro-phenyl]-amide,
5-Chloro-pyridine-2-carboxylic acid [3-(5-amino-3-methyl-3,6-dihydro-2H-[1,4]oxazin-3-yl)-phenyl]-amide,
5-Chloro-pyridine-2-carboxylic acid [3-(5-amino-3-methyl-3,6-dihydro-2H-[1,4]oxazin-3-yl)-4-fluoro-phenyl]-amide,
5-Chloro-thiophene-2-carboxylic acid [3-(5-amino-3-methyl-3,6-dihydro-2H-[1,4]oxazin-3-yl)-phenyl]-amide,
N-[3-(5-Amino-3-methyl-3,6-dihydro-2H-[1,4]oxazin-3-yl)-4-fluoro-phenyl]-2,2,3,3,3-pentafluoro-propionamide,
N-[3-(5-Amino-3-methyl-3,6-dihydro-2H-[1,4]oxazin-3-yl)-4-fluoro-phenyl]-4-chloro-thiobenzamide,
N-[3-(5-Amino-3-methyl-3,6-dihydro-2H-[1,4]oxazin-3-yl)-phenyl]-4-chloro-2-fluoro-benzamide,
N-[3-(5-Amino-3-methyl-3,6-dihydro-2H-[1,4]oxazin-3-yl)-phenyl]-2,4-dichloro-benzamide,
N-[3-(5-Amino-3-methyl-3,6-dihydro-2H-[1,4]oxazin-3-yl)-phenyl]-2,5-difluoro-benzamide,
N-[3-(5-Amino-3-methyl-3,6-dihydro-2H-[1,4]oxazin-3-yl)-phenyl]-3-chloro-benzamide,
N-[3-(5-Amino-3-methyl-3,6-dihydro-2H-[1,4]oxazin-3-yl)-phenyl]-4-chloro-2-iodo-benzamide,
N-[3-(5-Amino-3-methyl-3,6-dihydro-2H-[1,4]oxazin-3-yl)-4-fluoro-phenyl]-4-chloro-benzamide,
Pyrazine-2-carboxylic acid [3-(5-amino-3-methyl-3,6-dihydro-2H-[1,4]oxazin-3-yl)-phenyl]-amide hydrochloride and
Pyrazolo[1,5-a]pyridine-2-carboxylic acid [3-(5-amino-3-methyl-3,6-dihydro-2H-[1,4]oxazin-3-yl)-phenyl]-amide,
or pharmaceutically acceptable salts thereof.

One embodiment of the invention is a compound of formula I or Ix selected from the group consisting of 5-Chloro-pyridine-2-carboxylic acid [3-(5-amino-3-methyl-3,6-dihydro-2H-[1,4]oxazin-3-yl)-4-fluoro-phenyl]-amide and 5-Chloro-pyridine-2-carboxylic acid [3-((R)-5-amino-3-methyl-3,6-dihydro-2H-[1,4]oxazin-3-yl)-4-fluoro-phenyl]-amide,
or pharmaceutically acceptable salts thereof.

One embodiment of the invention is a process for preparing a compound of formula Ix as defined in the embodiments, which process comprises amination of a compound of formula XXII,

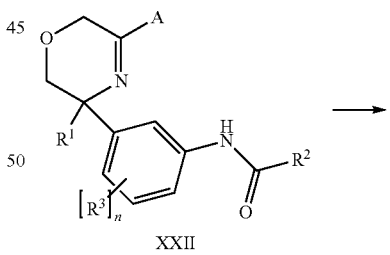

XXII

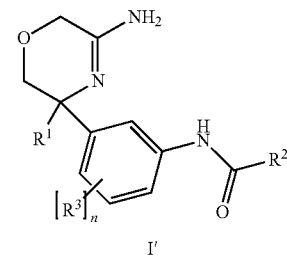

I' to a compound of formula I', which compound of formula I' can optionally further react with a thiation agent to the corresponding compound of formula I"

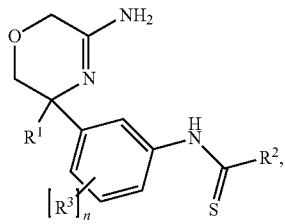

wherein $R^1$, $R^2$, $R^3$ are as defined in the embodiments and A is lower alkoxy.

One embodiment of the invention is a compound of formula Ix, whenever prepared by a process as defined above.

One embodiment of the invention is a compound of formula Ix, obtainable by a process as defined above.

One embodiment of the invention is a compound of formula I or Ix as defined in any of the embodiments, for use as therapeutically active substance.

One embodiment of the invention is a compound of formula I or Ix as defined in any of the embodiments, for the use as inhibitor of BACE1 and/or BACE2 activity.

One embodiment of the invention is a compound of formula I or Ix as defined in any of the embodiments, for the use in inhibition of BACE1 activity.

One embodiment of the invention is a compound of formula I or Ix as defined in any of the embodiments, for the use in inhibition of BACE2 activity.

One embodiment of the invention is a compound of formula I or Ix as defined in any of the embodiments, for the use in inhibition of BACE1 and BACE2 activity.

One embodiment of the invention is a compound of formula I or Ix as defined in any of the embodiments, for the use in inhibition of BACE1 or BACE2 activity.

One embodiment of the invention is a compound of formula I or Ix as defined in any of the embodiments, for the use as therapeutically active substance for the therapeutic and/or prophylactic treatment of diseases and disorders characterized by elevated β-amyloid levels and/or β-amyloid oligomers and/or β-amyloid plaques and further deposits, particularly Alzheimer's disease.

One embodiment of the invention is a compound of formula I or Ix as defined in any of the embodiments, for the use as therapeutically active substance for the therapeutic and/or prophylactic treatment of Alzheimer's disease.

One embodiment of the invention is a compound of formula I or Ix as defined in any of the embodiments, for the use as therapeutically active substance for the therapeutic and/or prophylactic treatment of diabetes, particularly type 2 diabetes.

One embodiment of the invention is a compound of formula I or Ix as defined in any of the embodiments, for the use as therapeutically active substance for the therapeutic and/or prophylactic treatment of type 2 diabetes.

One embodiment of the invention is a compound of formula I or Ix as defined in any of the embodiments, for the use as therapeutically active substance for the therapeutic and/or prophylactic treatment of amyotrophic lateral sclerosis (ALS), arterial thrombosis, autoimmune/inflammatory diseases, cancer such as breast cancer, cardiovascular diseases such as myocardial infarction and stroke, dermatomyositis, Down's Syndrome, gastrointestinal diseases, Glioblastoma multiforme, Graves Disease, Huntington's Disease, inclusion body myositis (IBM), inflammatory reactions, Kaposi Sarcoma, Kostmann Disease, lupus erythematosus, macrophagic myofasciitis, juvenile idiopathic arthritis, granulomatous arthritis, malignant melanoma, multiple mieloma, rheumatoid arthritis, Sjogren syndrome, SpinoCerebellar Ataxia 1, SpinoCerebellar Ataxia 7, Whipple's Disease or Wilson's Disease.

One embodiment of the invention is a pharmaceutical composition comprising a compound as defined in any of the embodiments as an active ingredient and a pharmaceutically acceptable carrier and/or a pharmaceutically acceptable auxiliary substance.

One embodiment of the invention is the use of a compound as defined in any of the embodiments for the manufacture of a medicament for the therapeutic and/or prophylactic treatment of diseases and disorders characterized by elevated β-amyloid levels and/or β-amyloid oligomers and/or β-amyloid plaques and further deposits, particularly Alzheimer's disease.

One embodiment of the invention is the use of a compound as defined in any of the embodiments for the manufacture of a medicament for the therapeutic and/or prophylactic treatment of Alzheimer's disease.

One embodiment of the invention is the use of a compound as defined in any of the embodiments for the manufacture of a medicament for the therapeutic and/or prophylactic treatment of diabetes, particularly type 2 diabetes.

One embodiment of the invention is the use of a compound as defined in any of the embodiments for the manufacture of a medicament for the therapeutic and/or prophylactic treatment of type 2 diabetes.

One embodiment of the invention is the use of a compound as defined in any of the embodiments for the manufacture of a medicament for the therapeutic and/or prophylactic treatment of amyotrophic lateral sclerosis (ALS), arterial thrombosis, autoimmune/inflammatory diseases, cancer such as breast cancer, cardiovascular diseases such as myocardial infarction and stroke, dermatomyositis, Down's Syndrome, gastrointestinal diseases, Glioblastoma multiforme, Graves Disease, Huntington's Disease, inclusion body myositis (IBM), inflammatory reactions, Kaposi Sarcoma, Kostmann Disease, lupus erythematosus, macrophagic myofasciitis, juvenile idiopathic arthritis, granulomatous arthritis, malignant melanoma, multiple mieloma, rheumatoid arthritis, Sjogren syndrome, SpinoCerebellar Ataxia 1, SpinoCerebellar Ataxia 7, Whipple's Disease or Wilson's Disease.

One embodiment of the invention is the use of a compound as defined in any of the embodiments for the use in inhibition of BACE1 and/or BACE2 activity.

One embodiment of the invention is the use of a compound as defined in any of the embodiments for the use in inhibition of BACE1 activity.

One embodiment of the invention is the use of a compound as defined in any of the embodiments for the use in inhibition of BACE2 activity.

One embodiment of the invention is the use of a compound as defined in any of the embodiments for the use in inhibition of BACE1 and BACE2 activity.

One embodiment of the invention is the use of a compound as defined in any of the embodiments for the use in inhibition of BACE1 or BACE2 activity.

One embodiment of the invention is the use of a compound as defined in any of the embodiments for the therapeutic and/or prophylactic treatment of diseases and disorders characterized by elevated β-amyloid levels and/or β-amyloid oligomers and/or β-amyloid plaques and further deposits, particularly Alzheimer's disease.

One embodiment of the invention is the use of a compound as defined in any of the embodiments for the therapeutic and/or prophylactic treatment of Alzheimer's disease.

One embodiment of the invention is the use of a compound as defined in any of the embodiments for the therapeutic and/or prophylactic treatment of diabetes, particularly type 2 diabetes.

One embodiment of the invention is the use of a compound as defined in any of the embodiments for the therapeutic and/or prophylactic treatment of type 2 diabetes.

One embodiment of the invention is the use of a compound as defined in any of the embodiments for the therapeutic and/or prophylactic treatment of amyotrophic lateral sclerosis (ALS), arterial thrombosis, autoimmune/inflammatory diseases, cancer such as breast cancer, cardiovascular diseases such as myocardial infarction and stroke, dermatomyositis, Down's Syndrome, gastrointestinal diseases, Glioblastoma multiforme, Graves Disease, Huntington's Disease, inclusion body myositis (IBM), inflammatory reactions, Kaposi Sarcoma, Kostmann Disease, lupus erythematosus, macrophagic myofasciitis, juvenile idiopathic arthritis, granulomatous arthritis, malignant melanoma, multiple mieloma, rheumatoid arthritis, Sjogren syndrome, SpinoCerebellar Ataxia 1, SpinoCerebellar Ataxia 7, Whipple's Disease or Wilson's Disease.

One embodiment of the invention is a method for the use in inhibition of BACE1 and/or BACE2 activity, which method comprises administering a compound as defined in any of the embodiments to a human being or animal.

One embodiment of the invention is a method for the use in inhibition of BACE1 activity, which method comprises administering a compound as defined in any of the embodiments to a human being or animal.

One embodiment of the invention is a method for the use in inhibition of BACE2 activity, which method comprises administering a compound as defined in any of the embodiments to a human being or animal.

One embodiment of the invention is a method for the use in inhibition of BACE1 and BACE2 activity, which method comprises administering a compound as defined in any of the embodiments to a human being or animal.

One embodiment of the invention is a method for the use in inhibition of BACE1 or BACE2 activity, which method comprises administering a compound as defined in any of the embodiments to a human being or animal.

One embodiment of the invention is a method for the use in inhibition of BACE1 and/or BACE2 activity, particularly for the therapeutic and/or prophylactic treatment of diseases and disorders characterized by elevated β-amyloid levels and/or β-amyloid oligomers and/or A amyloid plaques and further deposits, Alzheimer's disease, diabetes or type 2 diabetes, which method comprises administering a compound of formula I according to any of the embodiments to a human being or animal.

One embodiment of the invention is a method for the use in inhibition of BACE1 and/or BACE2 activity, particularly for the therapeutic and/or prophylactic treatment of amyotrophic lateral sclerosis (ALS), arterial thrombosis, autoimmune/inflammatory diseases, cancer such as breast cancer, cardiovascular diseases such as myocardial infarction and stroke, dermatomyositis, Down's Syndrome, gastrointestinal diseases, Glioblastoma multiforme, Graves Disease, Huntington's Disease, inclusion body myositis (IBM), inflammatory reactions, Kaposi Sarcoma, Kostmann Disease, lupus erythematosus, macrophagic myofasciitis, juvenile idiopathic arthritis, granulomatous arthritis, malignant melanoma, multiple mieloma, rheumatoid arthritis, Sjogren syndrome, SpinoCerebellar Ataxia 1, SpinoCerebellar Ataxia 7, Whipple's Disease or Wilson's Disease.

Furthermore, the invention includes all optical isomers, i.e. diastereoisomers, diastereomeric mixtures, racemic mixtures, all their corresponding enantiomers and/or tautomers as well as their solvates.

The compounds of formula I can contain one or more asymmetric centers and can therefore occur as racemates, racemic mixtures, single enantiomers, diastereomeric mixtures and individual diastereomers. Additional asymmetric centers can be present depending upon the nature of the various substituents on the molecule. Each such asymmetric centre will independently produce two optical isomers and it is intended that all of the possible optical isomers and diastereomers in mixtures and as pure or partially purified compounds are included within this invention. The present invention is meant to encompass all such isomeric forms of these compounds. The independent syntheses of these diastereomers or their chromatographic separations can be achieved as known in the art by appropriate modification of the methodology disclosed herein. Their absolute stereochemistry can be determined by the x-ray crystallography of crystalline products or crystalline intermediates which are derivatized, if necessary, with a reagent containing an asymmetric centre of known absolute configuration. If desired, racemic mixtures of the compounds can be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. Preferred examples of isomers of a compound of formula I is a compound of formula Ia, Ib, Ic or Id, wherein the residues have the meaning as described in the embodiments. Preferred are compounds of formula Ib or Id.

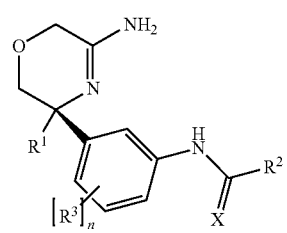

Ia

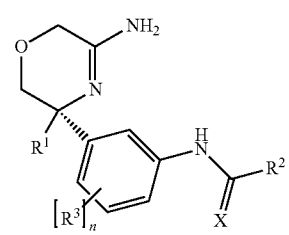

Ib

Ic

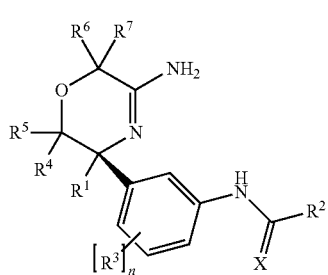

Id

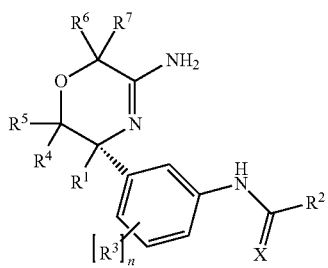

In the embodiments, where optically pure enantiomers are provided, optically pure enantiomer means that the compound contains >90% of the desired isomer by weight, preferably >95% of the desired isomer by weight, or more preferably >99% of the desired isomer by weight, said weight percent based upon the total weight of the isomer(s) of the compound. Chirally pure or chirally enriched compounds can be prepared by chirally selective synthesis or by separation of enantiomers. The separation of enantiomers can be carried out on the final product or alternatively on a suitable intermediate.

A compound of formula I can also be present in its respective tautomeric form.

The compounds of formula I can be prepared in accordance with the following schemes. The starting material is commercially available or can be prepared in accordance with known methods. Any previously defined residues and variables will continue to have the previously defined meaning unless otherwise indicated.

The compounds of formula I can be prepared through a number of synthetic routes for example as illustrated in schemes 1-4. The preparation of compounds of formula I of the present invention can be carried out in sequential or convergent synthetic routes. Syntheses of the compounds of the invention are shown in the following schemes 1-4. The skills required for carrying out the reaction and purification of the resulting products are known to those skilled in the art. The substituents and indices used in the following description of the processes have the significance given herein before unless indicated to the contrary.

In more detail, the compounds of formula I can be manufactured by the methods given below, by the methods given in the examples or by analogous methods. Appropriate reaction conditions for the individual reaction steps are known to a person skilled in the art. The reaction sequence is not limited to the one displayed in schemes described below, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

The compounds of formula I described in the schemes 1-4 can be isolated and purified by methods known to those skilled in the art, such as but not limited to ion exchange chromatography, solid phase extraction, liquid-liquid extraction, silica chromatography, crystallization and preparative HPLC.

According to scheme 1, ketones of general formula IV (wherein Y has the meaning of a leaving group like halogen, e.g. bromide) can be reacted with cyanides, like potassium cyanide, together with ammonium carbonate in polar solvents such as alcohols, e.g. ethanol, water or tetrahydrofuran and mixtures thereof, to form hydantoins of formula V. The hydantoin can then be treated with water along with a base such as sodium hydroxide or a strong acid such as sulfuric acid at temperatures ranging from ambient temperature to reflux to yield the amino acid of formula VI. The amino alcohol of formula VIII is obtained by esterification of the acid of formula VI with a lower alcohol, such as methanol or ethanol, followed by reduction of the resulting amino ester of formula VII with lithium aluminum hydride or other suitable reagents both steps performed under conditions known to those skilled in the art. N-Acylation of the aminoalcohol of formula VIII can be effected by condensation with halogenated acetic acid derivatives, such as chloroacetic acid using condensation reagents like benzotriazole derivatives, e.g. O-(benzotriazol-1-yl)-N,N,N',N'-tetramethyluronium-hexafluorophosphate (HBTU) and the like in inert solvents, or with acid chloride derivatives such as chloroacetyl chloride in presence of a base such as triethylamine in an inert solvent both methods under conditions known to those skilled in the art and yielding acetyl derivatives of formula IX. Lactams of formula X can be prepared by cyclization of the alcohol of formula IX with base, such as potassium tent-butylate, in solvents such as tent-butanol at temperatures ranging from room temperature to reflux. The iminoether of formula XI can be synthesized by treatment of the lactam of formula X with alkyl oxonium salts, e.g. trimethyloxonium tetrafluoroborate or triethyloxonium tetrafluoroborate. Non commercial ketones of general formula IV can be synthesized by routes such as depicted in scheme 1 or by other routes known to those skilled in the art. Weinreb amides of formula III can be obtained by standard condensation reactions of the acids of formula II with N,O-dimethylhydroxylamine or by the intermediate formation of the acyl chloride of acids of formula II using an agent such as oxalyl chloride or thionyl chloride using standard conditions such as triethylamine/dichloromethane. The amides of formula III can be reacted with organometallics such as methylmagnesium chloride in inert aprotic solvents such as tetrahydrofuran or diethyl ether to yield the desired ketones of formula IV.

Scheme 1: Synthesis of intermediate ethers XI

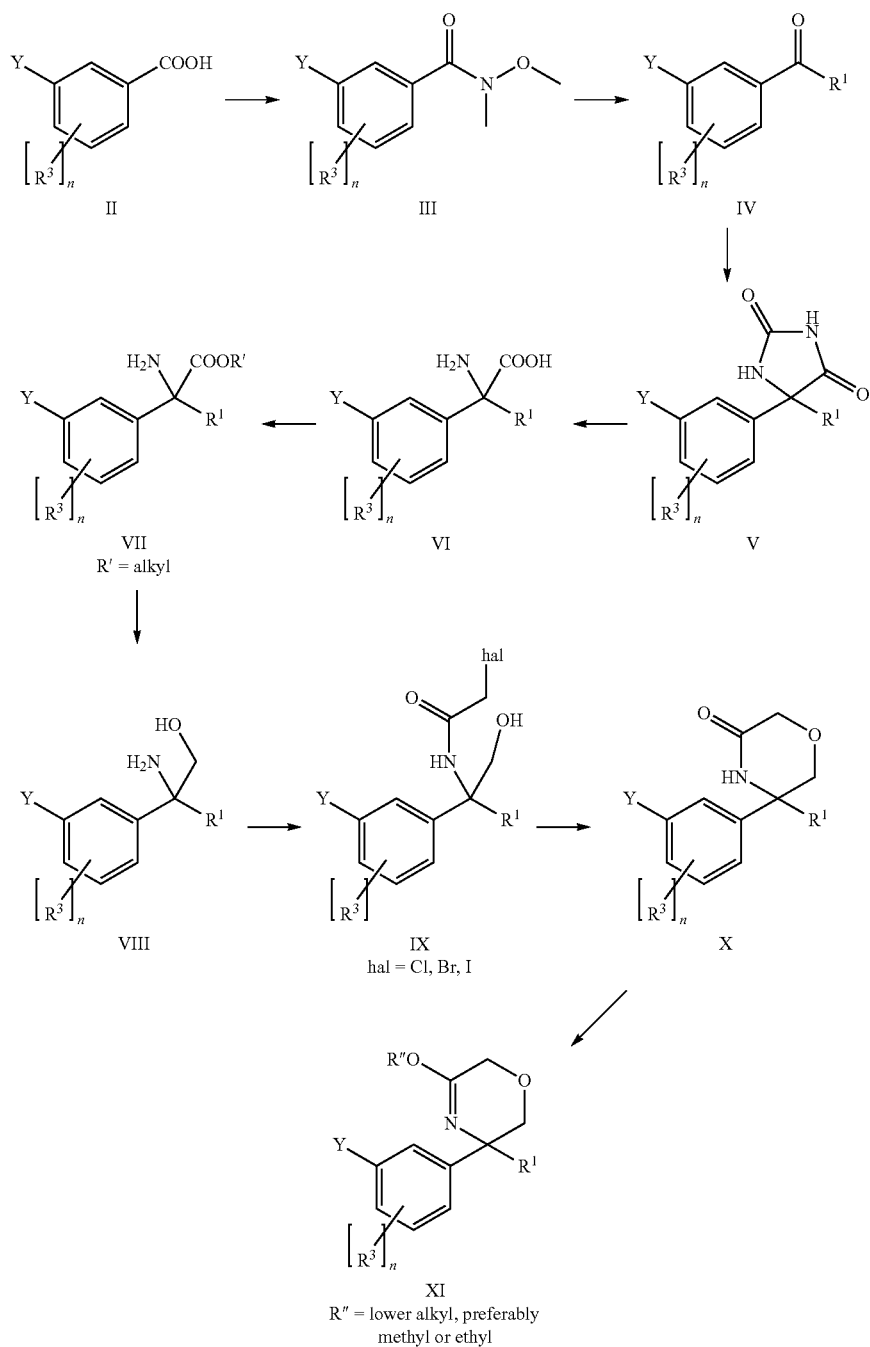

For the further transformation to the aniline derivative of formula XIII, Pd(0)-catalyzed amination reactions of aryl halides can be applied wherein as ammonia equivalents lithium bis(trimethylsilyl)amide, triphenylsilylamine, or benzophenone imine are used as described in the art (Organic Letters, 2001, 3(21), 3417-3419 or Bioorganic & Medicinal Chemistry Letters 14 (2004), 6011-6016). In scheme 2, the reaction leading to the benzophenone imine derivative of formula XII is exemplified as well as its cleavage under acidic conditions to yield the aniline derivative XIII.

The synthesis of amides of formula XIV can be performed by standard procedures, such as e.g. by reaction with activated acyl derivatives, e.g. acyl halides or anhydrides, or by condensation reactions of the acid using as condensation reagent carbodiimides, e.g. 1-(3-dimethylaminopropyl)-3-ethylcarbodiimide, or benzotriazole derivatives, e.g. O-(benzotriazol-1-yl)-N,N,N',N'-tetramethyluronium-hexafluorophosphate (HBTU) and the like.

The iminoether of formula XV can be obtained by treatment of the lactam of formula XIV with alkyl oxonium salts, e.g. trimethyloxonium tetrafluoroborate or triethyloxonium tetrafluoroborate.

Treatment of the iminoether of formula XV with ammonium salt such as ammonium chloride in polar solvents like alcohols, e.g. methanol yields the final compound of formula I'.

Scheme 2: Synthesis of compounds of formula I'

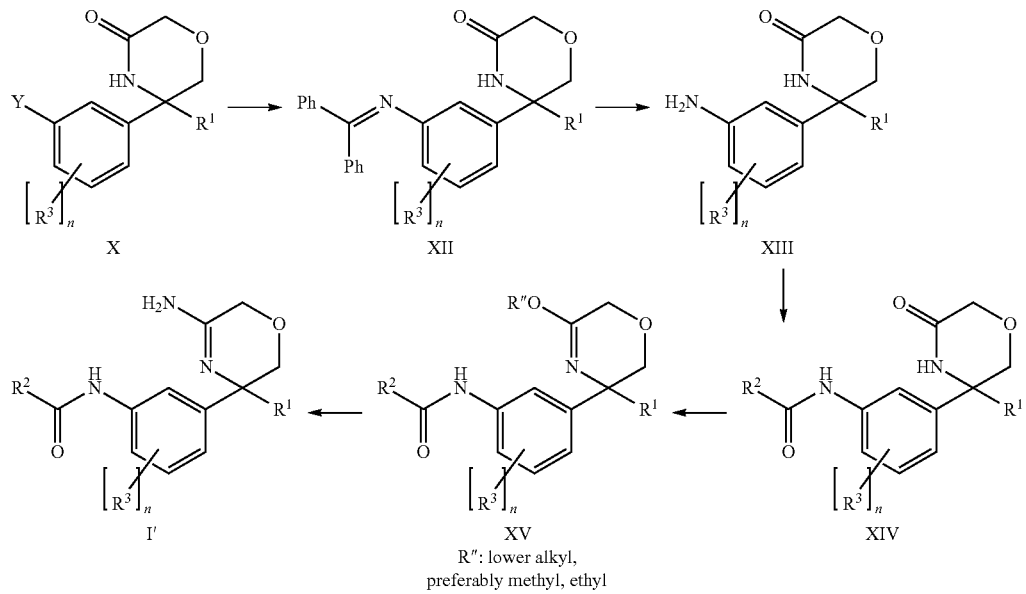

R": lower alkyl, preferably methyl, ethyl

Alternatively, compounds of formula I' can be obtained as follows: According to scheme 3, the formation of a methylt-riphenyl-phosphonium ylide produced by strong base such as butyllithium in solvents such as tetrahydrofuran or toluene at temperatures between −78° C. and 0° C. followed by addition of the ketone of formula IV yields the desired alkenes of formula XVI. The alkenes can then be reacted with a mixture of silver cyanate and iodine in solvents such as diethyl ether or mixtures of ethyl acetate and acetonitrile. The resultant iodo-isocyanates of formulas XVII can then be heated with alcohols like tert-butanol and a base like triethylamine or Huenig's base to yield the oxazolidinones of formula XVIII. Hydrolysis of the resultant oxazolidinone of formula XVIII with aqueous base like lithium hydroxide yields the aminoalcohol of formula VIII.

N-Acylation of the aminoalcohol of formula VIII can be effected by condensation with halogenated acetic acid derivatives, such as chloroacetic acid using condensation reagents like benzotriazole derivatives, e.g. O-(benzotriazol-1-yl)-N,N,N',N'-tetramethyluronium-hexa-fluorophosphate (HBTU) and the like in inert solvents, or with acid chloride derivatives such as chloroacetylchloride in presence of a base such as triethylamine in an inert solvent both methods under conditions known to those skilled in the art and yielding acetyl derivatives of formula IX. Lactams of formula X can be prepared by cyclization of the alcohol of formula IX with base, such as potassium tent-butylate, in solvents such as tert-butanol at temperatures ranging from room temperature to reflux.

For the further transformation, the benzophenone imine derivative of formula XII is treated with Lawesson's reagent under conditions known to those skilled in the art to yield the thiolactam of formula XIX. Cleavage of the benzophenone imine of formula XIX under acidic conditions to the aniline derivative XX followed by the synthesis of amides of formula XXI can be performed by standard procedures such as already described for scheme 2. Alternatively, the aniline derivative of formula XX can be obtained by treatment of the lactam of formula XIII (scheme 2) with Lawesson's reagent. Treatment of the thiolactam of formula XXI either with oxidizing reagents like tent-butyl hydroperoxide followed by ammonolysis or by treatment with ammonia in methanol alone yields the final compound of formula I'.

A more precise description of the conditions is given in the preparation of Building block E.

Scheme 3: Synthesis of compounds of formula I'

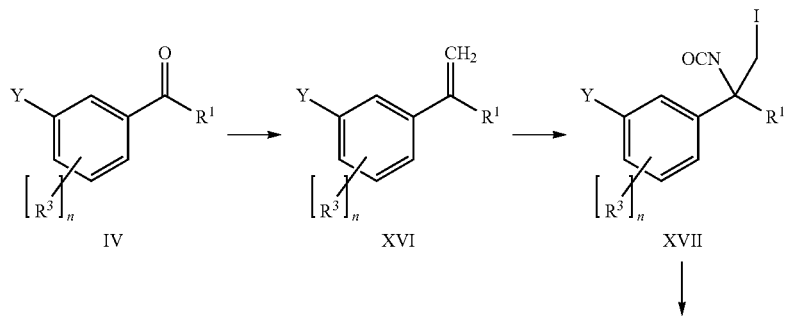

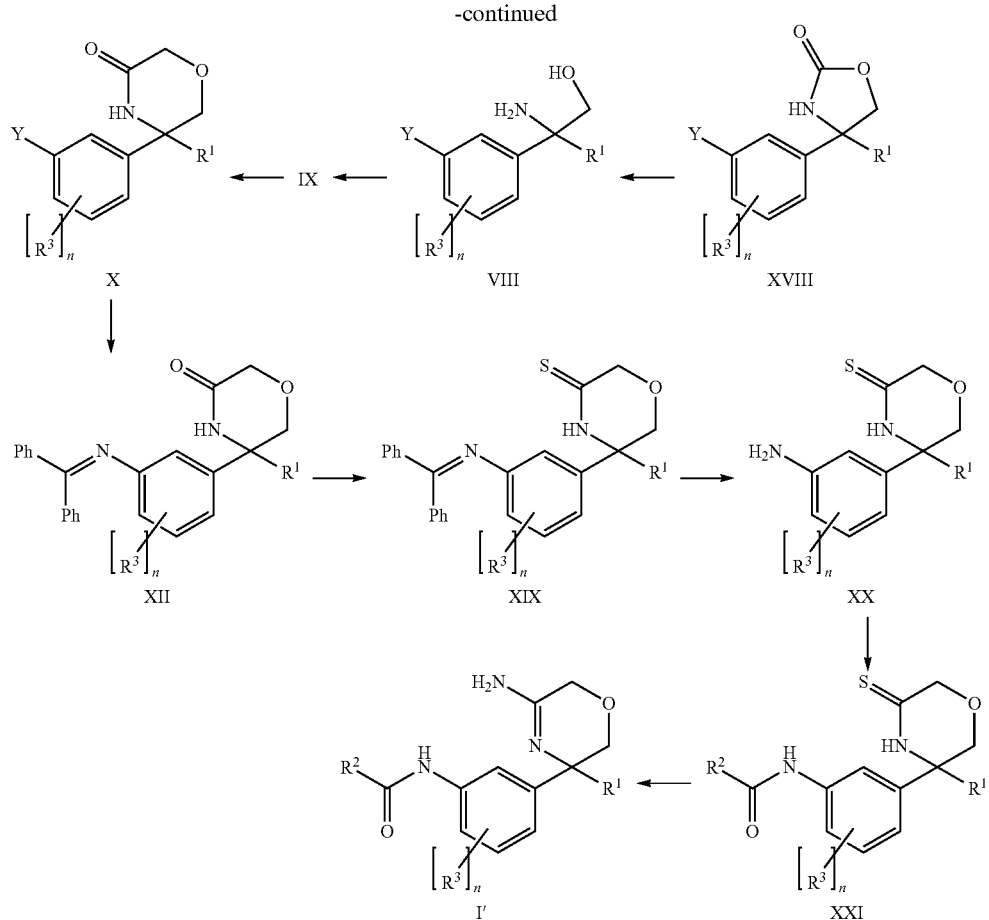
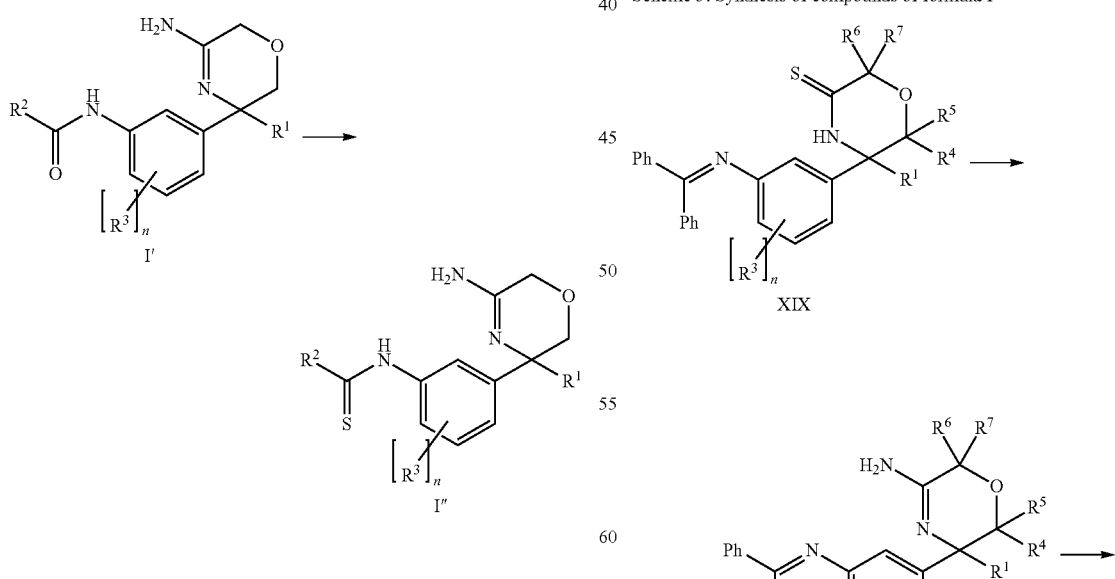
Scheme 4: Synthesis of compounds of formula I″
Scheme 5: Synthesis of compounds of formula I‴
Compounds of general formula I wherein X=S (I″) can be prepared by reaction of compounds of formula I' with a thiation agent like Lawesson's reagent under conditions known to those skilled in the art to yield the corresponding thioamides of formula I″.

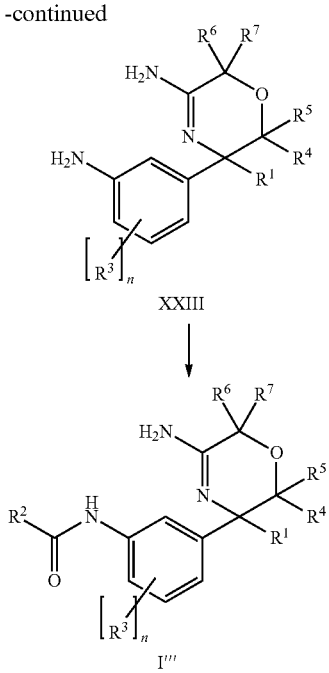

Compounds of formula I''' can be prepared as follows: Starting from the thiolactam of formula XIX the reaction with a solution of ammonia in a protic solvent such as methanol, ethanol or water, preferably methanol, with or without presence of a mild oxidant such as tert-butylhydroperoxide at temperatures between 0 and 60° C., preferably at 23° C. in the presence of an oxidant or at 50 to 60° C. in the absence of an oxidant.

The intermediate benzophenone imine of formula XXII can be hydrolyzed to the aniline of formula XXIII by aqueous mineral acid such as sulfuric acid or hydrochloric acid, preferably hydrochloric acid, in a solvent such as tetrahydrofuran, 1,2-dimethoxyethane or 1,4-dioxane, preferably 1,4-dioxane, at temperatures between 0 and 23° C., preferably at 23° C.

The selective condensation of anilines of formula XXIII with acids to compounds of formula I''' was achieved by the use of 4-(4,6-dimethoxy-1,3,5-triazin-2-yl)-4-methylmorpholinium chloride hydrate (DMTMM) as the condensating agent in a protic solvent such as methanol or ethanol, preferably methanol, at temperatures between 0 and 23° C., preferably at 4° C.

Scheme 6: Synthesis of compounds of formula I''''

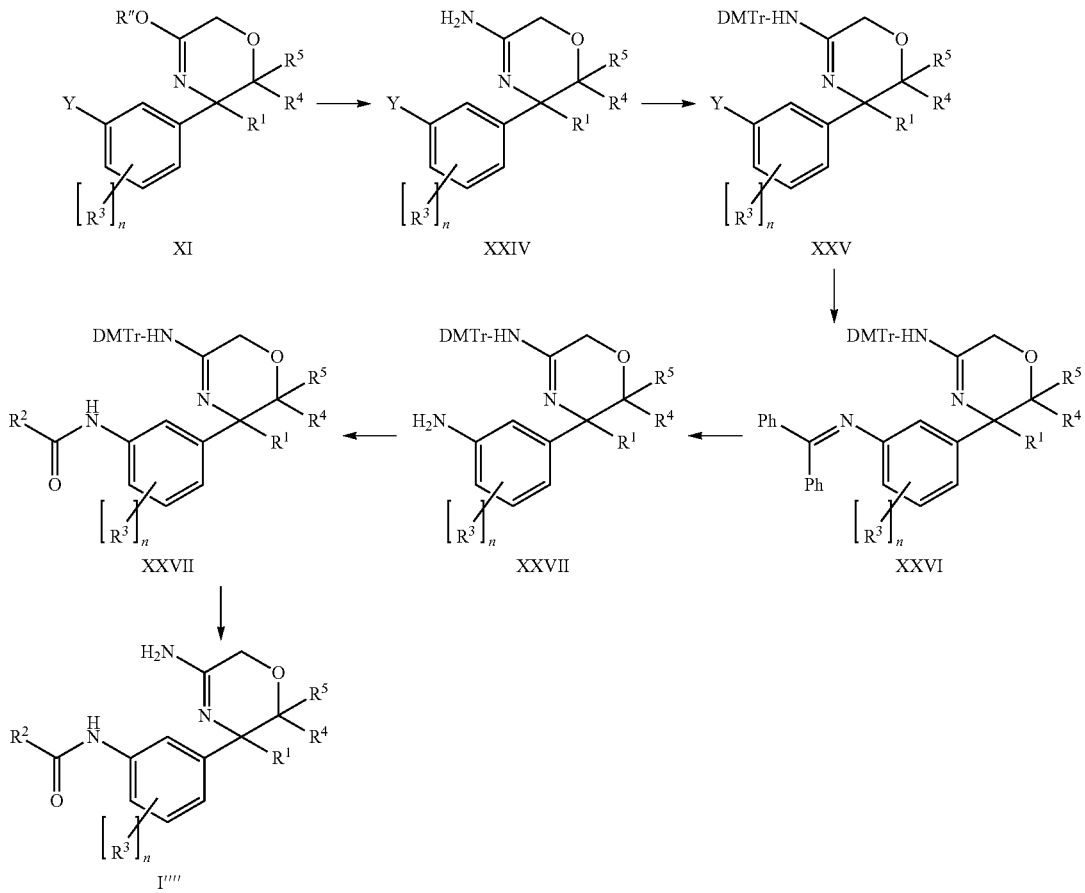

DMTr: 4,4'dimethoxytriphenylmethyl

Compounds of formula I'''' can also be prepared as follows: Starting from the iminoether of formula XI the treatment with ammonium salts such as ammonium chloride in a protic solvent like alcohols, preferably methanol, yields the amine of formula XXIV.

The intermediate amine of formula XXIV can be protected by groups like triphenylmethyl derivatives, preferably by 4,4'-dimethoxytriphenymethyl. The reaction can be performed in inert solvents, e.g. dichloromethane, at temperatures between 0° C. and room temperature to yield the N-protected amine of formula XXV.

The transformation into the aniline derivative of formula XXVII can be achieved by following the reaction sequence via the benzophenone imine derivative of formula XXVIII and its hydrolysis as described before.

The coupling of anilines of formula XXVII with acids to compounds of formula XXVIII can be achieved by appropriate coupling agents like carbodiimides or uronium salts, such as for example N,N'-carbonyldiimidazole (CDI), N,N'-dicyclohexylcarbodiimide (DCC), N-(3-dimethylaminopropyl)-N'-ethyl-carbodiimide-hydrochloride (EDCI), O-(benzotriazol-1-yl)-N,N,N',N'-tetramethyluronium tetrafluoroborate (TBTU) and 1-[bis(dimethylamino)methylene]-1H-1,2,3-triazolo[4,5-b]pyridinium-3-oxide hexafluorophosphate (HATU) under basic conditions, i.e. in the presence of a base, preferably an alkylamine such as diisopropylethylamine or triethylamine, or a tertiary amine such as N-methylmorpholine or 4-(dimethylamino)-pyridine. The reaction is carried out in a suitable solvent such as for example N,N-dimethylformamide (DMF), dimethylacetamide or dichloromethane, at temperatures between 0° C. and ambient temperature. Furthermore by using 4-(4,6-dimethoxy-1,3,5-triazin-2-yl)-4-methylmorpholinium chloride hydrate (DMTMM) as the condensating agent in a protic solvent such as methanol or ethanol, preferably methanol, at temperatures between 0 and 23° C., preferably at 4° C.

The N-protecting group in compounds of formula XXVIII can be cleaved by acids like trifluoroacetic acid in inert solvents, e.g. dichloromethane, at temperatures between 0 and 23° C. to yield compounds of formula I''''.

Scheme 7: Enantioselective synthesis of aminoalcohols of formula VIII and VIIIa.

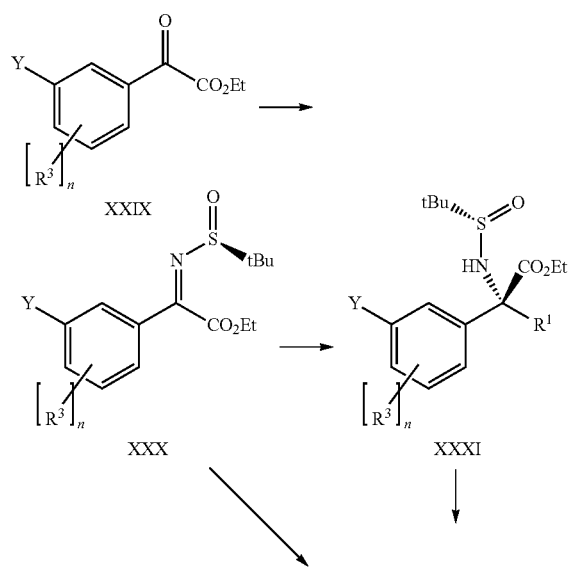

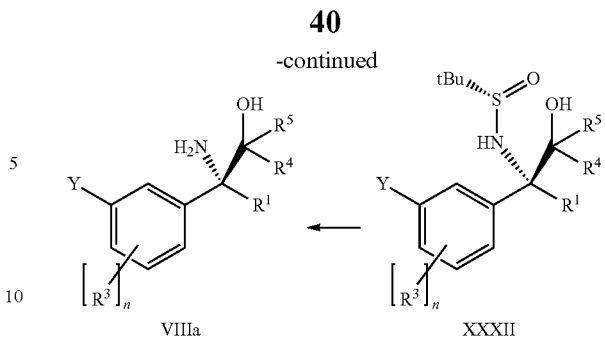

Compounds of the general formula VIIIa can be prepared in an enantioselective manner as follows: An alpha-ketoester of general formula XXIX can be converted into the sulfinyl imine of general formula XXX in analogy to T. P. Tang & J. A. Ellman, J. Org. Chem. 1999, 64, 12, by condensation of the aryl ketone group and a sulfinamide, e.g. an alkyl sulfinamide, in this case most preferably (S)-(−)-tert-butylsulfinamide in the presence of a Lewis acid such as e.g. a titanium(IV) alkoxide, more preferably titanium(IV) ethoxide in a solvent such as an ether, e.g. diethyl ether or more preferably tetrahydrofuran.

The conversion of the sulfinyl imine XXX to the ester of general formula XXXI or directly to the alcohols of general formula XXXII proceeds stereoselectively by the chiral directing group as described by Tang & Ellman.

The sulfinyl imine of general formula XXX can be treated with an organometallic reagent, e.g. an organolithium or Grignard-reagent, in a solvent such as an ether, e.g. diethyl ether or more preferably tetrahydrofuran, at temperatures starting from −78° C. and eventually raising to 23° C., to generate the esters of general formula XXXI.

These esters of general formula XXXI can in turn be treated with another organometallic reagent, e.g. an organolithium or Grignard-reagent, in a solvent such as an ether, e.g. diethyl ether or more preferably tetrahydrofuran, at temperatures starting from −78° C. and eventually raising to 23° C., to generate the alcohols of general formula XXXII, wherein $R^1$ can be different from $R^4$ and $R^5$.

Alternatively the esters of general formula XXXI can be reduced to the alcohols of general formula XXXII, wherein $R^4$ and $R^5$ are hydrogen, by reaction with a reducing agent such as e.g. lithium aluminum hydride or more preferably lithium borohydride in an ether solvent, like e.g. diethyl ether or more preferably tetrahydrofuran, at temperatures between 0 and 50° C., preferably at 23° C. to yield aminoalcohols VIII.

If compounds of general formula XXXII, wherein $R^1$, $R^4$ and $R^5$ are all of the same kind, are desired, the sulfinyl imine of general formula XXX can be treated with a large excess of an organometallic reagent, e.g. an organolithium or Grignard-reagent, in a solvent such as an ether, e.g. diethyl ether or more preferably tetrahydrofuran, at temperatures starting from −78° C. and eventually raising to 23° C., to directly generate the alcohols of general formula XXXII.

If compounds of general formula XXXII, wherein $R^1$, $R^4$ and $R^5$ are all of different kind, are desired, the sulfinyl imine of the Weinreb amide instead of the ethyl ester in general formula XXX (as described e.g. in Journal of Organic Chemistry (1995), 60(16), 5016-23) can be sequentially (first introduction of $R^1$, then $R^4$ and finally $R^5$) treated with an organometallic reagent, e.g. an organolithium or Grignard-reagent, in a solvent such as an ether, e.g. diethyl ether or more preferably tetrahydrofuran, at temperatures starting from −78° C. and each time eventually raising to 23° C., where after aqueous workup with ammonium chloride solution of each step first the corresponding Weinreb amide instead of the ethyl ester of general formula XXXI, then the ketone bearing $R^1$ and $R^4$ and finally the alcohols of general formula XXXII are obtained.

Hydrolysis of the chiral directing group in the alcohols of general formula XXXII to give the chiral amino alcohol of general formula VIII can be accomplished with a mineral acid, e.g. sulfuric acid or preferably hydrochloric acid in a solvent such as an ether, e.g. diethyl ether, tetrahydrofuran or more preferably 1,4-dioxane.

As an alternative synthetic access to chiral amino alcohols of the general formula VIII, the following route can be employed: Aromatic ketones of general formula IV can be converted into the sulfinyl imine of general formula XXXIII in analogy to T. P. Tang & J. A. Ellman, J. Org. Chem. 1999, 64, 12, by condensation of the aryl ketone group and a sulfinamide, e.g. an alkyl sulfinamide, in this case most preferably (R)-(+)-tert-butylsulfinamide in the presence of a Lewis acid such as e.g. a titanium(IV) alkoxide, more preferably titanium (IV) ethoxide in a solvent such as an ether, e.g. diethyl ether or more preferably tetrahydrofuran.

The conversion of the sulfinyl imine XXXIII to the nitrile of general formula XXXIV proceeds stereoselectively by the chiral directing group as described by Tang & Ellman or by A. Avenoza, J. H. Busto, F. Corzana, J. M. Peregrina, D. Sucunza, M. M. Zurbano in Synthesis 2005, (4), 575-578.

The sulfinyl imine of general formula XXXIII can be treated with an mixed alkyl alkoxide aluminum cyanide reagent, e.g. ethylaluminium cyanoisopropoxide [EtAl(O-i-Pr)CN], in a solvent such as an ether, e.g. diethyl ether or more preferably tetrahydrofuran, at temperatures starting from $-78°$ C. and eventually raising to $-10°$ C., to generate the nitriles of general formula XXXIV as described e.g. by A. Avenoza, J. H. Busto, F. Corzana, J. M. Peregrina, D. Sucunza, M. M. Zurbano in Synthesis 2005, (4), 575-578.

Hydrolysis of the chiral directing group in the nitriles of general formula XXXIV to give first the chiral amino nitriles can be accomplished with a mineral acid, e.g. sulfuric acid or preferably hydrochloric acid in a solvent such as an ether, e.g. diethyl ether, tetrahydrofuran or more preferably 1,4-dioxane, which is followed by another acidic reaction with a mineral acid, e.g. anhydrous hydrochloric acid or preferably sulfuric acid in a solvent such as an aliphatic alcohol, e.g. ethanol or more preferably methanol, at temperatures from 23 to 80° C., to give the chiral amino esters of general formula XXXV.

The chiral amino esters of general formula XXXV can be treated with an organometallic reagent, e.g. an organolithium or Grignard-reagent, in a solvent such as an ether, e.g. diethyl ether or more preferably tetrahydrofuran, at temperatures starting from $-78°$ C. and eventually raising to 23° C., to generate the chiral amino alcohols of general formula VIIIa.

Also chiral amino esters of general formula XXXV can be reduced to the chiral amino alcohols of general formula VIII, wherein $R^4$ and $R^5$ are hydrogen, by reaction with a reducing agent such as e.g. lithium borohydride or more preferably lithium aluminum hydride in an ether solvent, like e.g. diethyl ether or more preferably THF, at temperatures between 0 and 50° C., preferably at 23° C.

Scheme 8: Alternative enantioselective synthesis of aminoalcohols of formula VIII and VIIIa.

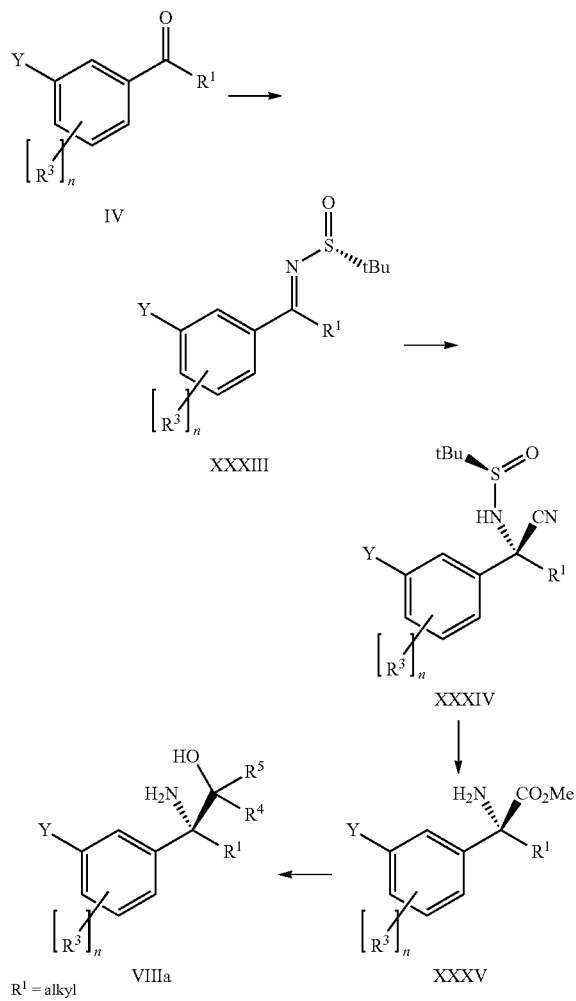

Scheme 9: Synthesis of intermediate lactames.

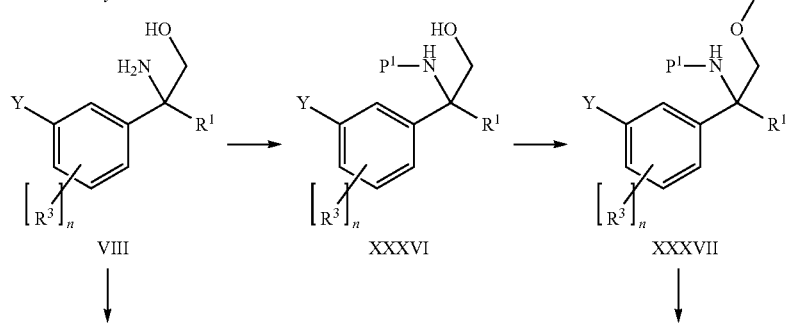

-continued

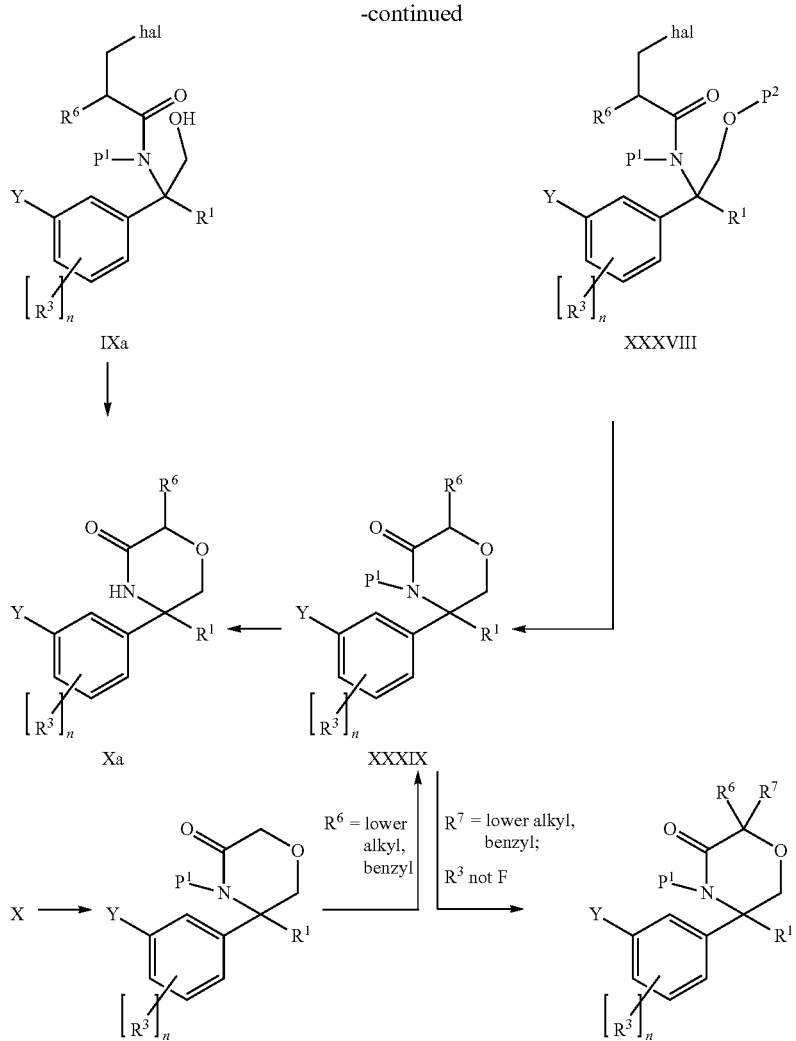

P¹, P² = protecting groups
hal = Cl, Br, I

The intermediate lactams of formula Xa can be obtained as follows: Selective N-protection of the aminoalcohol of formula VIII can be effected by reductive amination with benzaldehydes, preferably with 4-methoxybenzaldehyde, in presence of reducing agents like sodium borohydride or sodium cyano borohydride, preferably sodium triacetoxyborohydride to give amines of formula XXXVI.

Advantageously, the O-protection of compound XXXVI can be effected by a silyl group, eg. tert-butyldimethylsilyl, cleavable by fluoride which at the same time can later on act as a base in the cyclisation step of compounds of formula XXXVIII to yield compounds of formula XXXIX.

Beforehand, the N-acylation of the diprotected aminoalcohol of formula XXXVII can be effected by condensation with halogenated propionic acid derivatives, optionally substituted in position 2 by R⁶ which has the meaning as defined above. Conditions for such condensation are known to those skilled in the art, preferably Schotten-Baumann conditions for acid chlorides with e.g. chloroform as the organic solvent and sodium hydrogen-carbonate as the aqueous base to form the biphasic system were applied to yield amides of formula XXXVIII.

Cleavage of the N-protecting group of compounds of formula XXXIX can be accomplished preferably by strong acid, e.g. trifluoromethanesulfonic acid, in presence of anisole and with trifluoroacetic acid as the solvent to yield the lactam of formula Xa Alternatively, the intermediate lactams of formula Xa can be obtained by direct selective N-acylation of the aminoalcohol of formula VIII with halogenated propionic acid derivatives, optionally substituted in position 2 by R⁶ which has the meaning as defined above. Reaction of the corresponding acid chlorides in inert organic solvents, eg. tetrahydrofuran, dioxane, or acetonitrile, in presence of an organic base, e.g. triethylamine, at temperatures between 0 and 23° C. yielded amides of formula IXa.

The cyclization to lactams of formula Xa can be effected by treatment of amides of formula IXa with a base, e.g. tert-butanolate, in solvents such as tent-butanol at temperatures ranging from 10° C. to reflux.

Furthermore, lactams of formula Xa can be prepared by N-alkylation of lactams of formula X by treatment with benzylhalogenides such as 4-methyoxybenzylhalogenide or 3,4-dimethoxybenzylhalogenide, preferably 4-methyoxybenzylbromide, in presence of a base, e.g. tert-butanolate, in inert organic solvents like e.g. N,N-dimethylformamide to yield N-protected lactams of formula XL.

Compounds of formula XXXIX can be obtained by treatment of compounds of formula XL with alkylating or benzylating agents, e.g. iodomethane or benzylbromide, in presence of a base such as lithium diisopropylamide in inert solvents like e.g. tetrahydrofuran, dioxane, 1,2-dimethoxyethane, preferably tetrahydrofuran, at −75° C. The cleavage of the N-protecting group to compounds of formula Xa can be achieved as described before.

With the proviso that $R^3$ is not F, compounds of formula Xa' can be obtained by treatment of compounds of formula XXXIX with alkylating or benzylating agents under conditions as described before.

For the further transformation to the corresponding aniline derivatives the same procedures were applied as described before.

The corresponding pharmaceutically acceptable salts with acids can be obtained by standard methods known to the person skilled in the art, e.g. by dissolving the compound of formula I in a suitable solvent such as e.g. dioxane or tetrahydrofuran and adding an appropriate amount of the corresponding acid. The products can usually be isolated by filtration or by chromatography. The conversion of a compound of formula I into a pharmaceutically acceptable salt with a base can be carried out by treatment of such a compound with such a base. One possible method to form such a salt is e.g. by addition of 1/n equivalents of a basic salt such as e.g. $M(OH)_n$, wherein M=metal or ammonium cation and n=number of hydroxide anions, to a solution of the compound in a suitable solvent (e.g. ethanol, ethanol-water mixture, tetrahydrofuran-water mixture) and to remove the solvent by evaporation or lyophilisation.

Insofar as their preparation is not described in the examples, the compounds of formula I as well as all intermediate products can be prepared according to analogous methods or according to the methods set forth herewithin. Starting materials are commercially available, known in the art or can be prepared by methods known in the art or in analogy thereto.

It will be appreciated that the compounds of general formula I in this invention can be derivatized at functional groups to provide derivatives which are capable of conversion back to the parent compound in vivo.

Pharmacological Tests

The compounds of formula I and their pharmaceutically acceptable salts possess valuable pharmacological properties. Compounds of the present invention are associated with inhibition of BACE1 and/or BACE2 activity. The compounds were investigated in accordance with the test given hereinafter.

Assay A
Binding studies using SPR based methods
Instrumentation:
The binding assay is performed on an A100 SPR instrument from GEHealthcare using a CM5 sensor chip.
Buffers:
Buffer A: 10 mM acetate pH 4.5
Buffer B: 10 mM acetate (pH 4.6), 150 mM NaCl, 3 mM EDTA, 0.05% P20
Buffer C: 10 mM acetate (pH 4.6), 150 mM NaCl, 3 mM EDTA, 0.05% P20, 4% DMSO
Immobilisation of BACE1

Full length BACE-1 (6his-tagged full length BACE 1 expressed in SF9 cells) is immobilized on one spot of the CM5 sensor chip applying the standard amine coupling chemistry protocol recommended by the chip manufacturer (GEHealthcare). The coupling kit of GEHealthcare (order code BR-1000-50) is used. Buffer B is used as the running buffer. The carboxylic acid groups on the CM5 sensor chip are activated by contacting the surface with a mixture of N-hydroxysuccinimide (55.75 mg/ml) and 1-ethyl-3-(3-diaminopropyl)-carbodiimide hydrochloride (375 mg/ml) for 10 min. The activated surface is then contacted with a solution of BACE-1 (100 µg/ml) dissolved in buffer A. The contact is terminated as soon as the desired amount of protein (~13000 RU corresponding to ~13 ng/mm2 of protein) is attached to the surface. Excess carbodiimide ester groups on the surface are quenched by contacting the surface for 7 minutes with 1.0 M ethanolamine solution (pH 8.0).

Immobilisation of BACE2

BACE2 enzyme ectodomain (derived from plasmid "pET17b-T7-hu proBACE2") was prepared as described in the art (Ostermann et al., "Crystal Structure of Human BACE2 in Complex with a Hydroxyethylamine Transition-state Inhibitor", Journal of Molecular Biology 2006, 355, 249-261). BACE2 is immobilized on a one spot of the CM5 sensor chip applying the standard amine coupling chemistry protocol recommended by the chip manufacturer (GE Healthcare). The coupling kit of GE Healthcare (order code BR-1000-50) is used. Buffer B is used as the running buffer. The carboxylic acid groups on the CM5 sensor chip are activated by contacting the surface with a mixture of N-hydroxysuccinimide (55.75 mg/ml) and 1-ethyl-3-(3-diaminopropyl)-carbodiimide hydrochloride (375 mg/ml) for 10 min. The activated surface is then contacted with a solution of BACE-2 (100 µg/ml) dissolved in buffer A. The contact is terminated as soon as the desired amount of protein (~13000 RU corresponding to ~13 ng/mm2 of protein) is attached to the surface. Excess carbodiimide ester groups on the surface are quenched by contacting the surface for 7 minutes with 1.0 M ethanolamine solution (pH 8.0).

Preparation of Sample Solutions for Binding Experiments

The compounds to be characterized by equilibrium binding constants and kinetic rate constants are dissolved in pure dimethylsulfoxide (10 mM). The dimethylsulfoxide solution is diluted into buffer B in a way to obtain the desired starting concentration of the concentration series and a final dimethylsulfoxide content of the solution of 4%. A concentration series (10 concentrations) is then produced from this stock solution by diluting it with buffer C applying variable dilution factors of 1.0, 0.8, 0.75, 0.66, 0.5, 0.5, 0.5, 0.5, 0.5, 0.5; or 0.8, 0.75, 0.66, 0.5, 0.5, 0.5, 0.5, 0.5, 0.5.

Binding Experiments

Binding experiments are performed using buffer C as the running buffer. The immobilized BACE1 and BACE2 proteins, respectively, are contacted in parallel with a flow (30 µl/min) of the sample solutions for 2 minutes. The binding reaction is monitored in real time. After the contact phase the sensor chip is contacted again with running buffer and the dissociation of the samples is again monitored. After each sample of a concentration series the sensor surface is extensively washed to remove all sample from the surface before starting a new binding experiment with the next solution. After each concentration series the binding activity of the immobilized BACE1 and BACE2 proteins are controlled by monitoring the binding curve of a known positive control sample.

Evaluation of the Binding Parameters from the Monitored Binding Curves a) High affinity binders show often time resolved association and dissociation reactions. In this case the binding curves of a concentration series are fitted with the differential equation describing the kinetics of a 1/1 binding reaction. The software package (Biaeval) provided by the instrument manufacturer is used. The kinetic fit delivers the kinetic rate constants ka (M−1·s−1) and kd (s−1) and the equilibrium binding constant KD(=koff/kon).

b) Low affinity binders often show a fast association and a fast dissociation reaction that can not be resolved by the instrument. In this case, equilibrium responses measured for the different concentrations of a series at the end of the association phase are plotted against the logarithms of the concentrations. The resulting curve is fitted with a mathematical function using the Sigma plot fitting procedures. The fit delivers in this case the KD value for the interaction and the respective Hill slope.

Exemplified compounds show $K_D$ values <63 μM as shown in the table below, most preferred are $K_D$ values <20 μM.

Cellular Abeta-Lowering Assay:

Human HEK293 cells which are stably transfected with a vector expressing a cDNA of the human APP wt gene (APP695) were used to assess the potency of the compounds in a cellular assay. The cells were seeded in 96-well microtiter plates in cell culture medium (Iscove, plus 10% (v/v) fetal bovine serum, glutamine, penicillin/streptomycin) to about 80% confluence and the compounds were added at a 10× concentration in 1/10 volume of medium without FCS containing 8% DMSO (final concentration of DMSO was kept at 0.8% v/v). After 18-20 hrs incubation at 37° C. and 5% $CO_2$ in a humidified incubator the culture supernatant was harvested for the determination of Aβ40 concentrations. 96 well ELISA plates (e.g., Nunc MaxiSorb) were coated with monoclonal antibody which specifically recognize the C-terminal end of Aβ40 (Brockhaus et al., NeuroReport 9, 1481-1486; 1998). After blocking of non-specific binding sites with e.g. 1% BSA and washing, the culture supernatants were added in suitable dilutions together with a horseradish peroxidase-coupled Aβ detection antibody (e.g., antibody 4G8, Senetek, Maryland Heights, Mo.) and incubated for 5 to 7 hrs. Subsequently the wells of the microtiter plate were washed extensively with Tris-buffered saline containing 0.05% Tween 20 and the assay was developed with tetramethylbenzidine/$H_2O_2$ in citric acid buffer. After stopping the reaction with one volume 1 N $H_2SO_4$ the reaction was measured in an ELISA reader at 450 nm wavelength. The concentrations of Aβ in the culture supernatants were calculated from a standard curve obtained with known amounts of pure Aβ peptide.

Assay for RACE Inhibition by Measuring Cellular TMEM27 Cleavage:

The assay uses the principle of inhibition of human TMEM27 cleavage by endogenous cellular BACE2 in the Ins1e rat cell line and shedding from the cell surface into the culture medium, followed by detection in an ELISA assay. Inhibition of BACE2 prevents the cleavage and shedding in a dose-dependent manner.

The stable cell line "INS-TMEM27" represents an INS1e-derived cell line with inducible expression (using the TetOn system) of full-length hTMEM27 in a doxycycline-dependent manner. The cells are cultured throughout the experiment in RPMI1640+Glutamax (Invitrogen) Penicillin/Streptomycin, 10% Fetal bovine serum, 100 mM pyruvate, 5 mM beta-mercatptoethanol, 100 micrograms/ml G418 and 100 microgram/ml hygromycin and are grown inadherent culture at 37° C. in a standard $CO_2$ cell culture incubator.

INS-TMEM27 cells are seeded in 96-well plates. After 2 days in culture, BACE2 inhibitor is added in a range of concentrations as required by the assay and after a further two hours, doxycycline is added to a final concentration of 500 ng/ml. The cells are incubated for a further 46 hours and the supernatant harvested for detection of shed TMEM27.

An ELISA assay (using a pair of mouse anti-human-TMEM27 antibodies, raised against the extracellular domain of TMEM27) is used for detection of TMEM27 in the culture medium. An $EC_{50}$ for BACE2 inhibition is calculated using the ELISA readout for each inhibitor concentration with standard curve-fitting software such as XLFit for the Excel spreadsheet program.

The assay readout is the initial rate of change of fluorescence intensity giving a relative measure of BACE2 activity. Small values correspond to high inhibition and larger values to low inhibition. To determine $IC_{50}$ values (i.e. the concentration inhibiting the enzyme activity by 50%) of the compound for BACE2, typically, 12 assays were made with a range of concentrations chosen empirically to give low, high and intermediate inhibition of the protease. $IC_{50}$ values were determined using these assay values generated for a range of inhibitor concentrations and the curve fitting software XLfit (IDBS) using the Sigmoidal Dose-Response Model.

The preferred compounds according to formula I have an inhibitory activity in the above cellular assay given as $IC_{50}$ value and in the above assay A given as $K_D$ values. Table 2 illustrates $K_D$ and $IC_{50}$ values of selected examples.

TABLE 2

$K_D$ and $IC_{50}$ values for the interaction of selected examples

| Example No. | BACE1 $K_D$ [μM] | BACE2 $K_D$ [μM] | BACE1 $IC_{50}$ [μM] | BACE2 $IC_{50}$ [μM] |
|---|---|---|---|---|
| 1 | 0.320 | 0.044 | 0.120 | 0.021 |
| 2 | 0.050 | 0.009 | 0.016 | 0.048 |
| 3 | 1.684 | 0.580 | — | — |
| 4 | 1.716 | 0.381 | 0.570 | 0.950 |
| 5 | 62.500 | 5.300 | — | — |
| 6 | 6.900 | 0.230 | 1.530 | 0.660 |
| 7 | 0.183 | 0.023 | 0.041 | 0.049 |
| 8 | 1.487 | 0.106 | 0.327 | 0.360 |
| 9 | 0.717 | 0.063 | 0.058 | 0.043 |
| 10 | 3.301 | 0.361 | — | — |
| 11 | 0.490 | 0.044 | 0.041 | — |
| 12 | — | — | 0.020 | 0.017 |
| 13 | 0.445 | 0.033 | 0.024 | 0.051 |
| 14 | 33.000 | 5.400 | — | — |
| 15 | 20.100 | 6.700 | — | — |
| 16 | 1.408 | 0.513 | — | — |
| 18 | 0.034 | 0.004 | 0.006 | 0.031 |
| 19 | 0.394 | 0.098 | 0.130 | 0.837 |
| 20 | 0.050 | 0.008 | 0.003 | 0.006 |
| 21 | 0.017 | 0.004 | 0.003 | 0.002 |
| 22 | 0.140 | 0.019 | 0.011 | 0.011 |
| 23 | 0.309 | 10.836 | 0.160 | — |
| 24 | 1.877 | 5.747 | 0.120 | — |
| 25 | 4.172 | 1.220 | 0.410 | — |
| 26 | — | — | 0.375 | 2.227 |
| 27 | — | — | 1.130 | 0.320 |
| 28 | 0.071 | 0.011 | 0.019 | 0.058 |
| 29 | 0.058 | 0.006 | 0.050 | 0.140 |
| 30 | — | — | 0.023 | — |
| 31 | — | — | 0.023 | — |
| 32 | 4.200 | 20.000 | 0.670 | — |
| 33 | 0.077 | 0.141 | 0.026 | — |
| 34 | 0.003 | 0.003 | 0.004 | 0.004 |
| 35 | 0.028 | 0.004 | 0.015 | 0.016 |
| 36 | 2.265 | 0.955 | 0.550 | 0.120 |
| 37 | 0.283 | 0.020 | 0.240 | 0.017 |
| 38 | 0.039 | 0.032 | 0.021 | 0.044 |
| 39 | 0.045 | 0.008 | 0.028 | 0.130 |
| 40 | 0.015 | 0.002 | 0.013 | 0.002 |

TABLE 2-continued $K_D$ and $IC_{50}$ values for the interaction of selected examples

| Example No. | BACE1 $K_D$ [μM] | BACE2 $K_D$ [μM] | BACE1 $IC_{50}$ [μM] | BACE2 $IC_{50}$ [μM] |
|---|---|---|---|---|
| 41 | 0.054 | 0.006 | 0.026 | 0.004 |
| 42 | 0.208 | 2.550 | 0.190 | — |
| 43 | 0.085 | 0.005 | 0.079 | 0.013 |
| 44 | 1.820 | 0.043 | 0.470 | 0.310 |
| 45 | 3.940 | 3.020 | 0.760 | 0.620 |
| 46 | 10.750 | 0.629 | 1.350 | 0.720 |
| 47 | — | — | 0.800 | 0.730 |
| 48 | 1.200 | 0.115 | 0.350 | 0.052 |
| 49 | 0.015 | 0.022 | 0.004 | 0.066 |
| 50 | 0.900 | 2.100 | 0.039 | 1.400 |
| 51 | 0.022 | 0.002 | 0.014 | 0.005 |
| 52 | 0.194 | >10 | 1.180 | — |
| 53 | 3.950 | 1.220 | 0.620 | 0.910 |
| 54 | >10 | 6.100 | — | — |
| 55 | 6.400 | 2.300 | — | 0.046 |
| 56 | 10.850 | 1.720 | 1.190 | >10 |
| 57 | >10 | 1.800 | — | 0.320 |
| 58 | >10 | 3.600 | — | — |
| 59 | 9.600 | 4.000 | — | — |
| 60 | 0.112 | 0.117 | 0.140 | — |
| 61 | 0.440 | 4.679 | 0.390 | — |
| 62 | 5.521 | 7.340 | 0.270 | — |
| 63 | 3.060 | 1.090 | 0.510 | — |
| 64 | 0.483 | 7.820 | 0.660 | — |
| 65 | 2.473 | 1.12 | 0.180 | — |
| 66 | 0.173 | 0.159 | 0.680 | — |
| 67 | 0.011 | 0.015 | — | — |
| 68 | — | — | 0.010 | — |
| 69 | — | — | 0.009 | — |
| 70 | 1.100 | 0.045 | — | — |
| 71 | 1.500 | 6.000 | — | — |
| 72 | 0.016 | 0.025 | 0.003 | 0.039 |
| 73 | 0.009 | 0.051 | 0.004 | 0.105 |
| 74 | 0.010 | 0.002 | 0.004 | 1.354 |
| 75 | 0.261 | 2.150 | 0.110 | >10 |
| 76 | 0.093 | 0.988 | 0.015 | — |
| 77 | 1.440 | 2.600 | 0.800 | — |
| 78 | 0.885 | 6.500 | 0.500 | — |
| 79 | 4.000 | 4.900 | — | — |
| 80 | 2.270 | 0.045 | 0.700 | 0.084 |
| 81 | 0.102 | 0.256 | 0.047 | 0.210 |
| 82 | 0.129 | 0.113 | 0.046 | 0.140 |
| 83 | 0.916 | 0.276 | 0.300 | 0.130 |
| 84 | 0.261 | 0.077 | 0.140 | 0.083 |
| 85 | >10 | 6.900 | — | — |
| 86 | >10 | 3.600 | — | — |
| 87 | 0.474 | 0.477 | 0.120 | 0.052 |
| 88 | >10 | 3.450 | 2.760 | 0.560 |
| 89 | 0.805 | — | 0.500 | 0.820 |
| 90 | 0.148 | 0.150 | 0.220 | 1.220 |
| 91 | 0.994 | 1.140 | 1.460 | 0.095 |
| 92 | 2.225 | 1.070 | 0.400 | 1.090 |
| 93 | >10 | 3.850 | 6.820 | 3.390 |
| 94 | 2.700 | 1.955 | 1.400 | 1.080 |
| 95 | >10 | 3.600 | — | — |
| 96 | >10 | 6.100 | — | — |
| 97 | >10 | 1.760 | — | — |
| 98 | 0.014 | 0.004 | 0.007 | 0.001 |
| 99 | 0.046 | 0.008 | 0.017 | 0.003 |

Pharmaceutical Compositions

The compounds of formula I and the pharmaceutically acceptable salts can be used as therapeutically active substances, e.g. in the form of pharmaceutical compositions. Thus, the present invention also provides pharmaceutical compositions containing compounds of the invention and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical preparations can be administered orally, e.g. in the form of tablets, coated tablets, dragées, hard and soft gelatine capsules, solutions, emulsions or suspensions. The administration can, however, also be effected rectally, e.g. in the form of suppositories, or parenterally, e.g. in the form of injection solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are however usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain pharmaceutically acceptable auxiliary substances such as preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The present invention also provides a method for the manufacture of pharmaceutical compositions. Such process comprises bringing one or more compounds of formula I and/or pharmaceutically acceptable acid addition salts thereof and, if desired, one or more other therapeutically valuable substances into a galenical administration form together with one or more therapeutically inert carriers.

The dosage at which compounds of the invention can be administered can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage can be administered as single dose or in divided doses and, in addition, the upper limit can also be exceeded when this is found to be indicated.

The following examples illustrate the present invention without limiting it, but serve merely as representative thereof. Examples of compositions according to the invention are:

Example A

Tablets of the following composition are manufactured in the usual manner:

TABLE 3

Possible tablet composition

| ingredient | mg/tablet | | | |
|---|---|---|---|---|
| | 5 | 25 | 100 | 500 |
| compound of formula I | 5 | 25 | 100 | 500 |
| lactose anhydrous DTG | 125 | 105 | 30 | 150 |
| Sta-Rx 1500 | 6 | 6 | 6 | 60 |

TABLE 3-continued

Possible tablet composition

| ingredient | mg/tablet | | | |
|---|---|---|---|---|
| | 5 | 25 | 100 | 500 |
| microcrystalline cellulose | 30 | 30 | 30 | 450 |
| magnesium Stearate | 1 | 1 | 1 | 1 |
| Total | 167 | 167 | 167 | 831 |

Manufacturing Procedure
1. Mix ingredients 1, 2, 3 and 4 and granulate with purified water.
2. Dry the granules at 50° C.
3. Pass the granules through suitable milling equipment.
4. Add ingredient 5 and mix for three minutes; compress on a suitable press.

Example B-1

Capsules of the following composition are manufactured:

TABLE 4

Possible capsule ingredient composition

| ingredient | mg/capsule | | | |
|---|---|---|---|---|
| | 5 | 25 | 100 | 500 |
| compound of formula I | 5 | 25 | 100 | 500 |
| hydrous lactose | 159 | 123 | 148 | — |
| corn starch | 25 | 35 | 40 | 70 |
| talk | 10 | 15 | 10 | 25 |
| magnesium stearate | 1 | 2 | 2 | 5 |
| Total | 200 | 200 | 300 | 600 |

Manufacturing Procedure
1. Mix ingredients 1, 2 and 3 in a suitable mixer for 30 minutes.
2. Add ingredients 4 and 5 and mix for 3 minutes.
3. Fill into a suitable capsule.

The compound of formula I, lactose and corn starch are firstly mixed in a mixer and then in a comminuting machine. The mixture is returned to the mixer, the talc is added thereto and mixed thoroughly. The mixture is filled by machine into suitable capsules, e.g. hard gelatine capsules.

Example B-2

Soft Gelatin Capsules of the following composition are manufactured:

TABLE 5

Possible soft gelatine capsule ingredient composition

| ingredient | mg/capsule |
|---|---|
| compound of formula I | 5 |
| yellow wax | 8 |
| hydrogenated soybean oil | 8 |
| partially hydrogenated plant oils | 34 |
| soybean oil | 110 |
| Total | 165 |

TABLE 6

Possible soft gelatine capsule composition

| ingredient | mg/capsule |
|---|---|
| gelatine | 75 |
| glycerol 85% | 32 |
| karion 83 | 8 (dry matter) |
| titanium dioxide | 0.4 |
| iron oxide yellow | 1.1 |
| Total | 116.5 |

Manufacturing Procedure

The compound of formula I is dissolved in a warm melting of the other ingredients and the mixture is filled into soft gelatin capsules of appropriate size. The filled soft gelatin capsules are treated according to the usual procedures.

Example C

Suppositories of the following composition are manufactured:

TABLE 7

Possible suppository composition

| ingredient | mg/supp. |
|---|---|
| compound of formula I | 15 |
| suppository mass | 1285 |
| Total | 1300 |

Manufacturing Procedure

The suppository mass is melted in a glass or steel vessel, mixed thoroughly and cooled to 45° C. Thereupon, the finely powdered compound of formula I is added thereto and stirred until it has dispersed completely. The mixture is poured into suppository moulds of suitable size, left to cool; the suppositories are then removed from the moulds and packed individually in wax paper or metal foil.

Example D

Injection solutions of the following composition are manufactured:

TABLE 8

Possible injection solution composition

| ingredient | mg/injection solution. |
|---|---|
| compound of formula I | 3 |
| polyethylene glycol 400 | 150 |
| acetic acid | q.s. ad pH 5.0 |
| water for injection solutions | ad 1.0 ml |

Manufacturing Procedure

The compound of formula I is dissolved in a mixture of Polyethylene Glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

Example E

Sachets of the following composition are manufactured:

TABLE 9

| Possible sachet composition | |
|---|---|
| ingredient | mg/sachet |
| compound of formula I | 50 |
| lactose, fine powder | 1015 |
| microcrystalline cellulose (AVICEL PH 102) | 1400 |
| sodium carboxymethyl cellulose | 14 |
| polyvinylpyrrolidon K 30 | 10 |
| magnesium stearate | 10 |
| flavoring additives | 1 |
| Total | 2500 |

Manufacturing Procedure

The compound of formula I is mixed with lactose, microcrystalline cellulose and sodium carboxymethyl cellulose and granulated with a mixture of polyvinylpyrrolidon in water. The granulate is mixed with magnesium stearate and the flavoring additives and filled into sachets.

Experimental Part

The following examples are provided for illustration of the invention. They should not be considered as limiting the scope of the invention, but merely as being representative thereof.

Preparation of Building Block A (RS)-5-(3-Amino-phenyl)-5-methyl-morpholin-3-one hydrochloride

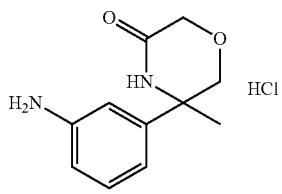

a) (RS)-5-(3-Bromo-phenyl)-5-methyl-imidazolidine-2,4-dione

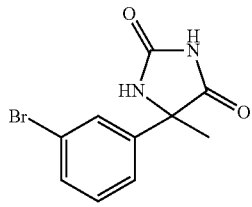

A mixture of 3-bromo-acetophenone (10.0 g, 50 mmol), potassium cyanide (4.96 g, 75 mmol), and ammonium carbonate (33.45 g, 348 mmol) in ethanol (65 ml) was heated in an autoclave at 120° C. for 16 h. For the workup, the reaction mixture was cooled to room temperature, then treated with water (250 ml) and ethyl acetate (500 ml). The aqueous layer was separated and re-extracted with ethyl acetate (250 ml). The combined organic layers were washed twice with saturated sodium chloride solution (2×250 ml), thereafter dried over sodium sulfate, and evaporated at reduced pressure. There were obtained 13.2 g (98.6% of theory) of (RS)-5-(3-bromo-phenyl)-5-methyl-imidazolidine-2,4-dione as a white solid. The purity of the product allowed using it in the next step without further purification. Mass (calculated) $C_{10}H_9BrN_2O_2$ [269.099]; (found) $[M-H]^-=267$, $[[M+2-H]^-=269$.

b) (RS)-2-Amino-2-(3-bromo-phenyl)-propionic acid methyl ester

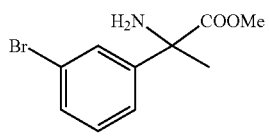

A dispersion of (RS)-2-amino-2-(3-bromo-phenyl)-propionic acid methyl ester (12.81 g, 48 mmol) in 6 N sodium hydroxide solution (95.23 ml) was heated to reflux for 48 h. For the workup, the reaction mixture was cooled with ice and treated with hydrochloric acid (36.5%) until pH 1 was reached. The mixture was evaporated to dryness at reduced pressure. The crude (RS)-2-amino-2-(3-bromo-phenyl)-propionic acid hydrochloride was dispersed in methanol (500 ml) and cooled to 0° C. Within 12 minutes and under ice cooling, thionylchloride (18.02 ml, 246 mmol) was added dropwise. After complete addition, the reaction mixture was heated to reflux for 60 h. For the workup, the reaction mixture was cooled to room temperature and evaporated at reduced pressure. The white residue was treated with a mixture of water and ice (200 ml), triethylamine (16.5 ml), and diethylether (500 ml). The resulting suspension was filtrated over Dicalite; thereafter the aqueous layer was separated and re-extracted with diethylether (250 ml). The combined organic layers were washed with saturated sodium chloride solution (250 ml), dried over sodium sulfate, and evaporated at reduced pressure. There were obtained 9.39 g (76.7% of theory) of (RS)-2-amino-2-(3-bromo-phenyl)-propionic acid methyl ester as a light yellow oil. The purity of the product allowed using it in the next step without further purification. Mass (calculated) $C_{10}H_{12}BrNO_2$ [258.117]; (found) $[M+H]^+=258$, $[M+2-H]^+=260$.

c) (RS)-2-Amino-2-(3-bromo-phenyl)-propan-1-ol

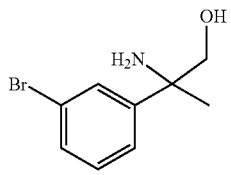

A solution of the (RS)-2-amino-2-(3-bromo-phenyl)-propionic acid methyl ester (9.39 g, 36 mmol) in tetrahydrofuran (360 ml) was treated portionwise at −5° C. with lithiumaluminiumhydride (1.41 g, 36 mmol; 282 mg/2 min). After complete addition, stirring was continued at 0-5° C. for 30 minutes. For the workup, the reaction mixture was cooled to −7° C., and water (9 ml) was added dropwise. Thereafter, 2 N sodium hydroxide solution (9 ml) was added and stirring continued for 15 minutes at room temperature. They grey suspension was filtrated through Dicalite which was washed with tetrahydrofuran (200 ml). The filtrate was evaporated at reduced pressure. There were obtained 8.67 g of crude (RS)-2-amino-2-(3-bromo-phenyl)-propan-1-ol as colorless oil. The purity of the product allowed using it in the next step without further purification. Mass (calculated) $C_9H_{12}BrNO$ [230.106]; (found) $[M+H]^+=230$, $[M+2-H]^+=232$.

d) (RS)-N-[1-(3-Bromo-phenyl)-2-hydroxy-1-methyl-ethyl]-2-chloro-acetamide

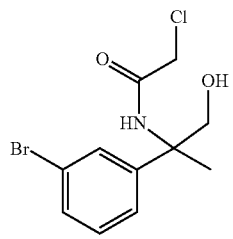

A solution of crude (RS)-2-amino-2-(3-bromo-phenyl)-propan-1-ol (8.38 g, 36 mmol) and triethylamine (6.08 ml, 44 mmol) in acetonitrile (140 ml) was treated dropwise at −2° C. with chloroacetylchloride (3.25 ml, 40 mmol). After complete addition, the orange colored solution was left to warm to room temperature and stirring was continued for 2 h. For the workup, to the reaction was added silica gel (10 g) and it was evaporated at reduced pressure, thereafter, it was purified by chromatography on silica gel using a gradient of dichloromethane/methanol=100/0 to 90/10 as the eluent. There were obtained 9.62 g (86% of theory) of (RS)-N-[1-(3-bromo-phenyl)-2-hydroxy-1-methyl-ethyl]-2-chloro-acetamide as a light brown oil. Mass (calculated) $C_{11}H_{13}BrClNO_2$ [306.589]; (found) $[M+H]^+=306$, $[M+2-H]^+=308$.

e) (RS)-5-(3-Bromo-phenyl)-5-methyl-morpholin-3-one

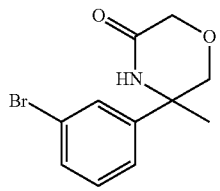

A solution of (RS)-N-[1-(3-bromo-phenyl)-2-hydroxy-1-methyl-ethyl]-2-chloro-acetamide (5.36 g, 17 mmol) in 2-methyl-2-butanol (100 ml) was treated in one portion with potassium tent-butylate (6.66 g, 58 mmol). Initially, the temperature rose to 30° C.; the reaction mixture was left to cool to room temperature and stirring was continued for one hour. For the workup, the reaction mixture was treated with methanol (50 ml), then evaporated at reduced pressure. The residue was purified by chromatography on silica gel using a gradient of dichloromethane/methanol=100/0 to 75/25 as the eluent. There were obtained 4.18 g (88% of theory) of (RS)-5-(3-bromo-phenyl)-5-methyl-morpholin-3-one as a white solid. Mass (calculated) $C_{11}H_{12}BrNO_2$ [270.128]; (found) $[M+H]^+=270$, $[M+2-H]^+=272$.

f) (RS)-5-[3-(Benzhydrylidene-amino)-phenyl]-5-methyl-morpholin-3-one

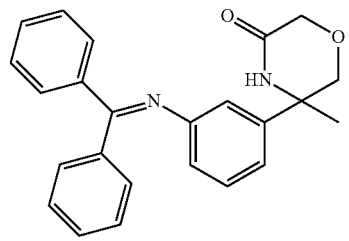

A dried pressure tube was charged consecutively under an argon atmosphere with a solution of (RS)-5-(3-bromo-phenyl)-5-methyl-morpholin-3-one (4.17 g, 15 mmol) in toluene (100 ml), sodium tent-butylate (4.586 g, 46 mmol), 2-di-tert-butylphosphino-2',4',6'-triisopropylbiphenyl (tert-butyl-x-phos) (0.675 g, 1.6 mmol), tris(dibenzylideneacetone)-dipalladium chloroform complex (0.494 g, 0.5 mmol), and benzophenone imine (5.88 g, 31 mmol). The sealed pressure tube was heated at 105° C. for 2.5 days. After cooling, the reaction mixture was evaporated to dryness and directly purified by chromatography on an Isolute flash $NH_2$ column using a gradient of heptane/ethyl acetate=100/0 to 33/66 as the eluent. There were obtained 5.67 g (99% of theory) of (RS)-5-[3-(benzhydrylidene-amino)-phenyl]-5-methyl-morpholin-3-one as a yellow foam. Mass (calculated) $C_{24}H_{22}N_2O_2$ [370.455]; (found) $[M+H]^+=371$.

g) (RS)-5-(3-Amino-phenyl)-5-methyl-morpholin-3-one Hydrochloride

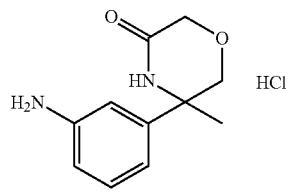

A solution of (RS)-5-[3-(benzhydrylidene-amino)-phenyl]-5-methyl-morpholin-3-one (5.62 g, 15 mmol) in dioxane (75 ml) was cooled to 15° C. and treated dropwise with 1 N hydrochloric acid (18 ml). The reaction mixture was stirred at room temperature overnight. For the workup, the reaction mixture was evaporated at reduced pressure, and the residue was portioned between diethylether (120 ml) and 1 N hydrochloric acid (20 ml). The aqueous phase was separated and washed with diethylether (120 ml). This procedure was repeated twice. The combined aqueous layers were evaporated at reduced pressure, and 3.27 g (88% of theory) of (RS)-5-(3-amino-phenyl)-5-methyl-morpholin-3-one hydrochloride were obtained as a yellowish solid used in the next step without further purification. Mass (calculated) C₁₁H₁₅ClN₂O₂ [242.707]; (found) [M+H]⁺=207.

Preparation of Building Block B (R)-5-(3-Amino-phenyl)-5-methyl-morpholin-3-one Hydrochloride

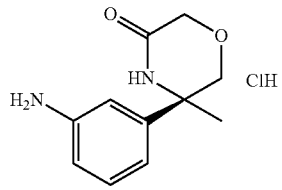

a) (R)-(+)-N-[1-(3-Bromo-phenyl)-2-hydroxy-1-methyl-ethyl]-2-chloro-acetamide and (S)-(−)-N-[1-(3-Bromo-phenyl)-2-hydroxy-1-methyl-ethyl]-2-chloro-acetamide A solution of (RS)-N-[1-(3-bromo-phenyl)-2-hydroxy-1-methyl-ethyl]-2-chloro-acetamide (8.0 g) in dichloromethane was divided in 200 mg aliquots which were separated on chiral HPLC (Reprosil Chiral NR 8 μm, 250×30 mm, Dr. Maisch GmbH) using a 80:20-mixture of heptane and isopropanol as the eluent. The first eluting enantiomer (retention time: 9.40 min), the (S)-(−)-N-[1-(3-bromo-phenyl)-2-hydroxy-1-methyl-ethyl]-2-chloro-acetamide, was obtained as a viscous, colorless oil (3.30 g, 41% of theory), and the second eluting enantiomer (retention time: 14.14 min), the (R)-(+)-N-[1-(3-bromo-phenyl)-2-hydroxy-1-methyl-ethyl]-2-chloro-acetamide, was also obtained as a viscous, colorless oil (3.62 g, 45% of theory), with e.e. >99.5% each.

b) (R)-5-(3-Amino-phenyl)-5-methyl-morpholin-3-one Hydrochloride

In close analogy to the reaction sequence described for the preparation of Building block A, the cyclization of the (R)-N-[1-(3-bromo-phenyl)-2-hydroxy-1-methyl-ethyl]-2-chloro-acetamide with potassium tert-butylate, followed by the palladium-catalyzed amination, and, finally, by the hydrolysis yielded the (R)-5-(3-amino-phenyl)-5-methyl-morpholin-3-one hydrochloride as a light yellow solid. Mass (calculated) C₁₁H₁₅ClN₂O₂ [242.707]; (found) [M+H]⁺=207.
The (S)-5-(3-amino-phenyl)-5-methyl-morpholin-3-one was obtained in the same manner.

Preparation of Building Block C (RS)-5-(5-Amino-2-fluoro-phenyl)-5-methyl-morpholin-3-one hydrochloride

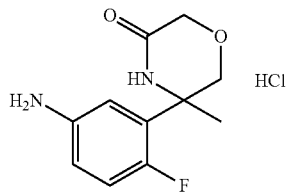

In a reaction sequence analogous to that described for the preparation of Building block A, (RS)-5-(5-bromo-2-fluoro-phenyl)-5-methyl-morpholin-3-one was obtained as follows:

a) 1-(5-Bromo-2-fluoro-phenyl)-ethanone

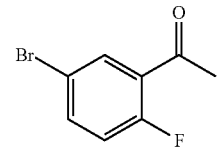

A solution of 5-bromo-2-fluoro-benzoic acid (3.50 g, 16 mmol) in dichloromethane (70 ml) was cooled to 0° C. and treated with triethylamine (1.725 g, 17 mmol), N-(3-dimethylamino-propyl)-N'-ethyl-carbodiimide hydrochloride (3.032 g, 16 mmol), 4-dimethylamino-pyridine (0.097 g, 0.8 mmol), and N,O-dimethyl-hydroxylamine (1.774 g, 18 mmol). The reaction mixture was left to warm to room temperature and stirred for 16 hours. For the workup, the reaction mixture was diluted with dichloromethane (100 ml) and, consecutively, extracted with water (50 ml), citric acid (10%, 50 ml), and saturated sodium hydrogen-carbonate solution (50 ml). The organic layer was dried over sodium sulfate, then evaporated. The crude 5-bromo-2-fluoro-N-methoxy-N-methyl-benzamide material (3.73 g, 91% of theory) was sufficiently pure and was directly engaged in the next step. In a dried flask, a solution of methylmagnesium chloride (3M in tetrahydrofuran, 5.69 ml, 17 mmol) in tetrahydrofuran (24 ml) was treated at 12-16° C. with a solution of 5-bromo-2-fluoro-N-methoxy-N-methyl-benzamide (3.73 g, 14.2 mmol) in tetrahydrofuran (24 ml). After complete addition, the reaction mixture was heated to reflux. After 20 minutes, the white suspension was quenched under ice cooling with a saturated solution of ammonium chloride (25 ml). After dilution with ethyl acetate (50 ml), the aqueous layer was separated and re-extracted with ethyl acetate (50 ml). The combined organic layers were washed with brine (20 ml), dried over sodium sulfate, and evaporated at reduced pressure. 1-(5-bromo-2-fluoro-phenyl)-ethanone was obtained as a light yellow solid (2.6 g, 84% of theory), which was directly engaged in the next step. R_f: 0.55 (silica gel; eluent: heptane/ethyl acetate=4/1).

b) (RS)-5-(5-Bromo-2-fluoro-phenyl)-5-methyl-imidazolidine-2,4-dione

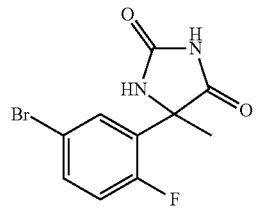

The reaction of 1-(5-bromo-2-fluoro-phenyl)-ethanone with potassium cyanide and ammonium carbonate in ethanol in an autoclave at 120° C. for 16 h yielded the title compound as light yellow solid. Mass (calculated) $C_{10}H_8BrFN_2O_2$ [287.087]; (found) [M−H]⁻=285, [M+2-H]⁻=287.

c) (RS)-2-Amino-2-(5-bromo-2-fluoro-phenyl)-propionic acid methylester

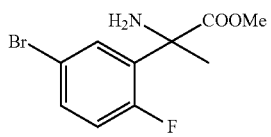

The hydrolysis of the (RS)-5-(5-bromo-2-fluoro-phenyl)-5-methyl-imidazolidine-2,4-dione with 6 N sodium hydroxide solution and esterification of the resulting (RS)-2-amino-2-(5-bromo-2-fluoro-phenyl)-propionic acid with methanol and thionylchloride yielded the (RS)-2-amino-2-(5-bromo-2-fluoro-phenyl)-propionic acid methylester as a light yellow oil. The purity of the product allowed using it in the next step without further purification. Mass (calculated) $C_{10}H_{11}BrFNO_2$ [276.107]; (found) [M+H]⁺=276, [M+2-H]⁺=278.

d) (RS)-2-Amino-2-(5-bromo-2-fluoro-phenyl)-propan-1-ol

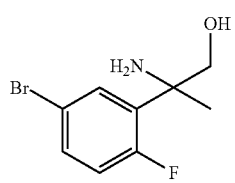

The reduction of the (RS)-2-amino-2-(5-bromo-2-fluoro-phenyl)-propionic acid methylester with lithiumaluminiumhydride in tetrahydrofuran yielded the (RS)-2-amino-2-(5-bromo-2-fluoro-phenyl)-propan-1-ol as a light yellow oil. The purity of the product allowed using it in the next step without further purification. Mass (calculated) $C_9H_{11}BrFNO$ [248.097]; (found) [M+H]⁺=248, [M+2-H]⁺=250.

e) (RS)-N-[1-(5-Bromo-2-fluoro-phenyl)-2-hydroxy-1-methyl-ethyl]-2-chloro-acetamide

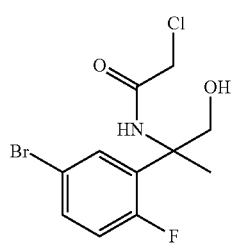

The acylation of the (RS)-2-amino-2-(5-bromo-2-fluoro-phenyl)-propan-1-ol with chloroacetylchloride in acetonitrile yielded, after chromatography on silica gel using a gradient of dichloromethane/methanol=100/0 to 80/20 as the eluent, the (RS)-N-[1-(5-bromo-2-fluoro-phenyl)-2-hydroxy-1-methyl-ethyl]-2-chloro-acetamide as a light brown waxy solid. Mass (calculated) $C_{11}H_{12}BrClFNO_2$ [324.579]; (found) [M+H]⁺=324, [M+2-H]⁺=326.

f) (RS)-5-(5-Bromo-2-fluoro-phenyl)-5-methyl-morpholin-3-one

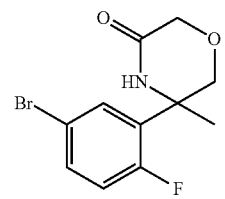

The cyclization of the (RS)-N-[1-(5-bromo-2-fluoro-phenyl)-2-hydroxy-1-methyl-ethyl]-2-chloro-acetamide with potassium tent-butylate yielded, after chromatography on silica gel using a gradient of dichloromethane/methanol=100/0 to 80/20 as the eluent, the (RS)-5-(5-bromo-2-fluoro-phenyl)-5-methyl-morpholin-3-one as a yellow waxy solid. Mass (calculated) $C_{11}H_{11}BrFNO_2$ [288.118]; (found) [M+H]⁺=288, [M+2-H]⁺=290.

g) (RS)-5-[5-(Benzhydrylidene-amino)-2-fluoro-phenyl]-5-methyl-morpholin-3-one

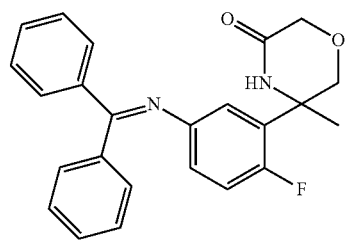

The amination of the (RS)-5-(5-bromo-2-fluoro-phenyl)-5-methyl-morpholin-3-one with sodium tent-butylate, tert-butyl-x-phos, tris(dibenzylideneacetone)-dipalladium chloroform complex, and benzophenonimine in toluene yielded, after chromatography on an Isolute flash $NH_2$ column using a gradient of heptane/ethyl acetate=100/0 to 40/60 as the eluent, the (RS)-5-[5-(benzhydrylidene-amino)-2-fluoro-phenyl]-5-methyl-morpholin-3-one as a yellow oil. Mass (calculated) $C_{24}H_{21}FN_2O_2$ [388.446]; (found) [M+H]⁺=389.

h) (RS)-5-(5-Amino-2-fluoro-phenyl)-5-methyl-morpholin-3-one hydrochloride

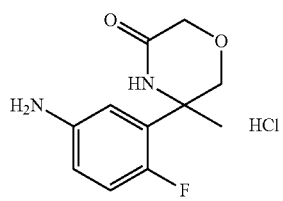

The hydrolysis of the (RS)-5-[5-(benzhydrylidene-amino)-2-fluoro-phenyl]-5-methyl-morpholin-3-one yielded the (RS)-5-(5-amino-2-fluoro-phenyl)-5-methyl-morpholin-3-one hydrochloride as a light yellow solid used in the next step without further purification. Mass (calculated) $C_{11}H_{14}ClN_2O_2$ [260.698]; (found) $[M+H]^+$=225.

Preparation of Building Block D (R)-(+)-5-(5-Amino-2-fluoro-phenyl)-5-methyl-morpholin-3-one hydrochloride

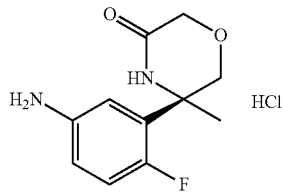

a) (R)-(+)-N-[1-(5-Bromo-2-fluoro-phenyl)-2-hydroxy-1-methyl-ethyl]-2-chloro-acetamide and (S)-(−)-N-[1-(5-Bromo-2-fluoro-phenyl)-2-hydroxy-1-methyl-ethyl]-2-chloro-acetamide A solution of (RS)-N-[1-(5-bromo-2-fluoro-phenyl)-2-hydroxy-1-methyl-ethyl]-2-chloro-acetamide (2.7 g) in dichloromethane was divided in 100 mg aliquots which were separated on chiral HPLC (Reprosil Chiral NR 8 μm, 250×30 mm, Dr. Maisch GmbH) using a 85:15-mixture of heptane and isopropanol as the eluent. The first eluting enantiomer (retention time: 9.94 min), the (S)-(−)-N-[1-(5-bromo-2-fluoro-phenyl)-2-hydroxy-1-methyl-ethyl]-2-chloro-acetamide, was obtained as a light yellow waxy solid (1.05 g, 39% of theory), and the second eluting enantiomer (retention time: 12.92 min), the (R)-(+)-N-[1-(5-bromo-2-fluoro-phenyl)-2-hydroxy-1-methyl-ethyl]-2-chloro-acetamide, was also obtained as a light yellow waxy solid (1.07 g, 40% of theory), with e.e. >99% each.

b) (R)-5-(5-Amino-2-fluoro-phenyl)-5-methyl-morpholin-3-one hydrochloride

In close analogy to the reaction sequence described for the preparation of Building block C, the cyclization of the (R)-N-[1-(5-bromo-2-fluoro-phenyl)-2-hydroxy-1-methyl-ethyl]-2-chloro-acetamide with potassium tent-butylate, followed by the palladium-catalyzed amination, and, finally, by the hydrolysis yielded the (R)-5-(5-amino-2-fluoro-phenyl)-5-methyl-morpholin-3-one hydrochloride as a light yellow solid. Mass (calculated) $C_{11}H_{14}ClN_2O_2$ [260.698]; (found) $[M+H]^+$=225.

The (S)-5-(5-amino-2-fluoro-phenyl)-5-methyl-morpholin-3-one hydrochloride was obtained in the same manner.

Preparation of Building Block E (RS)-5-(5-Amino-2-fluoro-phenyl)-5-methyl-morpholine-3-thione

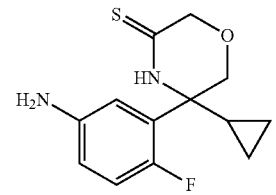

a) (5-Bromo-2-fluoro-phenyl)-cyclopropyl-methanone

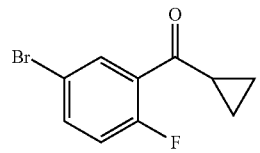

In an analogous manner to that described for the preparation of Building block C [a)], the reaction of 5-bromo-2-fluoro-N-methoxy-N-methyl-benzamide with cyclopropylmagnesium bromide in tetrahydrofuran yielded the title compound as a light yellow liquid; (HPLC 2.783 min 100%). Mass (calculated) $C_{10}H_8BrFO$ [243.074]; (found) $[M+H]^+$= 243, $[M+2-H]^+$=245.

b) 4-Bromo-2-(1-cyclopropyl-vinyl)-1-fluoro-benzene

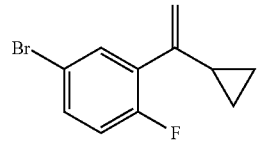

A suspension of methyltriphenylphosphonium bromide (7.142 g, 20 mmol) in toluene (50 ml) was treated with potassium amylate (1.7 M in toluene, 11.76 ml, 20 mmol), and the mixture was stirred at 0° C. for 30 minutes. A solution of (5-bromo-2-fluoro-phenyl)-cyclopropyl-methanone (4.05 g, 17 mmol) in toluene (17 ml) was added and the mixture stirred at room temperature for 2 hours. For the workup, the mixture was extracted with water and ethyl acetate, the organic layer separated, dried and evaporated at reduced pressure. After chromatography on silica gel using a mixture of hexane and ethyl acetate as the eluent, the 4-bromo-2-(1-cyclopropyl-vinyl)-1-fluoro-benzene was obtained as yellow oil (3.816 g, 95% of theory). Mass (calculated) $C_{11}H_{10}BrF$ [241.102]; (found) $[M+H]^+$=241, $[M+2-H]^+$=243.

c) (RS)-4-Bromo-2-(1-cyclopropyl-2-iodo-1-isocyanato-ethyl)-1-fluoro-benzene

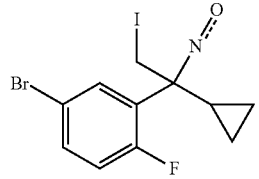

To a suspension of 4-bromo-2-(1-cyclopropyl-vinyl)-1-fluoro-benzene (3.8 g, 16 mmol) and freshly prepared silver cyanate (2.835 g, 19 mmol) in ethyl acetate (8 ml) and acetonitrile (16 ml) was added dropwise within 1 hour at 0° C. in the dark a solution of iodine (4.4 g, 17 mmol) in ethyl acetate (24 ml). Stirring was continued at 0° C. for 1.5 hours, then at 23° C. for 1 hour. The precipitate was filtered off, washed with ethyl acetate. The filtrate was washed with an aqueous solution of sodium sulfite (1%, 50 ml), the organic layer separated, dried over sodium sulfate, then evaporated at reduced pressure. The title compound was obtained as yellow oil (6.4 g, 100% of theory) which was used in the next step without further purification.

d) (RS)-4-(5-Bromo-2-fluoro-phenyl)-4-cyclopropyl-oxazolidin-2-one

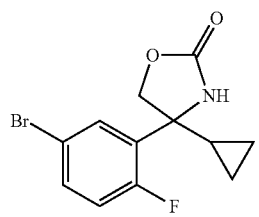

A solution of the crude (RS)-4-bromo-2-(1-cyclopropyl-2-iodo-1-isocyanato-ethyl)-1-fluoro-benzene (6.40 g, 16 mmol) in tent-butanol (200 ml) was treated at 23° C. with triethylamine (2.16 ml, 16 mmol) and the mixture was stirred overnight at reflux. For the workup, the reaction mixture was evaporated at reduced pressure to yield the crude title compound as a yellow oil which was directly used in the next step. Mass (calculated) $C_{12}H_{11}BrFNO_2$ [300.126]; (found) $[M+H]^+=300$, $[M+2-H]^+=302$.

e) (RS)-2-Amino-2-(5-bromo-2-fluoro-phenyl)-2-cyclopropyl-ethanol

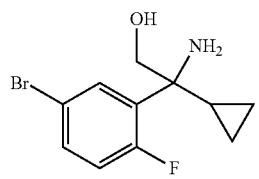

A solution of the crude (RS)-4-(5-bromo-2-fluoro-phenyl)-4-cyclopropyl-oxazolidin-2-one (4.802 g) in ethanol (25 ml) and water (125 ml) was treated with lithium hydroxide monohydrate (6.7 g, 160 mmol) and the reaction mixture was stirred at 100° C. overnight. For the workup, the reaction mixture was extracted with dichloromethane, the combined organic layers were washed with water, then dried over sodium sulfate and evaporated. The crude product was purified by chromatography on an Isolute flash $NH_2$ column using a gradient of heptane/ethyl acetate as the eluent. (RS)-2-amino-2-(5-bromo-2-fluoro-phenyl)-2-cyclopropyl-ethanol was obtained as a yellow oil (2.27 g, 52% of theory). Mass (calculated) $C_{11}H_{13}BrFNO$ [274.132]; (found) $[M+H]^+=274$, $[M+2-H]^+=276$.

f) (RS)-N-[1-(5-Bromo-2-fluoro-phenyl)-1-cyclopropyl-2-hydroxy-ethyl]-2-chloro-acetamide

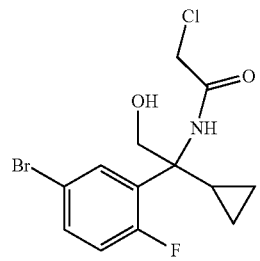

(RS)-2-Amino-2-(5-bromo-2-fluoro-phenyl)-2-cyclopropyl-ethanol (2.27 g, 8 mmol) was dissolved in a mixture of dichloromethane (85 ml) and a saturated aqueous solution of sodium hydrogen-carbonate (85 ml). The biphasic mixture was then treated with a solution of chloroacetylchloride (0.69 ml, 8.7 mmol) in dichloromethane. The reaction mixture was stirred at room temperature and the progress of the transformation checked by chromatography. After completion, the reaction mixture was diluted with dichloromethane, the organic layer separated and washed with water, then dried over sodium sulfate and evaporated. The (RS)-N-[1-(5-bromo-2-fluoro-phenyl)-1-cyclopropyl-2-hydroxy-ethyl]-2-chloro-acetamide was obtained as a yellow oil (2.73 g, 94.0% of theory). Mass (calculated) $C_{13}H_{14}BrClFNO_2$ [350.614]; (found) $[M+H]^+=350$, $[M+2-H]^+=352$, $[M+4-H]^+=354$.

g) (RS)-5-(5-Bromo-2-fluoro-phenyl)-5-cyclopropyl-morpholin-3-one

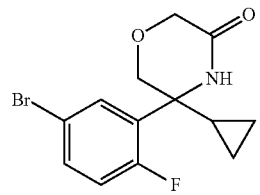

In an analogous manner to that described for the preparation of Building block A [e)], the cyclization of (RS)-N-[1-(5-bromo-2-fluoro-phenyl)-1-cyclopropyl-2-hydroxy-ethyl]-2-chloro-acetamide with potassium tert-butoxide in tent-butanol at room temperature overnight yielded the (RS)-5-(5-bromo-2-fluoro-phenyl)-5-cyclopropyl-morpholin-3- one as a yellow oil (2.146 g, 88% of theory). Mass (calculated) $C_{13}H_{13}BrFNO_2$ [314.153]; (found) $[M+H]^+$=314, $[M+2-H]^+$=316.

h) (RS)-5-[5-(Benzhydrylidene-amino)-2-fluoro-phenyl]-5-cyclopropyl-morpholin-3-one

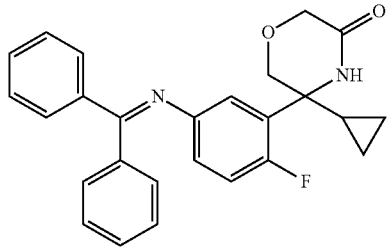

In an analogous manner to that described for the preparation of Building block A [f)], the palladium-catalyzed amination of (RS)-5-(5-bromo-2-fluoro-phenyl)-5-cyclopropyl-morpholin-3-one with benzophenonimine yielded the (RS)-5-[5-(benzhydrylidene-amino)-2-fluoro-phenyl]-5-cyclopropyl-morpholin-3-one as a yellow foam. Mass (calculated) $C_{26}H_{23}FN_2O_2$ [414.478]; (found) $[M+H]^+$=415.

i) (RS)-5-[5-(Benzhydrylidene-amino)-2-fluoro-phenyl]-5-cyclopropyl-morpholine-3-thione

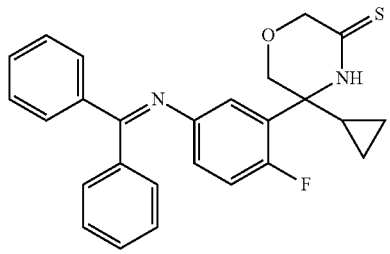

A mixture of (RS)-5-[5-(benzhydrylidene-amino)-2-fluoro-phenyl]-5-cyclopropyl-morpholin-3-one (2.10 g, 5.07 mmol) and Lawesson's reagent (0.926 mg, 2.3 mmol) in tetrahydrofuran (15 mL) was stirred at 70° C. for 3 hours. For the workup, the reaction mixture was diluted with ethyl acetate and extracted with a saturated solution of sodium hydrogen-carbonate. The organic layer was dried over sodium sulfate and evaporated. The crude product was purified by chromatography on silica gel using a gradient of hexane/ethyl acetate as the eluent. The (RS)-5-[5-(benzhydrylidene-amino)-2-fluoro-phenyl]-5-cyclopropyl-morpholine-3-thione was obtained as a yellow foam (1.42 g, 65% of theory). Mass (calculated) $C_{26}H_{23}FN_2OS$ [430.545]; (found) $[M+H]^+$=431.

j) (RS)-5-(5-Amino-2-fluoro-phenyl)-5-cyclopropyl-morpholine-3-thione

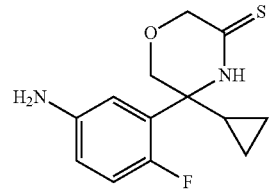

A solution of (RS)-5-[5-(benzhydrylidene-amino)-2-fluoro-phenyl]-5-cyclopropyl-morpholine-3-thione (1.42 g, 3.3 mmol) in dioxane (15 ml) and 1 M HCl (5 ml) was stirred at room temperature for 30 minutes. The reaction mixture was poured on a saturated solution of sodium hydrogen-carbonate and extracted twice with ethyl acetate. The combined organic layers were washed with brine, dried over sodium sulfate, filtered and evaporated at reduced pressure. The residue was purified by chromatography on silica gel using a 3:1-mixture of dichloromethane and ethyl acetate as the eluent. $CH_2Cl_2$/EtOAc 3:1. The (RS)-5-(5-amino-2-fluoro-phenyl)-5-cyclopropyl-morpholine-3-thione was obtained as a white solid (0.810 g, 92% of theory). Mass (calculated) $C_{13}H_{15}FN_2OS$ [266.338]; (found) $[M+H]^+$=267.

Preparation of Building Block F (RS)-5-(3-Amino-phenyl)-5-methyl-morpholine-3-thione

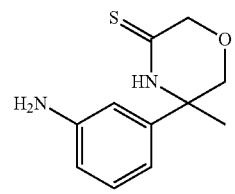

Lawesson's reagent (0.69 g, 1.64 mmol, 1.3 eq.) was added in one portion to a suspension of 5-(3-amino-phenyl)-5-methyl-morpholin-3-one (0.26 g, 1.26 mmol) in 1,2-dimethoxy-ethane (10 ml); the reaction mixture was stirred at 80° C. for 18 hours. After complete conversion, the solvent was partially removed at reduced pressure and the dark orange oil diluted with dichloromethane (5 ml) before washing with 1 M HCl (2×5 ml). The aqueous phase was brought to pH 8 and extracted with dichloromethane (4×10 ml) to yield the (RS)-5-(3-amino-phenyl)-5-methyl-morpholine-3-thione as a yellow oil (0.16 g, 57% of theory). Mass (calculated) $C_{11}H_{14}N_2OS$ [222.31]; (found) $[M+H]^+$=223.

Preparation of Building Block G (RS)-3-(3-Bromo-phenyl)-5-methoxy-3-methyl-3,6-dihydro-2H [1,4]oxazine

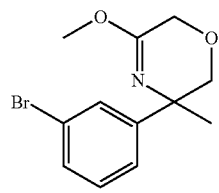

In a vacuum dried flask under an argon atmosphere, a solution of (RS)-5-(3-bromo-phenyl)-5-methyl-morpholin-3-one (3.0 g, 11.1 mmol) in dichloromethane (145 ml) was treated with trimethyloxonium tetrafluoroborate (2.594 g, 17 mmol). The reaction mixture was stirred at room temperature for 17 hours. For the workup, the incomplete reaction was extracted with a saturated solution of sodium hydrogen-carbonate (70 ml). The organic layer was dried over sodium sulfate and evaporated. There were obtained 3.12 g of the title compound as light yellow oil containing about 17% of the starting lactam. Mass (calculated) $C_{12}H_{14}BrNO_2$ [284.16]; (found) $[M+H]^+=284$, $[M+2-H]^+=286$.

Preparation of Building Block H (R)-5-(5-Amino-2-fluoro-phenyl)-5-methyl-morpholine-3-thione

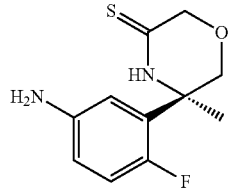

a) (R)-5-[5-(Benzhydrylidene-amino)-2-fluoro-phenyl]-5-methyl-morpholin-3-one As described for the preparation of Building block D, the cyclization of the (R)-N-[1-(5-bromo-2-fluoro-phenyl)-2-hydroxy-1-methyl-ethyl]-2-chloro-acetamide with potassium tert-butylate, followed by the palladium-catalyzed amination yielded the (R)-5-[5-(benzhydrylidene-amino)-2-fluoro-phenyl]-5-methyl-morpholin-3-one as a yellow solid. Mass (calculated) $C_{24}H_{21}FN_2O_2$ [388.45]; (found) $[M+H]^+=$ 389.

b) (R)-5-[5-(Benzhydrylidene-amino)-2-fluoro-phenyl]-5-methyl-morpholine-3-thione A solution of (R)-5-[5-(benzhydrylidene-amino)-2-fluoro-phenyl]-5-methyl-morpholin-3-one 287 mg, 0.7 mmol) in dioxane (4 ml) was treated with Lawesson's reagent (181 mg, 0.5 mmol). After heating at 80° C. for 16 hours the reaction mixture was evaporated at reduced pressure. The residue was directly purified by chromatography on an Isolute flash $NH_2$ column using a gradient of heptane and ethyl acetate=100/0 to 40/60 as the eluent. The title compound was obtained as yellow foam (181 mg, 61.5% of theory). Mass (calculated) $C_{24}H_{21}FN_2OS$ [404.507]; (found) $[M+H]^+=405$.

c) (R)-5-(5-Amino-2-fluoro-phenyl)-5-methyl-morpholine-3-thione

In a manner analogous to the preparation of Building block E the hydrolysis of (R)-5-[5-(benzhydrylidene-amino)-2-fluoro-phenyl]-5-methyl-morpholine-3-thione with hydrochloric acid yielded the title compound as a light brown foam. Mass (calculated) $C_{11}H_{13}FN_2OS$ [240.301]; (found) $[M+H]^+=241$.

Preparation of Building Block I (RS)-[5-(3-Amino-phenyl)-5-methyl-5,6-dihydro-2H-[1,4]oxazin-3-yl]-[bis-(4-methoxy-phenyl)-phenyl-methyl]-amine

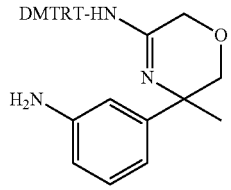

a) (RS)-5-(3-Bromo-phenyl)-5-methyl-5,6-dihydro-2H-[1,4]oxazin-3-ylamine

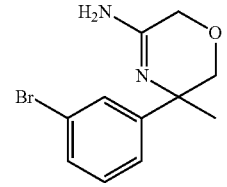

In a vacuum dried flask under an argon atmosphere, a solution of 5-(3-bromo-phenyl)-5-methyl-morpholin-3-one (7.4 g, 27.4 mmol) in dichloromethane (80 ml) was treated with trimethyloxonium tetrafluoroborate (11.6 g, 3 eq). The reaction mixture was stirred at room temperature overnight. The LC-MS profile showed partial conversion into the desired compound so another 1.5 eq of trimethyloxonium tetrafluoroborate were added and the reaction mixture was stirred at room temperature overnight. For the workup, the reaction mixture was washed with a saturated solution of sodium hydrogen-carbonate (50 ml). The organic layer was dried over sodium sulfate and evaporated. The crude product was dissolved in methanol (60 ml) in a microreactor and ammonium chloride (7.4 g, 5.3 eq) was added. The reaction mixture was heated at 100° C. for 16 hours. After cooling, the reaction mixture was filtered and evaporated to dryness, taken up with dichloromethane (30 ml) and filtered again. The solvent was removed and the residue was passed through a SCX (50 g) cartridge, washed with a dichloromethane/methanol mixture and the product was recovered eluting with a solution 2.0 M of ammonia in methanol. The (RS)-5-(3-bromo-phenyl)-5-methyl-5,6-dihydro-2H-[1,4]oxazin-3-ylamine was obtained as a brown oil (3.7 g, 53% of theory). Mass (calculated) $C_{11}H_{13}BrN_2O$ [269.14]; (found) $[M+H]^+=271$.

b) (RS)-[Bis-(4-methoxy-phenyl)-phenyl-methyl]-[5-(3-bromo-phenyl)-5-methyl-5,6-dihydro-2H-[1,4]oxazin-3-yl]-amine

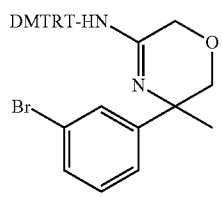

A solution of (RS)-5-(3-bromo-phenyl)-5-methyl-5,6-dihydro-2H-[1,4]oxazin-3-ylamine (3.7 g, 13.8 mmol) and triethylamine (1.5 g, 1.1 eq) in dichloromethane (20 ml) was cooled to 0° C. and 4,4'-dimethoxytriphenylmethyl chloride (5.12 g, 1.1 eq) was added. The reaction mixture was stirred at room temperature overnight. Thereafter, water was added to the mixture and the organic phase was separated, dried over sodium sulfate and concentrated at reduced pressure. The crude was purified by chromatography on silica gel to yield the (RS)-[bis-(4-methoxy-phenyl)-phenyl-methyl]-[5-(3-bromo-phenyl)-5-methyl-5,6-dihydro-2H-[1,4]oxazin-3-yl]-amine as a yellow oil (7.0 g, 99% of theory). Mass (calculated) $C_3H_{31}BrN_2O_3$ [571.52]; (found) $[M+H]^+=571$.

c) (RS)-[5-(3-Amino-phenyl)-5-methyl-5,6-dihydro-2H-[1,4]oxazin-3-yl]-[bis-(4-methoxy-phenyl)-phenyl-methyl]-amine

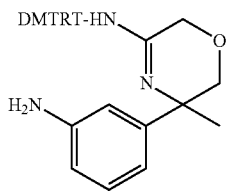

Following the general procedure described below the palladium-catalyzed amination of (RS)-[bis-(4-methoxy-phenyl)-phenyl-methyl]-[5-(3-bromo-phenyl)-5-methyl-5,6-dihydro-2H-[1,4]oxazin-3-yl]-amine followed by the hydrolysis of the intermediate (RS)-{5-[3-(benzhydrylideneamino)-phenyl]-5-methyl-5,6-dihydro-2H-[1,4]oxazin-3-yl}-[bis-(4-methoxy-phenyl)-phenyl-methyl]-amine yielded the title compound. Mass (calculated) $C_{32}H_{33}N_3O_3$ [507.64]; (found) $[M+H]^+=508$.

General procedure: Under an inert atmosphere of nitrogen to a mixture of the bromo-derivative (3 mmol), tert-butanolate (8 mmol), tert-butyl-x-phos (0.3 mmol), and tris(dibenzylideneacetone)-dipalladium chloroform complex (0.1 mmol) were added benzophenonimine (5 mmol) and dry toluene (20 ml). The mixture was heated at 105° C. for 48 h and then allowed to cool to room temperature. Water (10 ml) and dichloromethane (10 ml) were added, the organic layer was separated, washed with water (2×5 ml), dried over sodium sulfate, and evaporated. The crude product was dissolved in 1,4-dioxane (18 ml) and hydrochloric acid (1 M, 6 ml) was added dropwise. The reaction mixture was stirred at room temperature overnight. For the workup, the solvent was removed, the residue was suspended in diethyl ether (10 ml) and washed with hydrochloric acid (6 N). The aqueous phase was separated and extracted with diethylether (2×50 ml). The pH of the aqueous phase was adjusted to 14 using solid sodium hydroxide and the desired product was extracted with dichloromethane (3×50 ml). The organic layer was separated, dried over sodium sulfate and evaporated. The crude product was purified by chromatography on SCX-column and silica column using a mixture of ethyl acetate and cyclohexane as the eluent.

Preparation of Building Block J

[(R)-5-(5-Amino-2-fluoro-phenyl)-5-methyl-5,6-dihydro-2H-[1,4]oxazin-3-yl]-[bis-(4-methoxy-phenyl)-phenyl-methyl]-amine

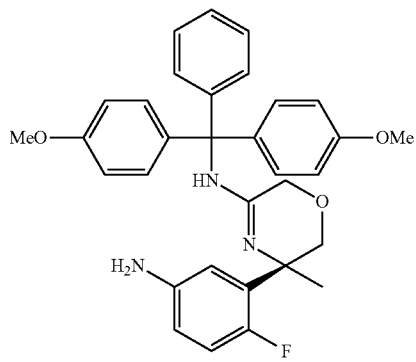

a) (R)-5-(5-Bromo-2-fluoro-phenyl)-5-methyl-morpholin-3-one

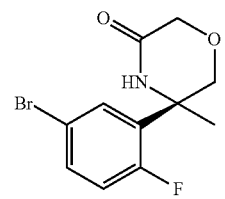

In close analogy to the reaction sequence described for the preparation of Building block C, the cyclization of the (R)-N-[1-(5-bromo-2-fluoro-phenyl)-2-hydroxy-1-methyl-ethyl]-2-chloro-acetamide (see preparation Building block D) with potassium tent-butylate yielded the title compound as a light yellow solid (85% of theory). Mass (calculated) $C_{11}H_{11}BrFNO_2$ [286.99]; (found) $[M+H]^+=287$, $[M+2-H]^+=289$.

b) (R)-5-(5-Bromo-2-fluoro-phenyl)-5-methyl-5,6-dihydro-2H-[1,4]oxazin-3-ylamine

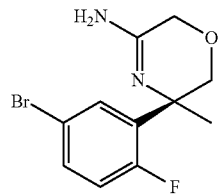

In analogy to step a) in the synthesis of Building block I, the treatment of (R)-5-(5-bromo-2-fluoro-phenyl)-5-methyl-morpholin-3-one followed by the nucleophilic substitution with ammonium chloride yielded the title compound; its hydrochloride was obtained as a white solid (74% of theory). Mass (calculated) $C_{11}H_{12}BrFN_2O$ [287.13]; (found) $[M+H]^+= 287$, $[M+2-H]^+=289$.

c) [Bis-(4-methoxy-phenyl)-phenyl-methyl]-[(R)-5-(5-bromo-2-fluoro-phenyl)-5-methyl-5,6-dihydro-2H-[1,4]oxazin-3-yl]-amine

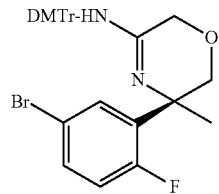

In analogy to step c) in the synthesis of Building block I, the reaction of (R)-5-(5-bromo-2-fluoro-phenyl)-5-methyl-5,6-dihydro-2H-[1,4]oxazin-3-ylamine with 4,4'-dimethoxytriphenylmethyl chloride yielded the title compound as a white solid (72% of theory). Mass (calculated) $C_{32}H_{30}BrFN_2O_3$ [589.51]; (found) $[M+H]^+=589$, $[M+2-H]^+=591$.

d) [(R)-5-(5-Amino-2-fluoro-phenyl)-5-methyl-5,6-dihydro-2H-[1,4]oxazin-3-yl]-[bis-(4-methoxy-phenyl)-phenyl-methyl]-amine Following the general procedure described above [Building block I step c)] the palladium-catalyzed amination of [bis-(4-methoxy-phenyl)-phenyl-methyl]-[(R)-5-(5-bromo-2-fluoro-phenyl)-5-methyl-5,6-dihydro-2H-[1,4]oxazin-3-yl]-amine followed by the hydrolysis of the intermediate benzhydrylidene derivative yielded the title compound (75% of theory). Mass (calculated) $C_{32}H_{32}FN_3O_3$ [525.63]; (found) $[M+H]^+=526$.

Preparation of Building Block K (R)-5-(5-Amino-2-fluoro-phenyl)-5,6,6-trimethyl-morpholine-3-thione

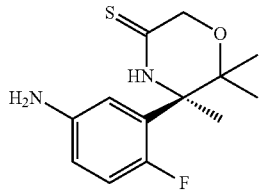

a) (5-Bromo-2-fluoro-phenyl)-oxo-acetic acid ethyl ester

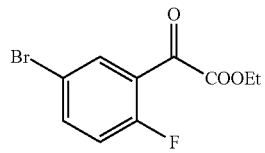

A solution of 4-bromo-1-fluoro-2-iodobenzene (6.3 g, 20.9 mmol) in tetrahydrofuran (100 ml) was treated dropwise with isopropylmagnesium chloride solution (2 M in tetrahydrofuran, 11.5 ml, 23 mmol) at −40° C. to −30° C. The light brown solution was stirred for 30 min at −30° C. Then diethyl oxalate (5.68 ml, 42.0 mmol) was added in one portion at −70° C. (rise of temperature to −55° C.). The cooling bath was removed and the brown-yellow solution was warmed up under stirring to −10° C. during 1 hour. The light brown suspension was poured on ice-cold hydrochloric acid (1 M) and extracted twice with ethyl acetate. The organic layers were washed with water and brine, dried over sodium sulfate, and evaporated at reduced pressure to give 8 g of a yellow liquid. After chromatography on silica gel using a gradient of cyclohexane and dichloromethane=100/0 to 70/30 as the eluent the (5-bromo-2-fluoro-phenyl)-oxo-acetic acid ethyl ester was obtained as a colorless oil (5.33 g, 92% of theory). Mass (calculated) $C_{10}H_8BrFO_3$ [275.072]; (found) $[M]^+=274$, $[M+2-H]^+=276$.

b) (S)-(5-Bromo-2-fluoro-phenyl)-[(Z)-2-methyl-propane-2-sulfinylimino]-acetic acid ethyl ester

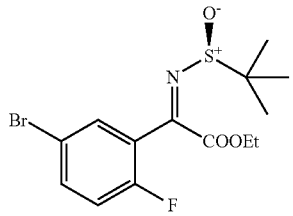

A solution of (S)-(−)-2-methyl-2-propanesulfinamide (2.35 g, 19.4 mmol) and (5-bromo-2-fluoro-phenyl)-oxo-acetic acid ethyl ester (5.33 g, 19.4 mmol) in tetrahydrofuran (80 ml) was treated at room temperature with titanium(IV) ethoxide (8.04 ml, 38.8 mmol). The light brown solution was stirred at 70° C. for 3.5 hours. For the workup, the cooled reaction mixture was poured into ice water, diluted with ethyl acetate, and filtered through a pad of Dicalite. The organic layer was separated, washed with brine, dried over sodium sulfate, and finally evaporated at reduced pressure. The crude product (6.7 g) was purified by chromatography on silica gel using a gradient of cyclohexane and dichloromethane=100/0 to 0/100 as the eluent. (S)-(5-bromo-2-fluoro-phenyl)-[(Z)-2-methyl-propane-2-sulfinylimino]-acetic acid ethyl ester was obtained as a yellow oil (4.9 g, 66% of theory). Mass (calculated) $C_{14}H_{17}BrFNO_3S$ [378.260]; (found) $[M+H]^+=378$, $[M+2-H]^+=380$.

c) (S)-2-Methyl-propane-2-sulfinic acid [(R)-1-(5-bromo-2-fluoro-phenyl)-2-hydroxy-1,2-dimethyl-propyl]amide

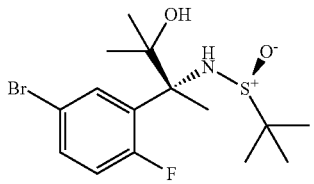

A solution of (S)-(5-bromo-2-fluoro-phenyl)-[(Z)-2-methyl-propane-2-sulfinylimino]-acetic acid ethyl ester (10.4 g, 27 mmol) in anhydrous tetrahydrofuran (150 ml) was cooled to −70° C. A solution of methyl magnesium bromide (3.2 M in 2-methyl-tetrahydrofuran (30.1 ml, 96 mmol) was added dropwise. The yellow solution was warmed up to room temperature during 2 hours and then stirred for 16 hours. For the workup, the yellow solution was quenched with ice-cold saturated ammonium chloride solution and extracted with ethyl acetate. The organic layer was washed with water and brine, dried over sodium sulfate, filtered and evaporated at reduced pressure to give brown oil (11 g). The crude product was purified by chromatography on silica gel using a gradient of heptane and ethyl acetate=100/0 to 20/80 as the eluent. (S)-2-Methyl-propane-2-sulfinic acid [(R)-1-(5-bromo-2-fluoro-phenyl)-2-hydroxy-1,2-dimethyl-propyl]-amide was obtained as a colorless oil (4.2 g, 40% of theory). Mass (calculated) $C_{15}H_{23}BrFNO_2S$ [380.320]; (found) $[M+H]^+=$ 380, $[M+2-H]^+=382$.

d) (R)-3-Amino-3-(5-bromo-2-fluoro-phenyl)-2-methyl-butan-2-ol

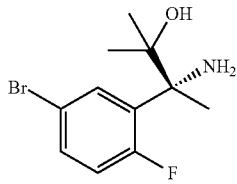

A solution of (S)-2-methyl-propane-2-sulfinic acid [(R)-1-(5-bromo-2-fluoro-phenyl)-2-hydroxy-1,2-dimethyl-propyl]-amide (4.2 g, 11.04 mmol) in tetrahydrofuran (200 ml) was cooled to 0° C. Hydrochloric acid (4 M in dioxane, 11 ml) was added dropwise. The ice bath was removed and stirring continued for 1.5 hours at room temperature. For the workup, the reaction mixture was poured onto a sodium carbonate solution (2 M), extracted twice with ethyl acetate, dried over sodium sulfate, and evaporated at reduced pressure, finally dried under high vacuum. The (R)-3-amino-3-(5-bromo-2-fluoro-phenyl)-2-methyl-butan-2-ol was obtained as light yellow oil (2.94 g, 96.4% of theory). Mass (calculated) $C_{11}H_{15}BrFNO$ [276.147]; (found) $[M+H]^+=276, [M+2-H]^+=$ 278.

e) N-[(R)-1-(5-Bromo-2-fluoro-phenyl)-2-hydroxy-1,2-dimethyl-propyl]-2-chloro-acetamide

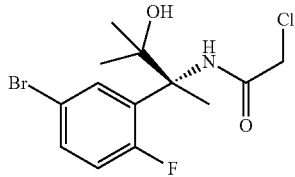

A solution of (R)-3-amino-3-(5-bromo-2-fluoro-phenyl)-2-methyl-butan-2-ol (2.91 g, 10.5 mmol) in dichloromethane (35 ml) was stirred intensively together with a saturated sodium hydrogen-carbonate solution (30 ml) at 0° C. Chloroacetyl chloride (0.92 ml, 11.6 ml) was added and stirring continued for 1 hour at 0° C. For the workup, the aqueous layer was separated and extracted with dichloromethane. The combined organic layers were dried over sodium sulfate, then evaporated. The title compound was obtained as a white solid (3.5 g, 94% of theory) which was used in the next step without further purification. Mass (calculated) $C_{13}H_{16}BrClFNO_2$ [352.629]; (found) $[M+H]^+=352, [M+2-H]^+=354$.

f) (R)-5-(5-Bromo-2-fluoro-phenyl)-5,6,6-trimethyl-morpholin-3-one

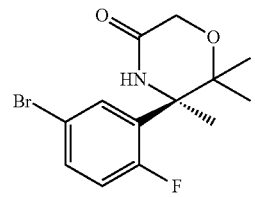

A dispersion of N-[(R)-1-(5-bromo-2-fluoro-phenyl)-2-hydroxy-1,2-dimethyl-propyl]-2-chloro-acetamide (2.79 g, 7.91 mmol) in toluene (80 ml) at 23° C. was treated dropwise with a solution of potassium amylate (1.7 M in toluene, 24 ml, 41 mmol) within 30 minutes (slightly exothermic reaction). After complete addition the mixture was stirred at 23° C. for 45 minutes. For the workup, the reaction mixture was poured into hydrochloric acid (1M) and extracted with ethyl acetate. The organic layer was separated and washed with a saturated sodium hydrogen-carbonate solution and brine. The combined aqueous layers were re-extracted twice with ethyl acetate. The combined organic layers were dried over sodium sulfate, then evaporated at reduced pressure to yield light brown oil. The crude product was purified by chromatography on silica gel using a gradient of heptane and ethyl acetate as the eluent. The (R)-5-(5-bromo-2-fluoro-phenyl)-5,6,6-trimethyl-morpholin-3-one was obtained as a light yellow gum (1.83 g, 73% of theory). Mass (calculated) $C_{13}H_{15}BrFNO_2$ [316.168]; (found) $[M+H]^+=316, [M+2-H]^+=318$.

g) (R)-5-[5-(Benzhydrylidene-amino)-2-fluoro-phenyl]-5,6,6-trimethyl-morpholin-3-one

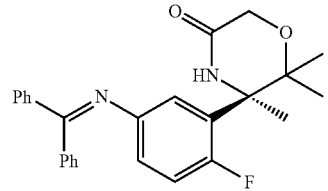

In a sealed tube a solution of (R)-5-(5-bromo-2-fluoro-phenyl)-5,6,6-trimethyl-morpholin-3-one (1.0 g, 3.2 mmol) in toluene (8 ml) was treated consecutively with sodium tert-butylate (912 mg, 9.5 mmol), 2-di-tert-butylphosphino-2',4',6'-triisopropylbiphenyl (tert-butyl-x-phos) (134 mg, 10 mol %) and tris(dibenzylideneacetone)-dipalladium chloroform complex $[Pd_2(dba)_3 \cdot CHCl_3]$ (98 mg, 5 mol %). Benzophenone imine (1.06 ml, 6.3 mmol) was added finally via syringe. The tube was sealed under argon and the mixture was stirred at 105° C. for 20 h. For the workup, the brown solution was extracted with ethyl acetate and water. The organic layer was separated, washed with brine, dried over sodium sulfate, filtered and evaporated at reduced pressure to give brown oil (1.5 g). The crude product was purified by chromatography on silica gel using a gradient of heptane and ethyl acetate=100/0 to 50/50 as the eluent. The (R)-5-[5-(benzhydrylidene-amino)-2-fluoro-phenyl]-5,6,6-trimethyl-morpholin-3-one was obtained as a light yellow foam (1.13 g, 86% of theory). Mass (calculated) $C_{26}H_{25}FN_2O_2$ [416.493]; (found) $[M+H]^+$=417.

h) (5-Chloro-thiophene-2-carboxylic acid [3-(-5-(5-Amino-2-fluoro-phenyl)-5,6,6-trimethyl-morpholine-3-thione

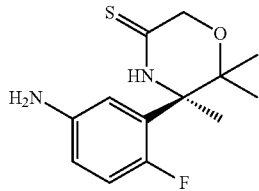

The (R)-5-[5-(benzhydrylidene-amino)-2-fluoro-phenyl]-5,6,6-trimethyl-morpholin-3-one (1.13 g; 2.71 mmol) was dissolved in dioxane (80 ml) and the Lawesson's Reagent (691 mg, 1.71 mmol) was added at room temperature. The reaction mixture was stirred at 80° C. for 2 hours. Thereafter, the green solution was cooled to 23° C., then hydrochloric acid (1M, 3.42 ml) was added and the mixture was stirred for 30 minutes at room temperature. For the workup, the reaction mixture was poured into a saturated sodium hydrogen-carbonate solution and extracted with ethyl acetate. The organic layer was washed with brine, dried over sodium sulfate, and evaporated at reduced pressure to give blue oil (1.33 g). The crude product was purified by chromatography on silica gel using a gradient of heptane and ethyl acetate=100/0 to 50/50 as the eluent. The (R)-5-(5-amino-2-fluoro-phenyl)-5,6,6-trimethyl-morpholine-3-thione was obtained as a white foam (0.63 g, 86% of theory). Mass (calculated) $C_{13}H_{17}FN_2OS$ [268.354]; (found) $[M+H]^+$=269.

Preparation of Building Block L (R)-5-(3-Amino-phenyl)-2,2,5-trimethyl-morpholine-3-thione

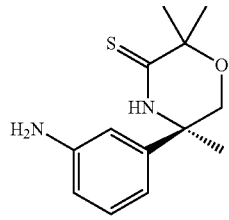

a) (R)-5-(3-Bromo-phenyl)-5-methyl-morpholin-3-one

In close analogy to the reaction sequence described for the preparation of Building block A, the cyclization of the (R)-N-[1-(3-bromo-phenyl)-2-hydroxy-1-methyl-ethyl]-2-chloro-acetamide with potassium tent-butylate yielded the title compound as a white solid. Mass (calculated) $C_{11}H_{12}BrNO_2$ [270.125]; (found) $[M+H]^+$=270, $[M+2-H]^+$=272.

b) (R)-5-(3-Bromo-phenyl)-4-(4-methoxy-benzyl)-5-methyl-morpholin-3-one

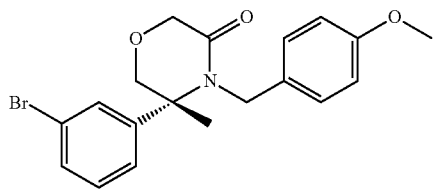

A solution of (R)-5-(3-amino-phenyl)-4-(4-methoxy-benzyl)-5-methyl-morpholin-3-one (1.0 g, 3.7 mmol) in N,N-dimethylformamide was added within 5 minutes at 0° C. to a solution of potassium tert-butanolate (0.636 g, 5.7 mmol). After stirring at 0° C. for 30 minutes the light yellow solution was cooled to −4° C. and treated with a solution of 4-methoxybenzylbromide (1.12 g, 5.6 mmol) in N,N-dimethylformamide (4 ml). The reaction mixture was left to warm to room temperature, then the solvent was evaporated at reduced pressure, and the residue treated with saturated ammonium chloride solution (50 ml) and ethyl acetate (100 ml). The organic layer was separated, washed with brine (50 ml), dried over sodium sulfate, and evaporated at reduced pressure. The crude product was purified by chromatography on silica gel using a gradient of heptane and ethyl acetate=100/0 to 50/50 as the eluent. The (R)-5-(3-bromo-phenyl)-4-(4-methoxy-benzyl)-5-methyl-morpholin-3-one was obtained as colorless oil (1.19 g, 83% of theory). Mass (calculated) $C_{19}H_{20}BrNO_3$ [390.275]; (found) $[M+H]^+$=390, $[M+2-H]^+$=392.

c) (2S,5R)-5-(3-Bromo-phenyl)-4-(4-methoxy-benzyl)-2,5-dimethyl-morpholin-3-one

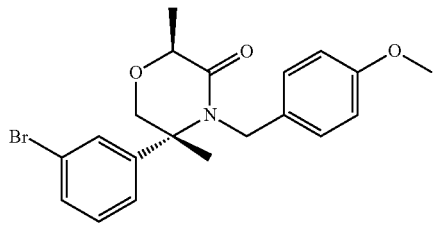

A dried flask was charged under an argon atmosphere with a solution of (R)-5-(3-bromo-phenyl)-4-(4-methoxy-benzyl)-5-methyl-morpholin-3-one (600 mg, 1.5 mmol) in tetrahydrofuran (16 ml) which was cooled to −75° C. Lithium isopropylamine (1.54 ml, 3 mmol) was added, and after the addition of diazomethane (502 mg, 3.5 mmol) the reaction was complete. For the workup, the cold reaction mixture was quenched with a saturated ammonium chloride solution (15 ml) and extracted with a mixture of dichloromethane (40 ml) and water (15 ml). The organic layer was dried over sodium sulfate and evaporated to yield the crude (2S,5R)-5-(3-bromo-phenyl)-4-(4-methoxy-benzyl)-2,5-dimethyl-morpholin-3-one as a brownish oil which was engaged in the next step without further purification. Mass (calculated) $C_{20}H_{22}BrNO_3$ [404.307]; (found) $[M+H]^+$=404, $[M+2-H]^+$=406.

d) (R)-5-(3-Bromo-phenyl)-4-(4-methoxy-benzyl)-2,2,5-trimethyl-morpholin-3-one

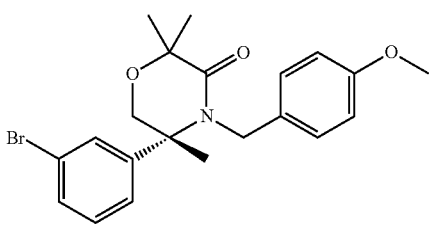

A dried flask was charged under an argon atmosphere with a solution of the crude (2S,5R)-5-(3-bromo-phenyl)-4-(4-methoxy-benzyl)-2,5-dimethyl-morpholin-3-one (622 mg) in tetrahydrofuran (16 ml) which was cooled to −75° C. Lithium diisopropylamide (1.54 ml, 3 mmol) was rapidly added, followed by iodomethane (502 mg, 3.5 mmol). After 15 minutes at −75° C. the reaction was complete. For the workup, the cold reaction mixture was quenched with a saturated ammonium chloride solution (15 ml) and extracted with a mixture of dichloromethane (40 ml) and water (15 ml). The organic layer was dried over sodium sulfate and evaporated. The crude product was purified by chromatography on silica gel using a gradient of heptane and ethyl acetate=100/0 to 66/34 as the eluent. The (R)-5-(3-bromo-phenyl)-4-(4-methoxy-benzyl)-2,2,5-trimethyl-morpholin-3-one was obtained as a white solid (495 mg, 77% of theory). Mass (calculated) $C_{21}H_{24}BrNO_3$ [418.334]; (found) $[M+H]^+=418$, $[M+2-H]^+=420$.

e) (R)-5-(3-Bromo-phenyl)-2,2,5-trimethyl-morpholin-3-one

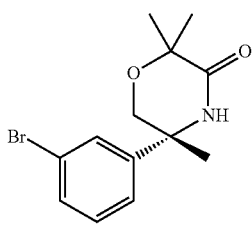

A solution of (R)-5-(3-bromo-phenyl)-4-(4-methoxy-benzyl)-2,2,5-trimethyl-morpholin-3-one (487 mg, 1.2 mmol) and anisole (2.305 g, 21.3 mmol) in trifluoroacetic acid (6 ml) was treated dropwise with trifluoromethanesulfonic acid (1.19 ml). After complete addition, the violet reaction mixture was heated at 73° C. for 23 hours. The cooled reaction mixture was poured into a saturated solution of sodium hydrogencarbonate which was extracted with ethyl acetate. The organic layer was separated, washed with brine, dried over sodium sulfate, and evaporated at reduced pressure. The crude product was purified by chromatography on silica gel using a gradient of heptane and ethyl acetate=100/0 to 66/34 as the eluent. The product containing fractions (550 mg, orange foam) were collected and engaged in the next step without further purification and characterization.

f) (R)-5-[3-(Benzhydrylidene-amino)-phenyl]-2,2,5-trimethyl-morpholin-3-one

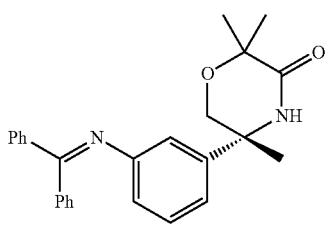

In analogy to step g) in the synthesis of Building block K, the palladium-catalyzed amination of the (R)-5-(3-bromo-phenyl)-2,2,5-trimethyl-morpholin-3-one yielded the title compound as a yellow foam (83% of theory). Mass (calculated) $C_{26}H_{26}N_2O_2$ [398.503]; (found) $[M+H]^+=399$.

g) (R)-5-[3-(Benzhydrylidene-amino)-phenyl]-2,2,5-trimethyl-morpholin-3-thione

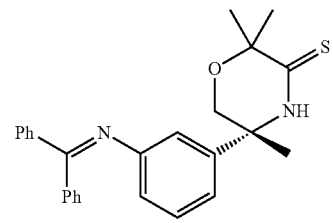

In analogy to step h) in the synthesis of Building block K, the treatment of (R)-5-[3-(benzhydrylidene-amino)-phenyl]-2,2,5-trimethyl-morpholin-3-one with Lawesson's reagent yielded the title compound as a yellow foam after chromatography on silica gel using a gradient of heptane and ethyl acetate=100/0 to 50/50 as the eluent (53% of theory). Mass (calculated) $C_{26}H_{26}N_2OS$ [414.570]; (found) $[M+H]^+=415$.

h) (R)-5-(3-Amino-phenyl)-2,2,5-trimethyl-morpholine-3-thione

In analogy to step h) in the synthesis of Building block K, the hydrolysis of (R)-5-[3-(benzhydrylidene-amino)-phenyl]-2,2,5-trimethyl-morpholin-3-thione with hydrochloric acid yielded the title compound (Building block L) as an off-white solid (86% of theory). Mass (calculated) $C_{13}H_{18}N_2OS$ [250.37]; (found) $[M+H]^+=251$.

Preparation of Building Block M (2R,5R)- and (2S,5S)-5-(5-Amino-2-fluoro-phenyl)-2-benzyl-5-methyl-morpholin-3-one

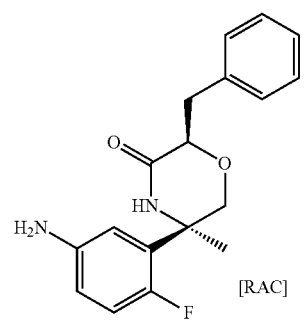

a) (2RS)-Bromo-N-[(RS)-1-(5-bromo-2-fluoro-phenyl)-2-hydroxy-1-methyl-ethyl]-3-phenyl-propionamide

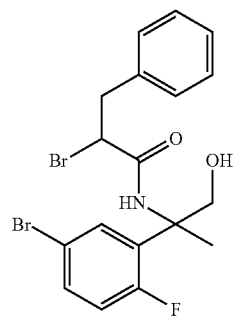

A solution of (RS)-2-amino-2-(5-bromo-2-fluoro-phenyl)-propan-1-ol (1.5 g, 6 mmol) and triethylamine (1.01 ml, 7.3 mmol) in acetonitrile (31 ml) was cooled to 0° C. A solution of (RS)-2-bromo-3-phenyl-propionyl chloride (CAS 42762-86-7) (1.637 g, 6.6 mmol) in acetonitrile was added dropwise. After complete addition the reaction mixture was left to warm to room temperature. After 1 hour the reaction mixture was evaporated under reduced pressure and directly purified by chromatography on silica gel using a gradient of heptane and ethyl acetate=100/0 to 50/50 as the eluent. Besides the N-[(RS)-1-(5-bromo-2-fluoro-phenyl)-2-hydroxy-1-methyl-ethyl]-3-phenyl-acrylamide (0.233 g, 10% of theory), the (2RS)-bromo-N-[(RS)-1-(5-bromo-2-fluoro-phenyl)-2-hydroxy-1-methyl-ethyl]-3-phenyl-propionamide (mixture of diastereoisomers 3:2) was obtained as a white solid (1.985 g, 71.5% of theory). Mass (calculated) $C_{18}H_{18}Br_2FNO_2$ [459.156]; (found) [M+H]$^+$=457, [M+2-H]$^+$=459, [M+4-H]$^+$=461.

b) (2R,5S)-2-Benzyl-5-(5-bromo-2-fluoro-phenyl)-5-methyl-morpholin-3-one and (2S,5R)-2-Benzyl-5-(5-bromo-2-fluoro-phenyl)-5-methyl-morpholin-3-one

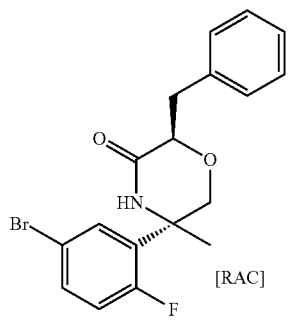

In analogy to the cyclization reaction described for the preparation of Building block C, the reaction of (2RS)-bromo-N-[(RS)-1-(5-bromo-2-fluoro-phenyl)-2-hydroxy-1-methyl-ethyl]-3-phenyl-propionamide with potassium tent-butylate yielded besides the N-[(RS)-1-(5-bromo-2-fluoro-phenyl)-2-hydroxy-1-methyl-ethyl]-3-phenyl-acrylamide (0.381 g, 30% of theory), (2R,5S)-2-benzyl-5-(5-bromo-2-fluoro-phenyl)-5-methyl-morpholin-3-one and (2S,5R)-2-benzyl-5-(5-bromo-2-fluoro-phenyl)-5-methyl-morpholin-3-one as the dominant diastereoisomer in form of a white foam (51% of theory). Mass (calculated) $C_{18}H_{17}BrFNO_2$ [378.244]; (found) [M+H]$^+$=378, [M+2-H]$^+$=380.

c) (2R,5S)- and (2S,5R)-5-[5-(Benzhydrylidene-amino)-2-fluoro-phenyl]-2-benzyl-5-methyl-morpholin-3-one and (2R,5R)- and (2S,5S)-5-[5-(Benzhydrylidene-amino)-2-fluoro-phenyl]-2-benzyl-5-methyl-morpholin-3-one

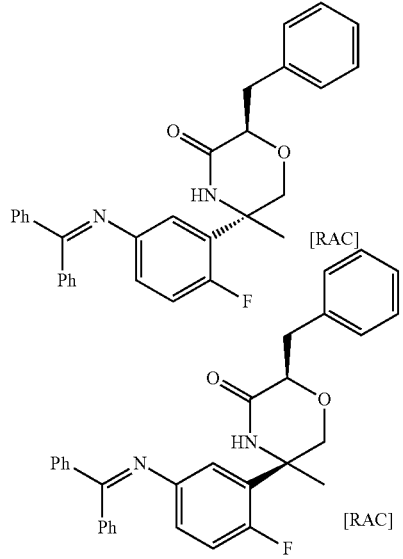

In analogy to step g) in the synthesis of Building block K, the palladium-catalyzed amination of the (2R,5S)-2-benzyl-5-(5-bromo-2-fluoro-phenyl)-5-methyl-morpholin-3-one and (2S,5R)-2-benzyl-5-(5-bromo-2-fluoro-phenyl)-5-methyl-morpholin-3-one yielded the title compounds. After chromatography on silica gel using a gradient of heptane and ethyl acetate=100/0 to 50/50 as the eluent the first eluting (2R,5S)- and (2S,5R)-5-[5-(benzhydrylidene-amino)-2-fluoro-phenyl]-2-benzyl-5-methyl-morpholin-3-one was obtained as a yellow foam (43% of theory). Mass (calculated) $C_{31}H_{27}FN_2O_2$ [478.564]; (found) [M+H]$^+$=479. The second eluting (2R,5R)- and (2S,5S)-5-[5-(benzhydrylidene-amino)-2-fluoro-phenyl]-2-benzyl-5-methyl-morpholin-3-one was obtained as a light yellow foam (48% of theory). Mass (calculated) $C_{31}H_{27}FN_2O_2$ [478.564]; (found) [M+H]$^+$= 479.

d) (2R,5R)- and (2S,5S)-5-(5-Amino-2-fluoro-phenyl)-2-benzyl-5-methyl-morpholin-3-one

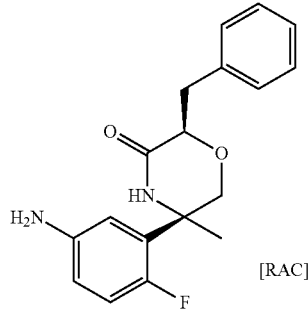

A solution of (2R,5R)- and (2S,5S)-5-[5-(benzhydrylidene-amino)-2-fluoro-phenyl]-2-benzyl-5-methyl-morpholin-3-one (359 mg, 0.8 mmol) in dioxane (6 ml) was cooled to 15° C. and treated with hydrochloric acid (1 N, 0.9 mmol). The reaction mixture was left to warm to room temperature and stirred for another 2 hours. For the workup, the solution was evaporated at reduced pressure and the residue treated with dichloromethane (20 ml) and Huenig's base (0.219 ml). The yellow solution was extracted with water (2×10 ml). The aqueous layer was separated, basified to pH 9 with Huenig's base and re-extracted with dichloromethane (3×10 ml). The four organic layers were combined, dried over sodium sulfate and evaporated. After chromatography on a Silicycle-Si-amine phase using a gradient of dichloromethane and methanol=100/0 to 99/1 the (2R,5R)- and (2S,5S)-5-(5-amino-2-fluoro-phenyl)-2-benzyl-5-methyl-morpholin-3-one was obtained as a white foam (169 mg, 72% of theory). Mass (calculated) $C_{18}H_{19}FN_2O_2$ [314.363]; (found) $[M+H]^+=315$.

Preparation of Building Block N (2S,5R)- and (2R,5S)-5-(5-Amino-2-fluoro-phenyl)-2-benzyl-5-methyl-morpholin-3-one

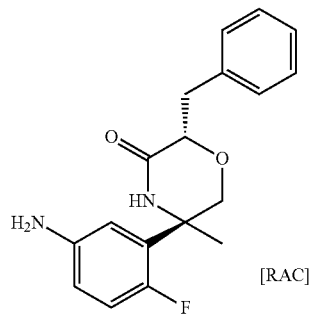

In a procedure analogous to step d) in the preparation of Building block M the acidic hydrolysis of (2R,5S)- and (2S,5R)-5-[5-(benzhydrylidene-amino)-2-fluoro-phenyl]-2-benzyl-5-methyl-morpholin-3-one yielded the title compound as an off-white foam. Mass (calculated) $C_{18}H_{19}FN_2O_2$ [314.363]; (found) $[M+H]^+=315$.

Preparation of Building block O (RS)-5-(5-Amino-2-fluoro-phenyl)-5-methyl-morpholine-3-thione hydrochloride

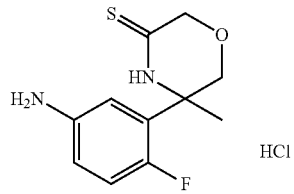

In a reaction sequence analogous to that described for the preparation of the optically active Building block H, the cyclization of the (RS)-N-[1-(5-bromo-2-fluoro-phenyl)-2-hydroxy-1-methyl-ethyl]-2-chloro-acetamide with potassium tent-butylate, followed by the palladium-catalyzed amination yielded the (RS)-5-[5-(benzhydrylidene-amino)-2-fluoro-phenyl]-5-methyl-morpholin-3-one. Its reaction with Lawesson's reagent and the following treatment with hydrochloric acid yielded the title compound as a light yellow solid. Mass (calculated) $C_{11}H_{13}FN_2OS.ClH$ [276.762]; (found) $[M+H]^+=241$.

Preparation of Building Block P (RS)-5-(5-Amino-2-fluoro-phenyl)-5-methyl-5,6-dihydro-2H-[1,4]oxazin-3-ylamine dihydrochloride

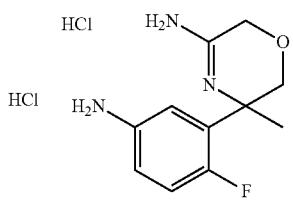

In a reaction sequence analogous to that described for the optically active analogue Building block Q, the (RS)-5-[5-(benzhydrylidene-amino)-2-fluoro-phenyl]-5-methyl-morpholine-3-thione was transformed into the title compound which was obtained as a light brown foam. Mass (calculated) $C_{11}H_{14}FN_3O.2ClH$ [296.174]; (found) $[M+H]^+=224$.

Preparation of Building Block Q (R)-5-(5-Amino-2-fluoro-phenyl)-5-methyl-5,6-dihydro-2H-[1,4]oxazin-3-ylamine

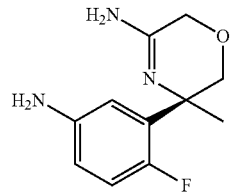

A suspension of (R)-5-[5-(benzhydrylidene-amino)-2-fluoro-phenyl]-5-methyl-morpholine-3-thione [Building block H, step b)] (1.25 g, 3.09 mmol) in methanol (57 ml) was treated with a solution of ammonia in methanol (26.5 ml, 185 mmol) and a solution of tert-butyl-hydroperoxide (4.28 ml, 30.9 mmol). After stirring at room temperature for 40 hours, the reaction mixture was diluted with water and extracted three times with dichloromethane. The combined organic layers were washed with water, dried over sodium sulfate, evaporated, and dried at high vacuum at room temperature to yield the crude (R)-5-[5-(benzhydrylidene-amino)-2-fluoro-phenyl]-5-methyl-5,6-dihydro-2H-[1,4]oxazin-3-ylamine as a light brown foam which was dissolved in dioxane (20 ml) and treated with hydrochloric acid (1 M, 3.09 ml). After 40 minutes at room temperature the reaction mixtures was diluted with a saturated solution of hydrogen-carbonate and water. The mixture was extracted three times with ethyl acetate, then the aqueous phase basified with a solution of sodium hydroxide (28%). After four extractions with dichloromethane, the organic layers were combined, dried over sodium sulfate and evaporated. The (R)-5-(5-amino-2-fluoro-phenyl)-5-methyl-5,6-dihydro-2H-[1,4]oxazin-3-ylamine was obtained as an off-white waxy solid (445 mg, 64% of theory).

Preparation of Building Block R

(2R,5R)-5-(5-Amino-2-fluoro-phenyl)-5-methyl-2-phenyl-morpholin-3-one hydrochloride

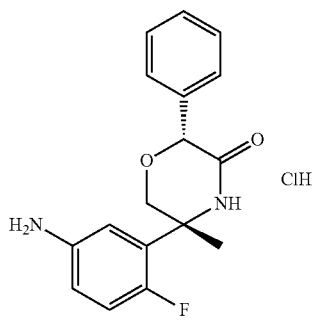

a) (R)-2-(5-bromo-2-fluoro-phenyl)-2-(4-methoxy-benzylamino)-propan-1-ol

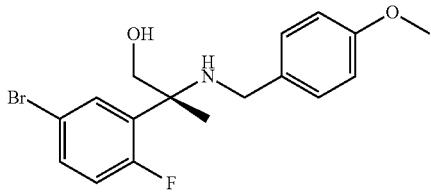

A solution of (R)-2-amino-2-(5-bromo-2-fluoro-phenyl)-propan-1-ol (5.0 g, 20.2 mmol) and 4-methoxybenzaldehyde (2.8 g, 20.2 mmol) in 1,2-dichloroethane (150 ml) was treated with sodium triacetoxyborohydride (8.81 g, 40.3 mmol) at room temperature. TLC check (eluent: heptane:ethyl acetate=1:1) showed complete reaction after 30 minutes. For the workup, to the reaction mixture were added ethyl acetate (250 ml) and saturated sodium hydrogen-carbonate solution (100 ml). The aqueous layer was separated, and then extracted with ethyl acetate (250 ml). The combined organic layers were washed with saturated sodium chloride solution (100 ml), thereafter dried over sodium sulfate and evaporated at reduced pressure. After chromatography on Silicycle-Si-amine column using a gradient of heptane and ethyl acetate=100/0 to 50/50 as the eluent, (R)-2-(5-bromo-2-fluoro-phenyl)-2-(4-methoxy-benzylamino)-propan-1-ol was obtained as a colorless oil (7.29 g, 98% of theory). Mass (calculated) $C_{17}H_{19}BrFNO_2$ [368.25]; (found) $[M+H]^+=368$, $[M+2-H]^+=370$.

b) [(R)-1-(5-bromo-2-fluoro-phenyl)-2-(tert-butyl-dimethyl-silanyloxy)-1-methyl-ethyl]-(4-methoxy-benzyl)-amine

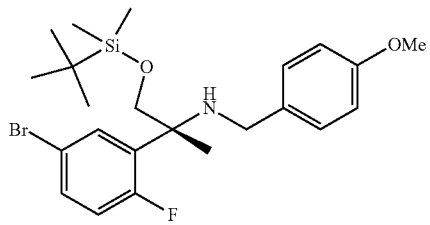

A solution of (R)-2-(5-bromo-2-fluoro-phenyl)-2-(4-methoxy-benzylamino)-propan-1-ol (6.95 g, 18.9 mmol) in dichloromethane (170 ml) was treated at room temperature with triethylamine (5.78 ml, 41.5 mmol), 4-dimethylaminopyridine (1.15 g, 9.43 mmol), and tert-butyldimethylchlorosilane (1.15 g, 37.7 mmol). After 16 hours at room temperature the reaction mixture was consecutively extracted with saturated sodium hydrogen-carbonate solution (100 ml), water (100 ml), and brine (100 ml). The aqueous layers were re-extracted with dichloromethane (100 ml). The combined organic layers were dried over sodium sulfate and evaporated at reduced pressure. After chromatography on Silicycle-Si-amine column using heptane as the eluent, [(R)-1-(5-bromo-2-fluoro-phenyl)-2-(tert-butyl-dimethyl-silanyloxy)-1-methyl-ethyl]-(4-methoxy-benzyl)-amine was obtained as a colorless oil (8.0 g, 88% of theory). Mass (calculated) $C_{23}H_{33}BrFNO_2Si$ [482.51]; (found) $[M+H]^+=482$, $[M+2-H]^+=484$.

c) (RS)-N-[(R)-1-(5-Bromo-2-fluoro-phenyl)-2-(tert-butyl-dimethyl-silanyloxy)-1-methyl-ethyl]-2-chloro-N-(4-methoxy-benzyl)-2-phenyl-acetamide

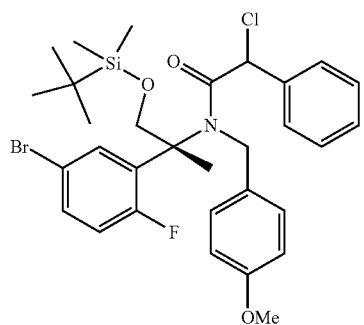

A solution of [(R)-1-(5-bromo-2-fluoro-phenyl)-2-(tert-butyl-dimethyl-silanyloxy)-1-methyl-ethyl]-(4-methoxy-benzyl)-amine (1.035 g, 2.15 mmol) in acetonitrile (16 ml) was treated with triethylamine (0.36 ml, 2.57 mmol). The mixture was cooled to 10° C. and a solution of (RS)-2-chloro-2-phenyl-acetyl chloride (0.34 ml, 2.36 mmol) in acetonitrile (2 ml) was added slowly. The reaction mixture was allowed to warm to room temperature and was stirred for 3 hours. Because the transformation was not complete, triethylamine (0.33 ml, 2.36 mmol) was again added, the reaction mixture cooled to −5° C., then treated with a solution of (RS)-2-chloro-2-phenyl-acetyl chloride (0.31 ml, 2.15 mmol) in acetonitrile (1 ml). The reaction mixture was allowed to warm to room temperature and was stirred for 22 hours. Thereafter, the mixture was evaporated at reduced pressure and without further workup directly purified by chromatography on Silicycle-Si-amine column using a gradient of heptane and ethyl acetate=100/0 to 70/30 as the eluent. (RS)-N-[(R)-1-(5-bromo-2-fluoro-phenyl)-2-(tert-butyl-dimethyl-silanyloxy)-1-methyl-ethyl]-2-chloro-N-(4-methoxy-benzyl)-2-phenyl-acetamide was obtained as a white foam (1.068 g, 78% of theory). Mass (calculated) $C_{31}H_{38}BrClFNO_3$ [635.09]; (found) $[M+H]^+=638$, $[M+2-H]^+=636$, $[M+4-H]^+=634$.

d) (2RS,5R)-5-(5-Bromo-2-fluoro-phenyl)-4-(4-methoxy-benzyl)-5-methyl-2-phenyl-morpholin-3-one

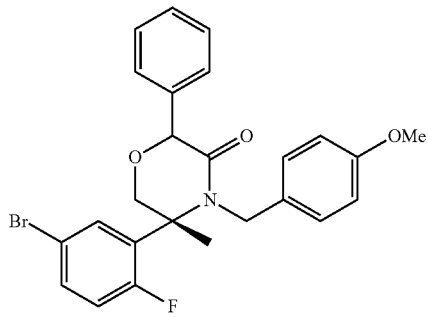

A solution of (RS)-N-[(R)-1-(5-bromo-2-fluoro-phenyl)-2-(tert-butyl-dimethyl-silanyloxy)-1-methyl-ethyl]-2-chloro-N-(4-methoxy-benzyl)-2-phenyl-acetamide (1.068 g, 1.68 mmol) in tetrahydrofuran (30 ml) was cooled to 0° C. and treated dropwise during 10 minutes with a solution of tetrabutylammonium fluoride (1 M, 3.36 mmol) in tetrahydrofuran. The orange-colored reaction mixture was stirred at 0° C. for 5 minutes, then for 4 hours at room temperature. For the workup, the reaction mixture was evaporated at reduced pressure, the residue partitioned between water (10 ml) and ethyl acetate (25 ml) and stirred for 15 minutes. The layers were separated and the aqueous layer re-extracted with ethyl acetate (25 ml). The combined organic layers were dried over sodium sulfate and evaporated at reduced pressure. After chromatography on a Silicycle-Si-amine column using a gradient of heptane and ethyl acetate=100/0 to 50/50 as the eluent, the (2RS,5R)-5-(5-bromo-2-fluoro-phenyl)-4-(4-methoxy-benzyl)-5-methyl-2-phenyl-morpholin-3-one was obtained as a white foam (369 mg, 45% of theory). Mass (calculated) $C_{25}H_{23}BrFNO_3$ [484.37]; (found) $[M+H]^+=484$, $[M+2-H]^+=486$.

e) (2RS,5R)-5-(5-Bromo-2-fluoro-phenyl)-5-methyl-2-phenyl-morpholin-3-one

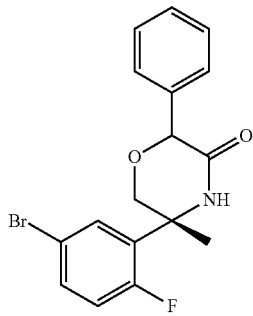

In a manner analogous to that described for the preparation of building black L d) the cleavage of the 4-methoxybenzyl group with trifluoromethanesulfonic acid yielded the title compound as the main component after flashchromatography on silica gel using a gradient of heptane and ethyl acetate=100/0 to 35/65 as the eluent. Mass (calculated) $C_{17}H_{15}BrFNO_2$ [364.22]; (found) $[M+H]^+=364$, $[M+2-H]^+=366$. The crude material was engaged in the next step without further purification.

f) (2R,5R)-5-[5-(Benzhydrylidene-amino)-2-fluoro-phenyl]-5-methyl-2-phenyl-morpholin-3-one and (2S,5R)-5-[5-(Benzhydrylidene-amino)-2-fluoro-phenyl]-5-methyl-2-phenyl-morpholin-3-one

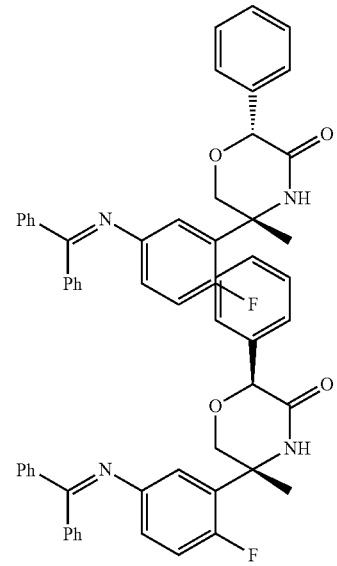

In analogy to step g) in the synthesis of Building block K, the palladium-catalyzed amination of the (2RS,5R)-5-(5-bromo-2-fluoro-phenyl)-5-methyl-2-phenyl-morpholin-3-one produced the diastereomeric mixture of the imines which was separated by chromatography on silica gel using a gradient of heptane and ethyl acetate=100/0 to 50/50 as the eluent yielding the (2R,5R)-5-[5-(benzhydrylidene-amino)-2-fluoro-phenyl]-5-methyl-2-phenyl-morpholin-3-one as the first eluting diastereoisomer (35% of theory) and the (2S,5R)-5-[5-(benzhydrylidene-amino)-2-fluoro-phenyl]-5-methyl-2-phenyl-morpholin-3-one as the second eluting diastereoisomer (40% of theory) both as a yellow foam. Mass (calculated) $C_{30}H_{25}FN_2O_2$ [464.54]; (found) $[M+H]^+=465$.

g) (2R,5R)-5-(5-Amino-2-fluoro-phenyl)-5-methyl-2-phenyl-morpholin-3-one hydrochloride

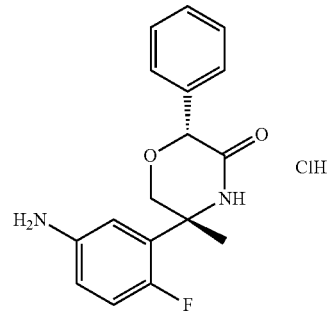

In a procedure analogous to step d) in the preparation of Building block M the acidic hydrolysis of (2R,5R)-5-[5-(benzhydrylidene-amino)-2-fluoro-phenyl]-5-methyl-2-phenyl-morpholin-3-one yielded the title compound as an off-white solid (58% of theory). Mass (calculated) $C_{17}H_{17}FN_2O_2 \cdot HCl$ [336.80]; (found) $[M+H]^+=301$.

Preparation of Building Block S (2S,5R)-5-(5-Amino-2-fluoro-phenyl)-5-methyl-2-phenyl-morpholin-3-one Hydrochloride

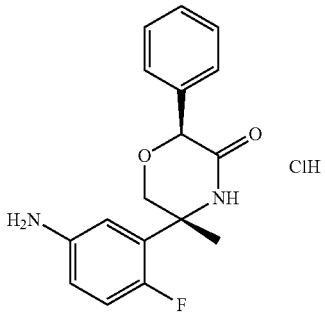

In a procedure analogous to step d) in the preparation of Building block M the acidic hydrolysis of (2S,5R)-5-[5-(benzhydrylidene-amino)-2-fluoro-phenyl]-5-methyl-2-phenyl-morpholin-3-one yielded the title compound as a red solid (80% of theory). Mass (calculated) $C_{17}H_{17}FN_2O_2 \cdot HCl$ [336.80]; (found) $[M+H]^+=301$.

Example 1

Method A (RS)-3,5-Difluoro-pyridine-2-carboxylic acid [3-(5-amino-3-methyl-3,6-dihydro-2H-[1,4]oxazin-3-yl)-phenyl]-amide (=3,5-Difluoro-pyridine-2-carboxylic acid [3-((RS)-5-amino-3-methyl-3,6-dihydro-2H-[1,4]oxazin-3-yl)-phenyl]-amide)

a) (RS)-3,5-Difluoro-pyridine-2-carboxylic acid [3-(3-methyl-5-oxo-morpholin-3-yl)-phenyl]-amide (=3,5-Difluoro-pyridine-2-carboxylic acid [3-((RS)-3-methyl-5-oxo-morpholin-3-yl)-phenyl]-amide)

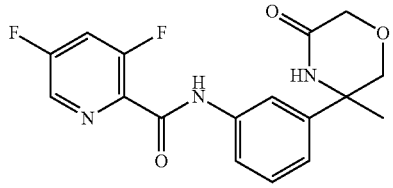

A solution of (RS)-3,5-difluoropyridin-2-carboxylic acid (0.186 g, 1.2 mmol) in N,N-dimethylformamide (7 ml) was cooled to 0° C. Consecutively, 1-hydroxybenzotriazole hydrate (0.199 g, 1.5 mmol), O-(benzotriazol-1-yl)-N,N,N',N'-tetramethyluronium hexafluorophosphate (0.547 g, 1.4 mmol), (RS)-5-(3-amino-phenyl)-5-methyl-morpholin-3-one hydrochloride (0.250 g, 1.0 mmol), and N-ethyldiisopropylamine (0.466 g, 3.6 mmol) were added, and the mixture was stirred at 0° C. for 10 minutes, then left at room temperature for 16 hours. For the workup, the reaction mixture was evaporated to dryness and the residue directly purified by chromatography on an Isolute flash NH$_2$ column using a gradient of heptane/ethyl acetate=100/0 to 33/66 as the eluent. There were obtained 0.39 g (86% of theory) of (RS)-3,5-difluoro-pyridine-2-carboxylic acid [3-(3-methyl-5-oxo-morpholin-3-yl)-phenyl]-amide (=3,5-difluoro-pyridine-2-carboxylic acid [3-((RS)-3-methyl-5-oxo-morpholin-3-yl)-phenyl]-amide) as a white solid. Mass (calculated) $C_{17}H_{15}F_2N_3O_3$ [347.324]; (found) $[M+H]^+=348$.

b) (RS)-3,5-Difluoro-pyridine-2-carboxylic acid [3-(5-ethoxy-3-methyl-3,6-dihydro-2H-[1,4]oxazin-3-yl)-phenyl]-amide (=3,5-Difluoro-pyridine-2-carboxylic acid [3-((RS)-5-ethoxy-3-methyl-3,6-dihydro-2H-[1,4]oxazin-3-yl)-phenyl]-amide)

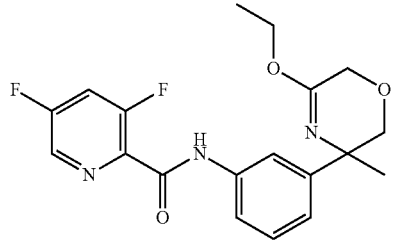

In a dried flask, a dispersion of (RS)-3,5-difluoro-pyridine-2-carboxylic acid [3-(3-methyl-5-oxo-morpholin-3-yl)-phenyl]-amide (0.305 g, 0.9 mmol) in dichloromethane (80 ml) was treated with triethyloxonium tetrafluoroborate (0.172 g, 0.9 mmol) under argon at room temperature during 16 hours. For the workup, the reaction mixture was extracted with a saturated solution of sodium hydrogen-carbonate (40 ml), the organic layer separated and dried over sodium sulfate. After evaporation, a mixture of (RS)-3,5-difluoro-pyridine-2-carboxylic acid [3-(5-ethoxy-3-methyl-3,6-dihydro-2H-[1,4]oxazin-3-yl)-phenyl]-amide and (RS)-3,5-difluoro-pyridine-2-carboxylic acid [3-(3-methyl-5-oxo-morpholin-3-yl)-phenyl]-amide (=3,5-difluoro-pyridine-2-carboxylic acid [3-((RS)-3-methyl-5-oxo-morpholin-3-yl)-phenyl]-amide) (25%) was obtained as a light yellow foam (0.356 g). The crude product was engaged in the next step without further purification.

c) (RS)-3,5-Difluoro-pyridine-2-carboxylic acid [3-(5-amino-3-methyl-3,6-dihydro-2H-[1,4]oxazin-3-yl)-phenyl]-amide (=3,5-Difluoro-pyridine-2-carboxylic acid [3-((RS)-5-amino-3-methyl-3,6-dihydro-2H-[1,4]oxazin-3-yl)-phenyl]-amide)

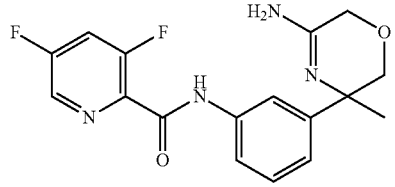

A dried pressure tube was charged under an argon atmosphere with a dispersion of (RS)-3,5-difluoro-pyridine-2-carboxylic acid [3-(5-ethoxy-3-methyl-3,6-dihydro-2H-[1,4]oxazin-3-yl)-phenyl]-amide (0.348 g, 0.9 mmol) and ammonium chloride (0.182 g, 3.4 mmol) in methanol (10 ml). The sealed pressure tube was heated at 100° C. for 16 hours. After cooling, the reaction mixture was evaporated to dryness and directly purified by chromatography on an Isolute flash NH$_2$ column using a gradient of dichloromethane/methanol=100/0 to 95/5 as the eluent. There were obtained 0.076 g (38% of theory) of (RS)-3,5-difluoro-pyridine-2-carboxylic acid [3-(3-methyl-5-oxo-morpholin-3-yl)-phenyl]-amide (=3,5-difluoro-pyridine-2-carboxylic acid [3-((RS)-3-methyl-5-oxo-morpholin-3-yl)-phenyl]-amide) as a white solid; mass (calculated) $C_{17}H_{15}F_2N_3O_3$ [347.324]; (found) $[M+H]^+=348$, and 0.113 g (57% of theory) of (RS)-3,5- difluoro-pyridine-2-carboxylic acid [3-(5-amino-3-methyl-3,6-dihydro-2H-[1,4]oxazin-3-yl)-phenyl]-amide (1) as a light yellow foam; mass (calculated) $C_{17}H_{16}F_2N_4O_2$ [346.340]; (found) [M+H]$^+$=347.

Examples 2-17

In a reaction sequence analogous to that described in Example 1 (method A), the following compounds were obtained starting from the condensation of the corresponding acid with Building block A, (RS)-5-(3-amino-phenyl)-5-methyl-morpholin-3-one hydrochloride, followed by the treatment with triethyloxonium tetrafluoroborate or trimethyloxonium tetrafluoroborate and ammonium chloride:

Example 2

With 3,5-dichloro-pyridine-2-carboxylic acid the (RS)-3,5-dichloro-pyridine-2-carboxylic acid [3-(5-amino-3-methyl-3,6-dihydro-2H-[1,4]oxazin-3-yl)-phenyl]-amide (=3,5-dichloro-pyridine-2-carboxylic acid [3-((RS)-5-amino-3-methyl-3,6-dihydro-2H-[1,4]oxazin-3-yl)-phenyl]-amide) (2) as a light yellow foam; (calculated) $C_{17}H_{16}Cl_2N_4O_2$ [379.245]; (found) [M+H]$^+$=379, [M+2-H]$^+$=381;

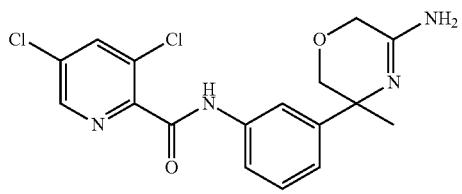

Example 3

With 4-chloro-2-fluoro-benzoic acid the (RS)-N-[3-(5-amino-3-methyl-3,6-dihydro-2H-[1,4]oxazin-3-yl)-phenyl]-4-chloro-2-fluoro-benzamide (3) as a white foam; (calculated) $C_{18}H_{17}ClFN_3O_2$ [361.802]; (found) [M+H]$^+$=362;

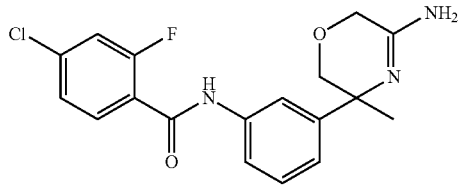

Example 4

With 2,4-dichloro-benzoic acid the (RS)-N-[3-(5-amino-3-methyl-3,6-dihydro-2H-[1,4]oxazin-3-yl)-phenyl]-2,4-dichloro-benzamide (4) as a white solid; (calculated) $C_{18}H_{17}Cl_2N_3O_2$ [378.257]; (found) [M+H]$^+$=378, [M+2-H]$^+$=380;

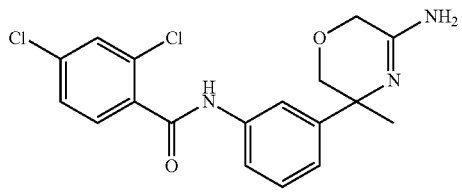

Example 5

With 2,5-difluoro-benzoic acid the (RS)-N-[3-(5-amino-3-methyl-3,6-dihydro-2H-[1,4]oxazin-3-yl)-phenyl]-2,5-difluoro-benzamide (5) as a white foam; (calculated) $C_{18}H_{17}F_2N_3O_2$ [345.347]; (found) [M+H]$^+$=346;

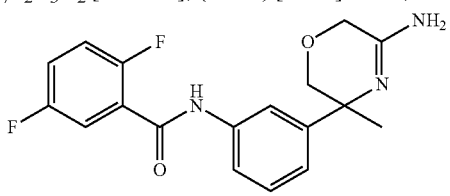

Example 6

With 3-chloro-benzoic acid the (RS)-N-[3-(5-amino-3-methyl-3,6-dihydro-2H-[1,4]oxazin-3-yl)-phenyl]-3-chloro-benzamide (6) as a white foam; (calculated) $C_{18}H_{18}ClN_3O_2$ [343.820]; (found) [M+H]$^+$=344, [M+2-H]$^+$=346;

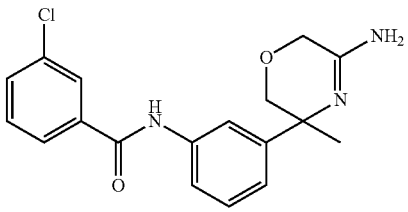

Example 7

With 5-chloro-pyridine 2-carboxylic acid the (RS)-5-chloro-pyridine-2-carboxylic acid [3-(5-amino-3-methyl-3,6-dihydro-2H-[1,4]oxazin-3-yl)-phenyl]-amide (=5-chloro-pyridine-2-carboxylic acid [3-((RS)-5-amino-3-methyl-3,6-dihydro-2H-[1,4]oxazin-3-yl)-phenyl]-amide) (7) as a white foam; (calculated) $C_{17}H_{17}ClN_4O_2$ [344.804]; (found) [M+H]$^+$=345;

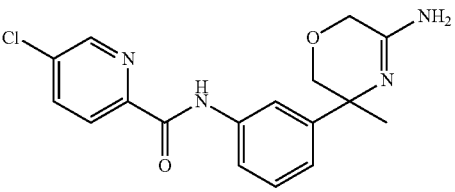

Example 8

With 5-chloro-thiophene-2-carboxylic acid the (RS)-5-chloro-thiophene-2-carboxylic acid [3-(5-amino-3-methyl-3,6-dihydro-2H-[1,4]oxazin-3-yl)-phenyl]-amide (=5-chloro-thiophene-2-carboxylic acid [3-((RS)-5-amino-3-methyl-3,6-dihydro-2H-[1,4]oxazin-3-yl)-phenyl]-amide) (8) as a light yellow solid; (calculated) $C_{16}H_{16}ClN_3O_2S$ [349.842]; (found) [M+H]$^+$=350;

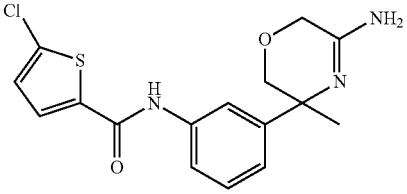

Example 9

With 2,5-dimethyl-thiophene-3-carboxylic acid the (RS)-2,5-dimethyl-thiophene-3-carboxylic acid [3-(5-amino-3- methyl-3,6-dihydro-2H-[1,4]oxazin-3-yl)-phenyl]-amide (=2,5-dimethyl-thiophene-3-carboxylic acid [3-((RS)-5-amino-3-methyl-3,6-dihydro-2H-[1,4]oxazin-3-yl)-phenyl]-amide) (9) as a white solid; (calculated) $C_{18}H_{21}N_3O_2S$ [343.449]; (found) $[M+H]^+=344$;

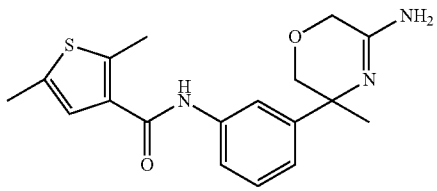

Example 10

With 2-methyl-thiazole-4-carboxylic acid the (RS)-2-methyl-thiazole-4-carboxylic acid [3-(5-amino-3-methyl-3,6-dihydro-2H-[1,4]oxazin-3-yl)-phenyl]-amide (=2-methyl-thiazole-4-carboxylic acid [3-((RS)-5-amino-3-methyl-3,6-dihydro-2H-[1,4]oxazin-3-yl)-phenyl]-amide) (10) as a light yellow solid; (calculated) $C_{16}H_{18}N_4O_2S$ [330.41]; (found) $[M+H]^+=331$;

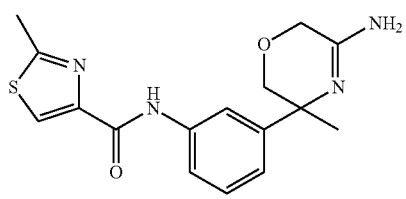

Example 11

With 2,5-dimethyl-1,3-oxazole-4-carboxylic acid the (RS)-2,5-dimethyl-oxazole-4-carboxylic acid [3-(5-amino-3-methyl-3,6-dihydro-2H-[1,4]oxazin-3-yl)-phenyl]-amide (=2,5-dimethyl-oxazole-4-carboxylic acid [3-((RS)-5-amino-3-methyl-3,6-dihydro-2H-[1,4]oxazin-3-yl)-phenyl]-amide) (11) as a white foam; (calculated) $C_{17}H_{20}N_4O_3$ [328.37]; (found) $[M+H]^+=329$;

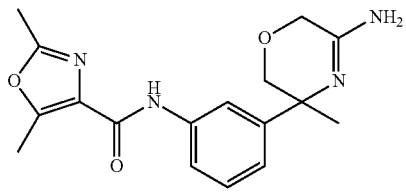

Example 12

With 2-methyl-1,3-oxazole-4-carboxylic acid the (RS)-2-methyl-oxazole-4-carboxylic acid [3-(5-amino-3-methyl-3,6-dihydro-2H-[1,4]oxazin-3-yl)-phenyl]-amide (=2-methyl-oxazole-4-carboxylic acid [3-((RS)-5-amino-3-methyl-3,6-dihydro-2H-[1,4]oxazin-3-yl)-phenyl]-amide) (12) as a light yellow solid; (calculated) $C_{16}H_{18}N_4O_3$ [314.34]; (found) $[M+H]^+=315$;

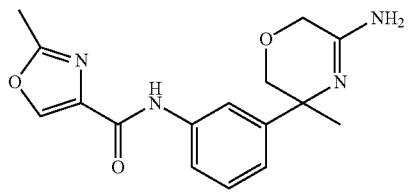

Example 13

With 2,5-dimethylfuran-3-carboxylic acid the (RS)-2,5-dimethylfuran-3-carboxylic acid [3-(5-amino-3-methyl-3,6-dihydro-2H-[1,4]oxazin-3-yl)-phenyl]-amide (=2,5-dimethylfuran-3-carboxylic acid [3-((RS)-5-amino-3-methyl-3,6-dihydro-2H-[1,4]oxazin-3-yl)-phenyl]-amide) (13) as a white soli; (calculated) $C_{18}H_{21}N_3O_3$ [327.38]; (found) $[M+H]^+=328$;

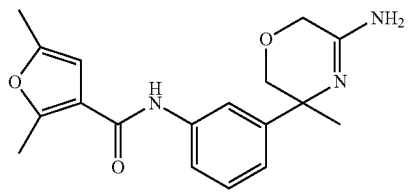

Example 14

With 1-(2,2,2-trifluoro-ethyl)-1H-pyrazole-3-carboxylic acid the (RS)-1-(2,2,2-trifluoro-ethyl)-1H-pyrazole-3-carboxylic acid [3-(5-amino-3-methyl-3,6-dihydro-2H-[1,4]oxazin-3-yl)-phenyl]-amide (=1-(2,2,2-trifluoro-ethyl)-1H-pyrazole-3-carboxylic acid [3-((RS)-5-amino-3-methyl-3,6-dihydro-2H-[1,4]oxazin-3-yl)-phenyl]-amide) (14) as a white foam; (calculated) $C_{17}H_{18}F_3N_5O_2$ [381.36]; (found) $[M+H]^+=382$;

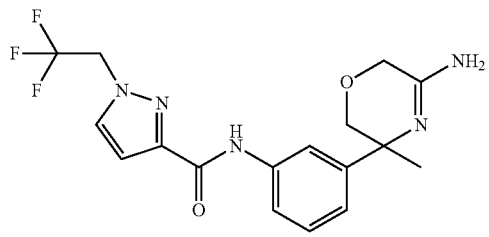

Example 15

With 1-methyl-1H-indazole-3-carboxylic acid the (RS)-1-methyl-1H-indazole-3-carboxylic acid [3-(5-amino-3-methyl-3,6-dihydro-2H-[1,4]oxazin-3-yl)-phenyl]-amide (=1-methyl-1H-indazole-3-carboxylic acid [3-((RS)-5-amino-3-methyl-3,6-dihydro-2H-[1,4]oxazin-3-yl)-phenyl]-amide) (15) as a white foam; (calculated) $C_{20}H_{21}N_5O_2$ [363.42]; (found) $[M+H]^+=364$;

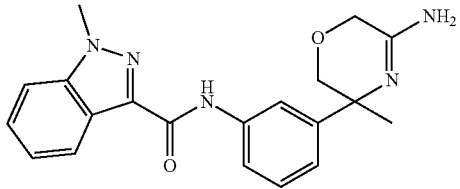

Example 16

With pyrazolo[1,5-a]pyridine-2-carboxylic acid the (RS)-Pyrazolo[1,5-a]pyridine-2-carboxylic acid [3-(5-amino-3-methyl-3,6-dihydro-2H-[1,4]oxazin-3-yl)-phenyl]-amide (=Pyrazolo[1,5-a]pyridine-2-carboxylic acid [3-((RS)-5-amino-3-methyl-3,6-dihydro-2H-[1,4]oxazin-3-yl)-phenyl]-amide) (16) as a white solid; (calculated) $C_{19}H_{19}N_5O_2$ [349.392]; (found) $[M+H]^+=350$;

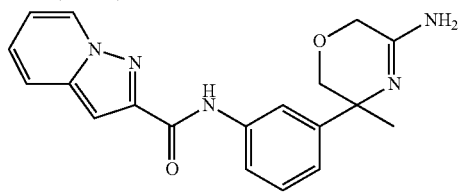

Example 17

With 4-chloro-2-iodo-benzoic acid the (RS)-N-[3-(5-amino-3-methyl-3,6-dihydro-2H-[1,4]oxazin-3-yl)-phenyl]-4-chloro-2-iodo-benzamide (17) as a light yellow solid; (calculated) $C_{18}H_{17}ClIN_3O_2$ [469.713]; (found) $[M+H]^+=470$;

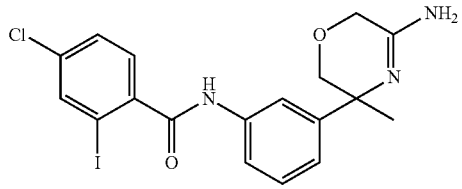

Example 18

In a reaction sequence analogous to that described in Example 1 (method A), the following compound was obtained starting from the condensation of the corresponding acid with Building block B, (R)-5-(3-amino-phenyl)-5-methyl-morpholin-3-one hydrochloride, followed by the treatment with triethyloxonium tetrafluoroborate or trimethyloxonium tetrafluoroborate and ammonium chloride:
With 5-chloro-pyridine 2-carboxylic acid the (R)-5-chloro-pyridine-2-carboxylic acid [3-(5-amino-3-methyl-3,6-dihydro-2H-[1,4]oxazin-3-yl)-phenyl]-amide (=5-chloro-pyridine-2-carboxylic acid [3-((R)-5-amino-3-methyl-3,6-dihydro-2H-[1,4]oxazin-3-yl)-phenyl]-amide) (18) as a white foam; (calculated) $C_{17}H_{17}ClN_4O_2$ [344.804]; (found) $[M+H]^+=345$;

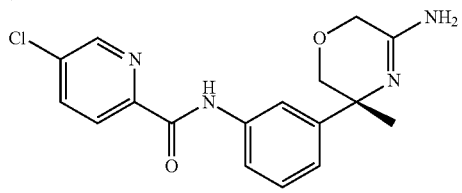

Examples 19-20

In a reaction sequence analogous to that described in Example 1 (method A), the following compounds were obtained starting from the condensation of the corresponding acid with Building block C, (RS)-5-(5-amino-2-fluoro-phenyl)-5-methyl-morpholin-3-one hydrochloride, followed by the treatment with triethyloxonium tetrafluoroborate or trimethyloxonium tetrafluoroborate and ammonium chloride:

Example 19

With 4-chloro-benzoic acid the (RS)-N-[3-(5-amino-3-methyl-3,6-dihydro-2H-[1,4]oxazin-3-yl)-4-fluoro-phenyl]-4-chloro-benzamide (19) as a light yellow solid; (calculated) $C_{18}H_{17}ClFN_3O_2$ [361.802]; (found) $[M+H]^+=362$;

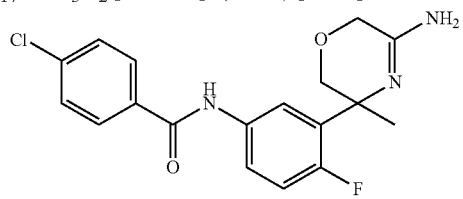

Example 20

With 5-chloro-pyridine 2-carboxylic acid the (RS)-5-chloro-pyridine-2-carboxylic acid [3-(5-amino-3-methyl-3,6-dihydro-2H-[1,4]oxazin-3-yl)-4-fluoro-phenyl]-amide (=5-chloro-pyridine-2-carboxylic acid [3-((RS)-5-amino-3-methyl-3,6-dihydro-2H-[1,4]oxazin-3-yl)-4-fluoro-phenyl]-amide) (20) as a light yellow solid; (calculated) $C_{17}H_{16}ClFN_4O_2$ [362.794]; (found) $[M+H]^+=363$;

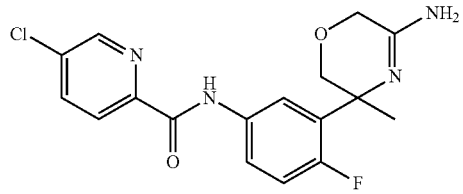

Example 21

In a reaction sequence analogous to that described in Example 1 (method A), the following compound was obtained starting from the condensation of the corresponding acid with Building block D, (R)-5-(5-amino-2-fluoro-phenyl)-5-methyl-morpholin-3-one hydrochloride, followed by the treatment with triethyloxonium tetrafluoroborate or trimethyloxonium tetrafluoroborate and ammonium chloride:

With 5-chloro-pyridine 2-carboxylic acid the (R)-5-chloro-pyridine-2-carboxylic acid [3-(5-amino-3-methyl-3,6-dihydro-2H-[1,4]oxazin-3-yl)-4-fluoro-phenyl]-amide (=5-chloro-pyridine-2-carboxylic acid [3-((R)-5-amino-3-methyl-3,6-dihydro-2H-[1,4]oxazin-3-yl)-4-fluoro-phenyl]-amide) (21) as a white foam solid; (calculated) $C_{17}H_{16}ClFN_4O_2$ [362.794]; (found) $[M+H]^+=363$;

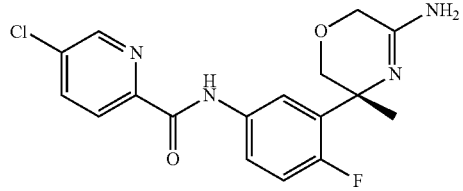

Example 22

Method B (RS)-5-Chloro-pyridine-2-carboxylic acid [3-(5-amino-3-cyclopropyl-3,6-dihydro-2H-[1,4]oxazin-3-yl)-4-fluoro-phenyl]-amide (=5-Chloro-pyridine-2-carboxylic acid [3-((RS)-5-amino-3-cyclopropyl-3,6-dihydro-2H-[1,4]oxazin-3-yl)-4-fluoro-phenyl]-amide) (22)

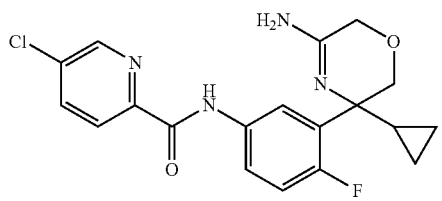

a) (RS)-5-Chloro-pyridine-2-carboxylic acid [3-(3-cyclopropyl-5-thioxo-morpholin-3-yl)-4-fluoro-phenyl]-amide (=5-Chloro-pyridine-2-carboxylic acid [3-((RS)-3-cyclopropyl-5-thioxo-morpholin-3-yl)-4-fluoro-phenyl]-amide)

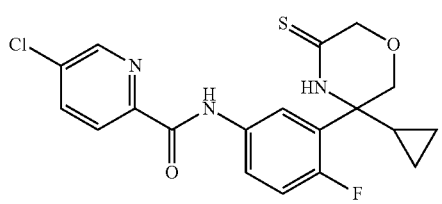

A solution of 5-chloro-pyridine-2-carboxylic acid (0.136 g, 0.86 mmol) in dichloromethane (15 ml), was treated with Huenig's base (0.30 ml, 1.73 mmol) and O-(7-azabenzotriazol-1-yl)-N,N,N',N'-tetramethyluronium hexafluorophosphate (HATU) (0.328 g, 0.86 mmol) at room temperature. After 15 minutes of stirring, (RS)-5-(5-amino-2-fluoro-phenyl)-5-cyclopropyl-morpholine-3-thione (0.177 g, 0.66 mmol) was added and stirring continued for one hour. For the workup, the light yellow solution was poured on an ice-cold saturated solution of sodium hydrogen-carbonate, then extracted twice with dichloromethane. The combined organic layers were washed with brine, dried over sodium sulfate, filtered and evaporated. The residue was purified by chromatography on silica gel using a 9:1-mixture of dichloromethane and ethyl acetate as the eluent. The 5-Chloro-pyridine-2-carboxylic acid [3-((RS)-3-cyclopropyl-5-thioxo-morpholin-3-yl)-4-fluoro-phenyl]-amide was obtained as an off-white solid (0.245 g, 90% of theory). Mass (calculated) $C_{19}H_{17}ClFN_3O_2S$ [405.879]; (found) $[M+H]^+$=406.

b) (RS)-5-Chloro-pyridine-2-carboxylic acid [3-5-amino-3-cyclopropyl-3,6-dihydro-2H-[1,4]oxazin-3-yl)-4-fluoro-phenyl]-amide (=5-Chloro-pyridine-2-carboxylic acid [3-((RS)-5-amino-3-cyclopropyl-3,6-dihydro-2H-[1,4]oxazin-3-yl)-4-fluoro-phenyl]-amide) (22)

A solution of ammonia in methanol (7 M) (5.1 ml, 35 mmol) was added to a suspension of (RS)-5-chloro-pyridine-2-carboxylic acid [3-(3-cyclopropyl-5-thioxo-morpholin-3-yl)-4-fluoro-phenyl]-amide (=5-chloro-pyridine-2-carboxylic acid [3-((RS)-3-cyclopropyl-5-thioxo-morpholin-3-yl)-4-fluoro-phenyl]-amide) (0.240 g, 0.59 mmol) in methanol (18 ml). Thereafter, tent-butyl hydroperoxide (70% in water) (0.81 ml, 5.9 mmol) was added at room temperature and the mixture stirred for 16 hours. For the workup, the clear solution was evaporated at reduced pressure. The residue was purified by chromatography on silica gel using a 80:10:1-mixture of ethyl acetate, methanol, and ammoniumhydroxide as the eluent. The pure fractions were combined and evaporated, then the residue was treated with a mixture of dichloromethane and water. After evaporation of the organic layer, the 5-chloro-pyridine-2-carboxylic acid [3-((RS)-5-amino-3-cyclopropyl-3,6-dihydro-2H-[1,4]oxazin-3-yl)-4-fluoro-phenyl]-amide (22) was obtained as a white solid (99 mg, 43% of theory). Mass (calculated) $C_{19}H_{18}ClFN_4O_2S$ [388.828]; (found) $[M+H]^+$=389.

Example 23

(RS)-5-(2,2,2-Trifluoro-ethoxy)-pyridine-2-carboxylic acid [3-(5-amino-3-cyclopropyl-3,6-dihydro-2H-[1,4]oxazin-3-yl)-4-fluoro-phenyl]-amide (=5-(2,2,2-Trifluoro-ethoxy)-pyridine-2-carboxylic acid [3-((RS)-5-amino-3-cyclopropyl-3,6-dihydro-2H-[1,4]oxazin-3-yl)-4-fluoro-phenyl]-amide) (23)

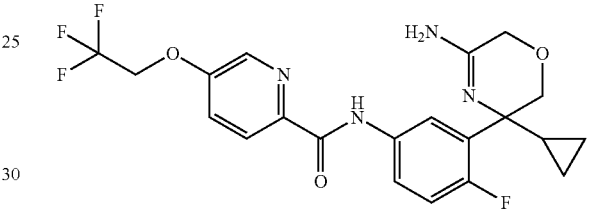

In an analogous manner to that described in example 6 (Method B), the condensation of 5-(2,2,2-trifluoro-ethoxy)-pyridine-2-carboxylic acid (CAS 881409-53-6) and (RS)-5-(5-amino-2-fluoro-phenyl)-5-cyclopropyl-morpholine-3-thione followed by the treatment with tert-butyl hydroperoxide and ammonia yielded the title compound (23) as a white solid. Mass (calculated) $C_{21}H_{20}F_4N_4O_3$ [452.406]; (found) $[M+H]^+$=453.

Example 24

(RS)-5-(2,2,2-Trifluoro-ethoxy)-pyridine-2-carboxylic acid [3-((RS)-5-amino-3-methyl-3,6-dihydro-2H-[1,4]oxazin-3-yl)-phenyl]-amide hydrochloride (=5-(2,2,2-Trifluoro-ethoxy)-pyridine-2-carboxylic acid [3-(5-amino-3-methyl-3,6-dihydro-2H-[1,4]oxazin-3-yl)-phenyl]-amide hydrochloride)

a) (RS)-5-(2,2,2-Trifluoro-ethoxy)-pyridine-2-carboxylic acid [3-(3-methyl-5-thioxo-morpholin-3-yl)-phenyl]-amide (=5-(2,2,2-Trifluoro-ethoxy)-pyridine-2-carboxylic acid [3-((RS)-3-methyl-5-thioxo-morpholin-3-yl)-phenyl]-amide)

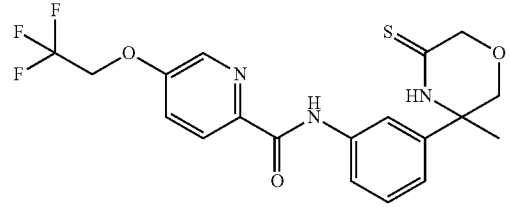

In a reaction analogous to that described in example 6 (method B), the condensation of 5-(2,2,2-trifluoro-ethoxy)- pyridine-2-carboxylic acid (CAS 881409-53-6) with Building block F, (RS)-5-(3-amino-phenyl)-5-methyl-morpholine-3-thione, yielded the title compound as a as light yellow oil (64% of theory). Mass (calculated) $C_{19}H_{18}F_3N_3O_3S$ [425.43]; (found) $[M+H]^+=426$.

b) (RS)-5-(2,2,2-Trifluoro-ethoxy)-pyridine-2-carboxylic acid [3-(5-amino-3-methyl-3,6-dihydro-2H-[1,4]oxazin-3-yl)-phenyl]-amide hydrochloride (=5-(2,2,2-Trifluoro-ethoxy)-pyridine-2-carboxylic acid [3-((RS)-5-amino-3-methyl-3,6-dihydro-2H-[1,4]oxazin-3-yl)-phenyl]-amide hydrochloride)

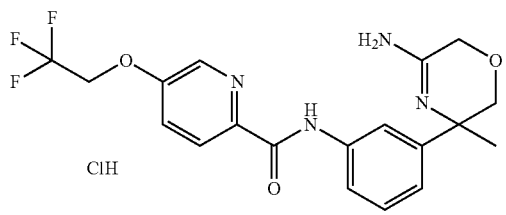

In a pressure tube, 7 M ammonia in methanol (3.0 ml) was added to (RS)-5-(2,2,2-trifluoro-ethoxy)-pyridine-2-carboxylic acid [3-(3-methyl-5-thioxo-morpholin-3-yl)-phenyl]-amide (0.22 g, 0.69 mmol) and the reaction mixture was heated at 100° C. for 3 hours. UPLC analysis showed a 1:1 conversion to the desired product. The solvent was removed at reduced pressure and the crude mixture was taken up with 7 M ammonia in methanol (3.0 mL) The reaction mixture was heated at 100° C. in a pressure tube for 4 hours more. UPLC analysis showed an increase in conversion to the desired product while the formation of (RS)-5-(2,2,2-trifluoro-ethoxy)-pyridine-2-carboxylic acid [3-(3-methyl-5-oxo-morpholin-3-yl)-phenyl]-amide was also observed. The reaction was stopped and the solvent removed at reduced pressure. The crude product was passed on a 2 g SCX column to yield 0.09 g of the title compound (24) that was further purified by preparative HPLC (20 min elution) to give 0.042 g (14% of theory) of the 5-(2,2,2-trifluoro-ethoxy)-pyridine-2-carboxylic acid [3-((RS)-5-amino-3-methyl-3,6-dihydro-2H-[1,4]oxazin-3-yl)-phenyl]-amide hydrochloride as a white foam. Mass (calculated) $C_{19}H_{19}F_3N_4O_3$ [408.38]; (found) $[M+H]^+=409$;

Example 25

(RS)-Pyrazine-2-carboxylic acid [3-(5-amino-3-methyl-3,6-dihydro-2H-[1,4]oxazin-3-yl)phenyl]-amide hydrochloride (=Pyrazine-2-carboxylic acid [3-((RS)-5-amino-3-methyl-3,6-dihydro-2H-[1,4]oxazin-3-yl)phenyl]-amide hydrochloride)

The reaction analogous to that described in example 6 (method B), starting from the condensation of pyrazine-2-carboxylic acid with Building block F, (RS)-5-(3-amino-phenyl)-5-methyl-morpholine-3-thione, followed by the treatment with ammonia in methanol as described in example 24, yielded the title compound (25) as a white solid. Mass (calculated) $C_{16}H_{17}N_5O_2$ [311.35]; (found) $[M+H]^+=312$;

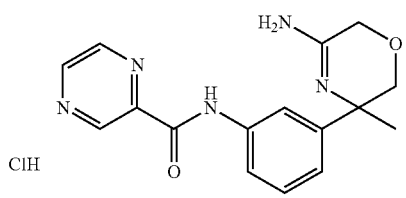

Example 26

(RS)-N-[3-(5-Amino-3-methyl-3,6-dihydro-2H-[1,4]oxazin-3-yl)-4-fluoro-phenyl]-2,2,3,3,3-pentafluoro-propionamide (26)

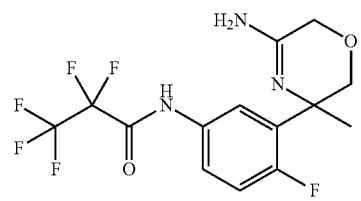

a) (RS)-2,2,3,3,3-Pentafluoro-N-[4-fluoro-3-(3-methyl-5-oxo-morpholin-3-yl)-phenyl]-propionamide

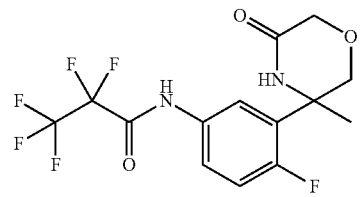

A dispersion of (RS)-5-(5-amino-2-fluoro-phenyl)-5-methyl-morpholin-3-one hydrochloride (Building block C) (0.20 g, 0.8 mmol) in dichloromethane (4.5 ml) was treated with triethylamine (0.37 ml, 2.7 mmol), then the reaction mixture was cooled to 0° C., and, thereafter, a solution of 2,2,3,3,3-pentofluoropropionic acid anhydride (0.267 g, 0.9 mmol) in dichloromethane (0.5 ml) was added. The reaction mixture was stirred at room temperature for 2 days. For the workup, the solvent was evaporated and the crude product directly chromatographed on an Isolute flash $NH_2$ column using a gradient of dichloromethane/methanol=100/0 to 95/5 as the eluent. There were obtained 0.21 g (74% of theory) of the title compound as a white solid. Mass (calculated) $C_{14}H_{12}F_6N_2O_3$ [370.254]; (found) $[M+H]^+=371$.

b) (RS)-N-[3-(5-Amino-3-methyl-3,6-dihydro-2H-[1,4]oxazin-3-yl)-4-fluoro-phenyl]-2,2,3,3,3-pentafluoro-propionamide In a reaction sequence analogous to that described in Example 1 (method A), the treatment of (RS)-2,2,3,3,3-pentafluoro-N-[4-fluoro-3-(3-methyl-5-oxo-morpholin-3-yl)-phenyl]-propionamide with trimethyloxonium tetrafluoroborate and ammonium chloride yielded the (RS)-N-[3-(5-amino-3-methyl-3,6-dihydro-2H-[1,4]oxazin-3-yl)-4-fluoro-phenyl]-2,2,3,3,3-pentafluoro-propionamide (26) as a

Example 27

(RS)-N-[3-(5-Amino-3-methyl-3,6-dihydro-2H-[1,4]oxazin-3-yl)-4-fluoro-phenyl]-4-chloro-thiobenzamide (27)

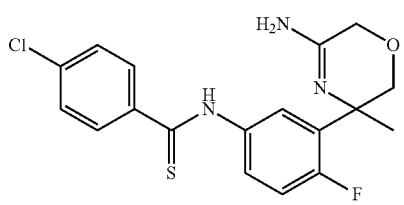

A solution of (RS)-N-[3-(5-amino-3-methyl-3,6-dihydro-2H-[1,4]oxazin-3-yl)-4-fluoro-phenyl]-4-chloro-benzamide (0.056 g, 0.2 mmol) in 1,2-dimethoxyethane (2 ml) was treated with Lawesson's reagent (0.083 g, 0.2 mmol). After heating to 70° C. the dispersion turned into solution; the temperature was kept during 16 hours. Another 0.5 eq of Lawesson's reagent were added to complete the reaction and heating was continued at 80° C. After 2 days the reaction was still incomplete. For the workup, the reaction mixture was evaporated to dryness and the residue directly purified by chromatography on an Isolute flash NH$_2$ column using a gradient of dichloromethane/methanol=100/0 to 90/10 as the eluent. There were obtained 0.006 g (10% of theory) of (RS)-N-[3-(5-amino-3-methyl-3,6-dihydro-2H-[1,4]oxazin-3-yl)-4-fluoro-phenyl]-4-chloro-thiobenzamide (27) as a yellow solid. Mass (calculated) C$_{18}$H$_{17}$ClFN$_3$OS [377.87]; (found) [M+H]$^+$=378.

Example 28

5-Chloro-pyridine-2-carboxylic acid [3-((3R,6R)- and (3S,6)-5-amino-6-benzyl-3-methyl-3,6-dihydro-2H-[1,4]oxazin-3-yl)-4-fluoro-phenyl]-amide

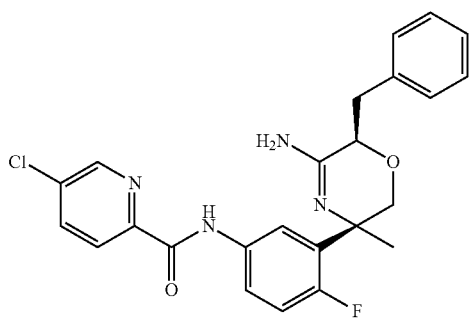

In a reaction sequence analogous to that described in Example 1 (method A), the title compound was obtained starting from the condensation of 5-chloro-pyridine-2-carboxylic acid with Building block M, (2R,5R)- and (2S,5S)-5-(5-amino-2-fluoro-phenyl)-2-benzyl-5-methyl-morpholin-3-one, followed by the treatment with trimethyloxonium tetrafluoroborate and ammonium chloride as a light yellow foam. Mass (calculated) C$_{24}$H$_{22}$ClFN$_4$O$_2$ [452.915]; (found) [M+H]$^+$=453.

Example 29

5-Chloro-pyridine-2-carboxylic acid [3-((3R,6S)- and (3S,6R)-5-amino-6-benzyl-3-methyl-3,6-dihydro-2H-[1,4]oxazin-3-yl)-4-fluoro-phenyl]-amide

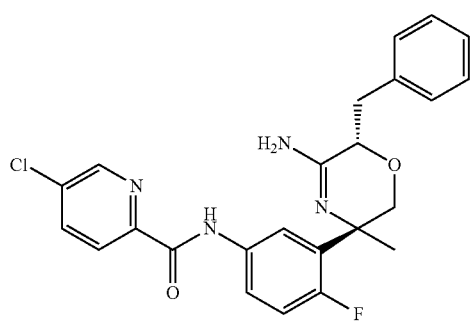

In a reaction sequence analogous to that described in Example 1 (method A), the title compound was obtained starting from the condensation of 5-chloro-pyridine-2-carboxylic acid with Building block N, (2S,5R)- and (2R,5S)-5-(5-amino-2-fluoro-phenyl)-2-benzyl-5-methyl-morpholin-3-one, followed by the treatment with trimethyloxonium tetrafluoroborate and ammonium chloride as a light yellow foam. Mass (calculated) C$_{24}$H$_{22}$ClFN$_4$O$_2$ [452.915]; (found) [M+H]$^+$=453.

Examples 30 and 31

5-Chloro-pyridine-2-carboxylic acid [3-((3R,6R)-5-amino-3-methyl-6-phenyl-3,6-dihydro-2H-[1,4]oxazin-3-yl)-4-fluoro-phenyl]-amide and 5-Chloro-pyridine-2-carboxylic acid [3-((3R,6S)-5-amino-3-methyl-6-phenyl-3,6-dihydro-2H-[1,4]oxazin-3-yl)-4-fluoro-phenyl]-amide

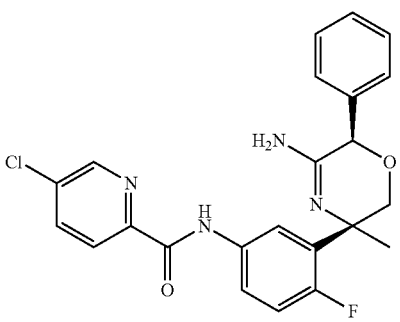

30

-continued

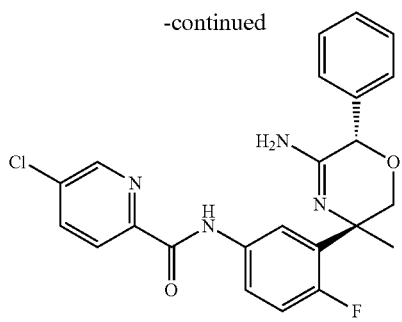

In a reaction sequence analogous to that described in Example 1 (method A), the title compounds were obtained starting from the condensation of 5-chloro-pyridine-2-carboxylic acid with Building block S, (2S,5R)-5-(5-amino-2-fluoro-phenyl)-5-methyl-2-phenyl-morpholin-3-one hydrochloride, to yield the 5-chloro-pyridine-2-carboxylic acid [4-fluoro-3-((3R,6S)-5-methoxy-3-methyl-6-phenyl-3,6-dihydro-2H-[1,4]oxazin-3-yl)-phenyl]-amide. Treatment with trimethyloxonium tetrafluoroborate and ammonium chloride resulted in an epimerized mixture of 5-chloro-pyridine-2-carboxylic acid [3-((3R,6R)-5-amino-3-methyl-6-phenyl-3,6-dihydro-2H-[1,4]oxazin-3-yl)-4-fluoro-phenyl]-amide and 5-chloro-pyridine-2-carboxylic acid [3-((3R,6S)-5-amino-3-methyl-6-phenyl-3,6-dihydro-2H-[1,4]oxazin-3-yl)-4-fluoro-phenyl]-amide which was separated by chromatography on a Si-amine column using a gradient of dichloromethane and methanol=100/0 to 97/3 as the eluent. Both epimers were obtained as off-white powders. Mass (calculated) $C_{23}H_{20}ClFN_4O_2$ [438.89]; (found) $[M+H]^+$=439.

Examples 32-52

In a reaction sequence analogous to that described in example 22 (method B), the condensation of carboxylic acids with Building blocks F, H, K, L and O followed by the treatment of the resulting thiones with a mixture of ammonia in water and tent-butyl hydroperoxide yielded the following compounds:

Example 32

With 5-butyl-pyridine-2-carboxylic acid and Building block F, (RS)-5-(3-amino-phenyl)-5-methyl-morpholine-3-thione, the 5-butyl-pyridine-2-carboxylic acid [3-((RS)-5-amino-3-methyl-3,6-dihydro-2H-[1,4]oxazin-3-yl)-phenyl]-amide hydrochloride (32) (yield: 8% of theory). Mass (calculated) $C_{21}H_{26}N_4O_2.HCl$ [402.923]; (found) $[M+H]^+$=367.

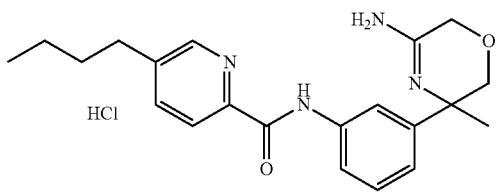

Example 33

With 3-chloro-5-trifluoromethyl-pyridine-2-carboxylic acid and Building block F, (RS)-5-(3-amino-phenyl)-5-methyl-morpholine-3-thione, the 3-Chloro-5-trifluoromethyl-pyridine-2-carboxylic acid [3-((RS)-5-amino-3-methyl-3,6-dihydro-2H-[1,4]oxazin-3-yl)-phenyl]-amide (33) (yield: 50% of theory). Mass (calculated) $C_{18}H_{16}ClF_3N_4O_2.HCl$ [449.258]; (found) $[M+H]^+$=413.

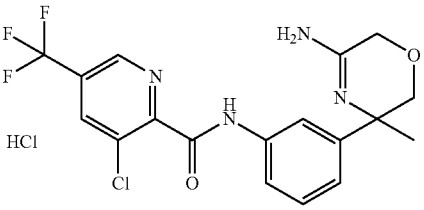

Example 34

With 3,5-dichloro-pyridine-2-carboxylic acid and Building block H, (R)-5-(5-amino-2-fluoro-phenyl)-5-methyl-morpholine-3-thione, the 3,5-dichloro-pyridine-2-carboxylic acid [3-((R)-5-amino-3-methyl-3,6-dihydro-2H-[1,4]oxazin-3-yl)-4-fluoro-phenyl]-amide (34) as a white solid. Mass (calculated) $C_{17}H_{15}Cl_2FN_4O_2$ [397.235]; (found) $[M+H]^+$=397, $[M+2-H]^+$=399.

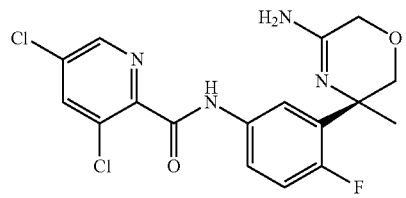

Example 35

With 5-chloro-pyrimidine-2-carboxylic acid and Building block H, (R)-5-(5-amino-2-fluoro-phenyl)-5-methyl-morpholine-3-thione, the 5-chloro-pyrimidine-2-carboxylic acid [3-((R)-5-amino-3-methyl-3,6-dihydro-2H-[1,4]oxazin-3-yl)-4-fluoro-phenyl]-amide (35) as a white solid. Mass (calculated) $C_{16}H_{15}ClFN_5O_2$ [363.778]; (found) $[M+H]^+$=364.

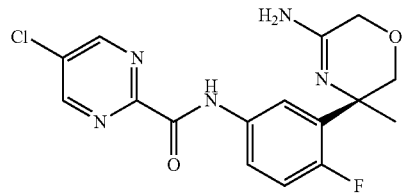

Example 36

With 5-trifluoromethyl-furan-3-carboxylic acid and Building block H, (R)-5-(5-amino-2-fluoro-phenyl)-5-methyl-morpholine-3-thione, the 5-trifluoromethyl-furan-3-carboxylic acid [3-((R)-5-amino-3-methyl-3,6-dihydro-2H-[1,4]oxazin-3-yl)-4-fluoro-phenyl]-amide (36) as a white solid. Mass (calculated) $C_{17}H_{15}F_4N_3O_3$ [385.315]; (found) $[M+H]^+$=386.

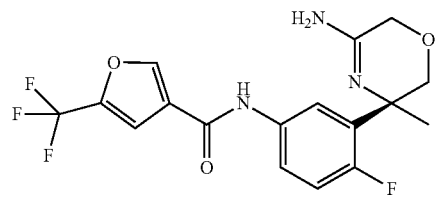

Example 37

With 3-fluoro-pyridine-2-carboxylic acid and Building block H, (R)-5-(5-amino-2-fluoro-phenyl)-5-methyl-morpholine-3-thione, the 3-fluoro-pyridine-2-carboxylic acid [3-((R)-5-amino-3-methyl-3,6-dihydro-2H-[1,4]oxazin-3-yl)-4-fluoro-phenyl]-amide (37) as a white foam. Mass (calculated) $C_{17}H_{16}F_2N_4O_2$ [346.335]; (found) [M+H]$^+$=347.

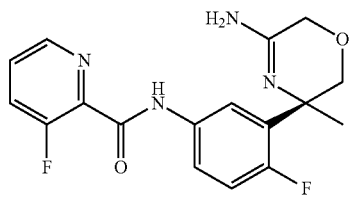

Example 38

With 3-chloro-5-trifluoromethyl-pyridine-2-carboxylic acid and Building block H, (R)-5-(5-amino-2-fluoro-phenyl)-5-methyl-morpholine-3-thione, the 3-chloro-5-trifluoromethyl-pyridine-2-carboxylic acid [3-((R)-5-amino-3-methyl-3,6-dihydro-2H-[1,4]oxazin-3-yl)-4-fluoro-phenyl]-amide (38) as a yellow foam. Mass (calculated) $C_{18}H_{15}ClF_4N_4O_2$ [430.787]; (found) [M+H]$^+$=431.

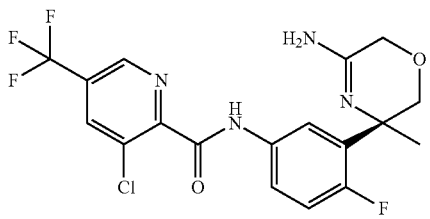

Example 39

With 2-methyl-oxazole-4-carboxylic acid and Building block H, (R)-5-(5-amino-2-fluoro-phenyl)-5-methyl-morpholine-3-thione, the 2-methyl-oxazole-4-carboxylic acid [3-((R)-5-amino-3-methyl-3,6-dihydro-2H-[1,4]oxazin-3-yl)-4-fluoro-phenyl]-amide (39) as an off-white foam. Mass (calculated) $C_{16}H_{17}FN_4O_3$ [323.333]; (found) [M+H]$^+$=333.

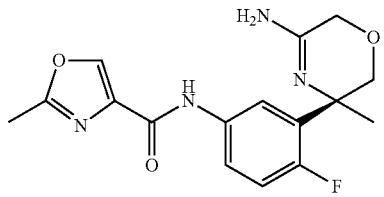

Example 40

With 1-difluoromethyl-1H-pyrazole-3-carboxylic acid and Building block H, (R)-5-(5-amino-2-fluoro-phenyl)-5-methyl-morpholine-3-thione, the 1-difluoromethyl-1H-pyrazole-3-carboxylic acid [3-((R)-5-amino-3-methyl-3,6-dihydro-2H-[1,4]oxazin-3-yl)-4-fluoro-phenyl]-amide (40) as a white foam. Mass (calculated) $C_{16}H_{16}F_3N_5O_2$ [367.329]; (found) [M+H]$^+$=368.

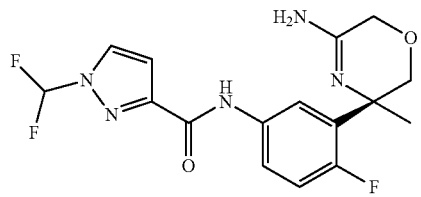

Example 41

With 3,5-difluoro-pyridine-2-carboxylic acid and Building block H, (R)-5-(5-amino-2-fluoro-phenyl)-5-methyl-morpholine-3-thione, the 3,5-difluoro-pyridine-2-carboxylic acid [3-((R)-5-amino-3-methyl-3,6-dihydro-2H-[1,4]oxazin-3-yl)-4-fluoro-phenyl]-amide (41) as an off-white solid. Mass (calculated) $C_{17}H_{15}F_3N_4O_2$ [364.325]; (found) [M+H]$^+$=365.

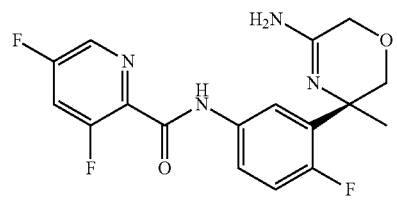

Example 42

With 4-cyano-2-fluoro-benzoic acid and Building block H, (R)-5-(5-amino-2-fluoro-phenyl)-5-methyl-morpholine-3-thione, the N-[3-((R)-5-amino-3-methyl-3,6-dihydro-2H-[1,4]oxazin-3-yl)-4-fluoro-phenyl]-4-cyano-2-fluoro-benzamide (42) as a white solid. Mass (calculated) $C_{19}H_{16}F_2N_4O_2$ [370.357]; (found) [M+H]$^+$=371.

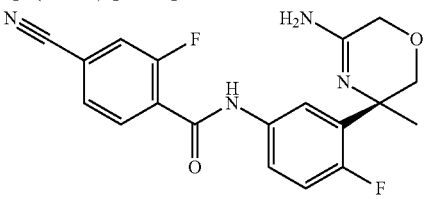

Example 43

With 4-chloro-1-methyl-1H-pyrazole-3-carboxylic acid and Building block H, (R)-5-(5-amino-2-fluoro-phenyl)-5-methyl-morpholine-3-thione, the 4-chloro-1-methyl-1H-pyrazole-3-carboxylic acid [3-((R)-5-amino-3-methyl-3,6-dihydro-2H-[1,4]oxazin-3-yl)-4-fluoro-phenyl]-amide (43) as a white solid. Mass (calculated) $C_{16}H_{17}ClFN_5O_2$ [365.794]; (found) [M+H]$^+$=366.

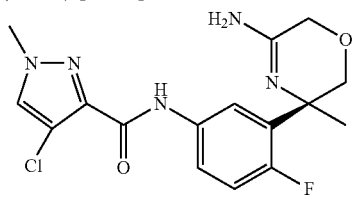

Example 44

With 3-methyl-thiophene-2-carboxylic acid and Building block H, (R)-5-(5-amino-2-fluoro-phenyl)-5-methyl-morpholine-3-thione, the 3-methyl-thiophene-2-carboxylic acid [3-((R)-5-amino-3-methyl-3,6-dihydro-2H-[1,4]oxazin-3-yl)-4-fluoro-phenyl]-amide (44) as a white foam. Mass (calculated) $C_{17}H_{18}FN_3O_2S$ [347.412]; (found) $[M+H]^+=348$.

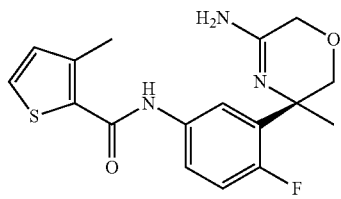

Example 45

With 5-phenyl-oxazole-4-carboxylic acid and Building block H, (R)-5-(5-amino-2-fluoro-phenyl)-5-methyl-morpholine-3-thione, the 5-phenyl-oxazole-4-carboxylic acid [3-((R)-5-amino-3-methyl-3,6-dihydro-2H-[1,4]oxazin-3-yl)-4-fluoro-phenyl]-amide (45) as a white solid. Mass (calculated) $C_{21}H_{19}FN_4O_3$ [394.404]; (found) $[M+H]^+=395$.

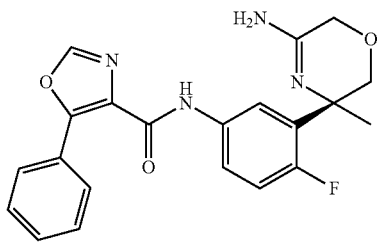

Example 46

With 3-chloro-thiophene-2-carboxylic acid and Building block H, (R)-5-(5-amino-2-fluoro-phenyl)-5-methyl-morpholine-3-thione, the 3-chloro-thiophene-2-carboxylic acid [3-((R)-5-amino-3-methyl-3,6-dihydro-2H-[1,4]oxazin-3-yl)-4-fluoro-phenyl]-amide (46) as a white foam. Mass (calculated) $C_{16}H_{15}ClFN_3O_2S$ [367.830]; (found) $[M+H]^+=368$.

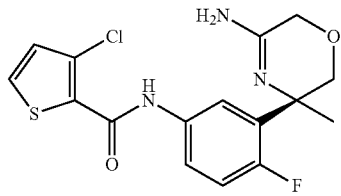

Example 47

With 2-methyl-4-trifluoromethyl-thiazole-5-carboxylic acid and Building block H, (R)-5-(5-amino-2-fluoro-phenyl)-5-methyl-morpholine-3-thione, the 2-methyl-4-trifluoromethyl-thiazole-5-carboxylic acid [3-((R)-5-amino-3-methyl-3,6-dihydro-2H-[1,4]oxazin-3-yl)-4-fluoro-phenyl]-amide (47) as a white foam. Mass (calculated) $C_{17}H_{16}F_4N_4O_2S$ [416.397]; (found) $[M+H]^+=417$.

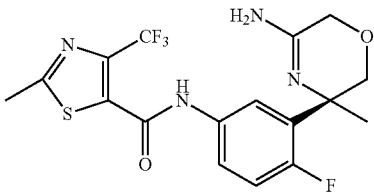

Example 48

With 3-(2,2,2-trifluoro-ethoxy)-pyridine-2-carboxylic acid and Building block H, (R)-5-(5-amino-2-fluoro-phenyl)-5-methyl-morpholine-3-thione, the 3-(2,2,2-trifluoro-ethoxy)-pyridine-2-carboxylic acid [3-((R)-5-amino-3-methyl-3,6-dihydro-2H-[1,4]oxazin-3-yl)-4-fluoro-phenyl]-amide (48) as a colorless solid. Mass (calculated) $C_{19}H_{18}F_4N_4O_3$ [426.360]; (found) $[M+H]^+=427$.

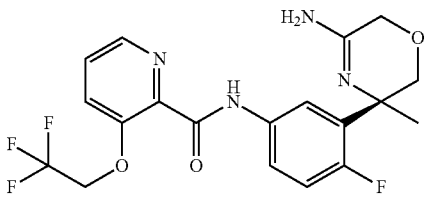

The 3-(2,2,2-trifluoro-ethoxy)-pyridine-2-carboxylic acid was prepared as follows:

a) To a solution of 3-hydroxy-pyridine-2-carboxylic acid methyl ester (200 mg, 1.3 mmol) in N,N-dimethylformamide (2.0 ml) was added at 22° C. sodium hydride (55% in oil, 64 mg) and stirring was continued until gas evolution ceased. The suspension was cooled to 0° C. and treated with trifluoroethyl trifluoromethanesulfonate (728 mg) and stirring was continued at 22° C. for 2 hours. The mixture was partitioned between saturated sodium hydrogen-carbonate solution and ethyl acetate, and the organic layer was dried and evaporated. The residue was purified by chromatography on silica using n-heptane and ethyl acetate (3:1) as the eluent to give 3-(2,2,2-trifluoro-ethoxy)-pyridine-2-carboxylic acid methyl ester as a pale green oil. Mass (calculated) $C_9H_8F_3NO_3$ [235.16]; (found) $[M+H]^+=236$.

b) A solution of 3-(2,2,2-trifluoro-ethoxy)-pyridine-2-carboxylic acid methyl ester (216 mg, 0.9 mmol) in methanol (1 ml) was treated with a solution of lithium hydroxide (78 mg, 3.3 mmol) in water (0.1 ml) and stirring was continued at 22° C. for 2 hours. The solution was evaporated and the residue triturated with 1N aqueous hydrochloric acid. The suspension was filtered, the residue washed with water and dried to give 3-(2,2,2-trifluoro-ethoxy)-pyridine-2-carboxylic acid as a colorless solid. Mass (calculated) $C_8H_6F_3NO_3$ [221.14]; (found) $[M-H]^-=220$.

Example 49

With 5-chloro-pyridine-2-carboxylic acid and Building block K, (R)-5-(5-amino-2-fluoro-phenyl)-5,6,6-trimethyl-morpholine-3-thione, the 5-chloro-pyridine-2-carboxylic acid [3-((R)-5-amino-2,2,3-trimethyl-3,6-dihydro-2H-[1,4]

oxazin-3-yl)-4-fluoro-phenyl]-amide (49) as a light yellow foam. Mass (calculated) C$_{19}$H$_{20}$ClFN$_4$O$_2$ [390.844]; (found) [M+H]$^+$=391.

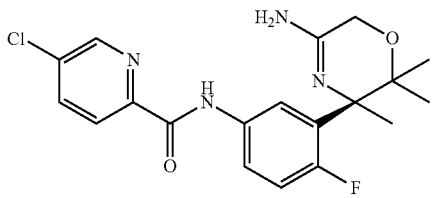

Example 50

With 5-(2,2,2-trifluoro-ethoxy)-pyridine-2-carboxylic acid and Building block K, (R)-5-(5-amino-2-fluoro-phenyl)-5,6,6-trimethyl-morpholine-3-thione, the 5-(2,2,2-trifluoro-ethoxy)-pyridine-2-carboxylic acid [3-((R)-5-amino-2,2,3-trimethyl-3,6-dihydro-2H-[1,4]oxazin-3-yl)-4-fluoro-phenyl]-amide (50) as a white solid. Mass (calculated) C$_{21}$H$_{22}$F$_4$N$_4$O$_3$ [454.422]; (found) [M+H]$^+$=455.

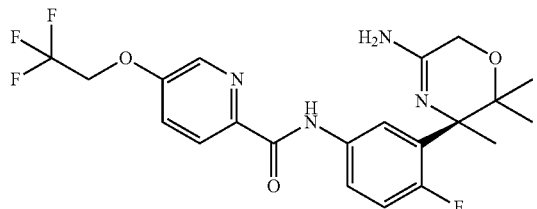

Example 51

With 5-chloro-pyridine-2-carboxylic acid and Building block L, (R)-5-(3-amino-phenyl)-2,2,5-trimethyl-morpholine-3-thione the 5-chloro-pyridine-2-carboxylic acid [3-((R)-5-amino-3,6,6-trimethyl-3,6-dihydro-2H-[1,4]oxazin-3-yl)-phenyl]-amide (51) as a white solid. Mass (calculated) C$_{19}$H$_{21}$ClN$_4$O$_2$ [372.852]; (found) [M+H]$^+$=373.

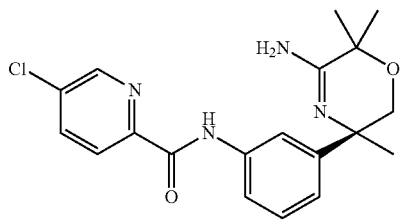

Example 52

With 4-(1,3-oxazol-5-yl)benzoic acid and Building block O, (RS)-5-(5-amino-2-fluoro-phenyl)-5-methyl-morpholine-3-thione hydrochloride the (RS)-N-[3-(5-amino-3-methyl-3,6-dihydro-2H-[1,4]oxazin-3-yl)-4-fluoro-phenyl]-4-oxazol-5-yl-benzamide (52) as a white solid. Mass (calculated) C$_{21}$H$_{19}$FN$_4$O$_2$ [394.404]; (found) [M+H]$^+$=395.

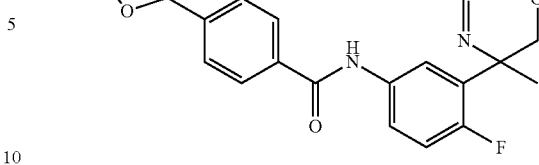

Examples 53-59

In a reaction sequence analogous to that described in example 22 (method B), the condensation of carboxylic acids with Building blocks H, K, and O followed by the treatment of the resulting thiones with a mixture of ammonia in water and tert-butyl hydroperoxide yielded the following compounds:

Example 53

With (RS)-2,2-difluoro-cyclopropanecarboxylic acid and Building block H, (R)-5-(5-amino-2-fluoro-phenyl)-5-methyl-morpholine-3-thione, the (RS)-2,2-difluoro-cyclopropanecarboxylic acid [3-((R)-5-amino-3-methyl-3,6-dihydro-2H-[1,4]oxazin-3-yl)-4-fluoro-phenyl]-amide (53) as a white solid. Mass (calculated) C$_{15}$H$_{16}$F$_3$N$_3$O$_2$ [327.304]; (found) [M+H]$^+$=328.

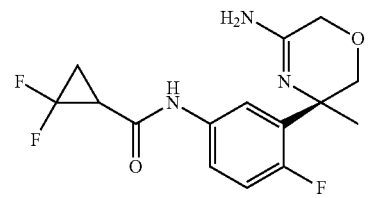

Example 54

With cyclopropanecarboxylic acid and Building block K, (R)-5-(5-amino-2-fluoro-phenyl)-5,6,6-trimethyl-morpholine-3-thione, the cyclopropanecarboxylic acid [3-((R)-5-amino-2,2,3-trimethyl-3,6-dihydro-2H-[1,4]oxazin-3-yl)-4-fluoro-phenyl]-amide (54) as a white foam. Mass (calculated) C$_{17}$H$_{22}$FN$_3$O$_2$ [319.378]; (found) [M+H]$^+$=320.

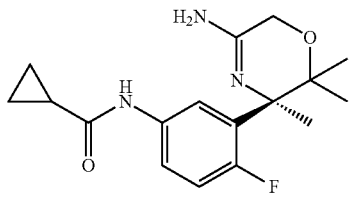

Example 55

With 1-(trifluoromethyl)cyclopropane-1-carboxylic acid and Building block K, (R)-5-(5-amino-2-fluoro-phenyl)-5,6,6-trimethyl-morpholine-3-thione, the 1-trifluoromethyl-cyclopropanecarboxylic acid [3-((R)-5-amino-2,2,3-trimethyl-3,6-dihydro-2H-[1,4]oxazin-3-yl)-4-fluoro-phenyl]-amide

(55) as a white foam. Mass (calculated) $C_{18}H_{21}F_4N_3O_2$ [387.375]; (found) $[M+H]^+=388$.

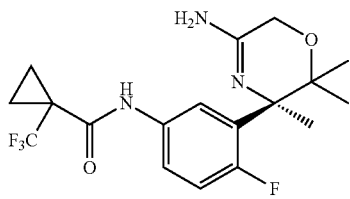

Example 56

With (RS)-2,2-difluoro-cyclopropanecarboxylic acid and Building block K, (R)-5-(5-amino-2-fluoro-phenyl)-5,6,6-trimethyl-morpholine-3-thione, the (RS)-2,2-difluoro-cyclopropanecarboxylic [3-((R)-5-amino-2,2,3-trimethyl-3,6-dihydro-2H-[1,4]oxazin-3-yl)-4-fluoro-phenyl]-amide (56) as a white foam. Mass (calculated) $C_{17}H_{20}F_3N_3O_2$ [355.358]; (found) $[M+H]^+=356$.

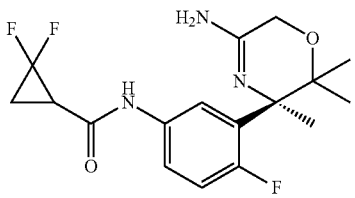

Example 57

With 1-trifluoromethyl-cyclopropanecarboxylic acid and Building block 0, (RS)-5-(5-amino-2-fluoro-phenyl)-5-methyl-morpholine-3-thione hydrochloride the 1-trifluoromethyl-cyclopropanecarboxylic acid [3-((RS)-5-amino-3-methyl-3,6-dihydro-2H-[1,4]oxazin-3-yl)-phenyl]-amide (57) as a white solid. Mass (calculated) $C_{16}H_{17}F_4N_3O_2$ [359.321]; (found) $[M+H]^+=360$.

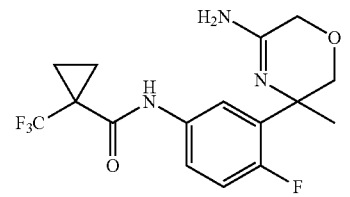

Example 58

With 3-chloro-cyclobutanecarboxylic acid and Building block H, (R)-5-(5-amino-2-fluoro-phenyl)-5-methyl-morpholine-3-thione, the 3-chloro-cyclobutanecarboxylic acid [3-((R)-5-amino-3-methyl-3,6-dihydro-2H-[1,4]oxazin-3-yl)-4-fluoro-phenyl]-amide (58) as a white solid. Mass (calculated) $C_{16}H_{19}ClFN_3O_2$ [339.796]; (found) $[M+H]^+=340$.

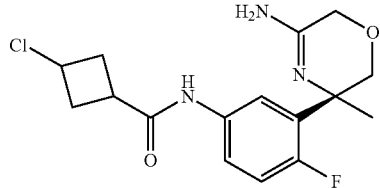

Example 59

With 3,3-difluoro-cyclobutanecarboxylic acid and Building block H, (R)-5-(5-amino-2-fluoro-phenyl)-5-methyl-morpholine-3-thione, the 3,3-difluoro-cyclobutanecarboxylic acid [3-((R)-5-amino-3-methyl-3,6-dihydro-2H-[1,4]oxazin-3-yl)-4-fluoro-phenyl]-amide (59) as a white solid. Mass (calculated) $C_{16}H_{18}F_3N_3O_2$ [341.331]; (found) $[M+H]^+=342$.

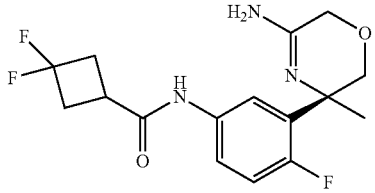

Examples 60-66

In a reaction sequence analogous to that described in example 6 (method B), starting from the condensation of a carboxylic acid with Building block F, (RS)-5-(3-amino-phenyl)-5-methyl-morpholine-3-thione, followed by the treatment with ammonia in methanol as described in example 24b), the following compounds were obtained:

Example 60

With 5-cyclopropylmethoxy-pyridine-2-carboxylic acid the 5-cyclopropylmethoxy-pyridine-2-carboxylic acid [3-((RS)-5-amino-3-methyl-3,6-dihydro-2H-[1,4]oxazin-3-yl)-phenyl]-amide hydrochloride (60) (yield: 10% of theory). Mass (calculated) $C_{21}H_{24}N_4O_3 \cdot ClH$ [416.906]; (found) $[M+H]^+=381$.

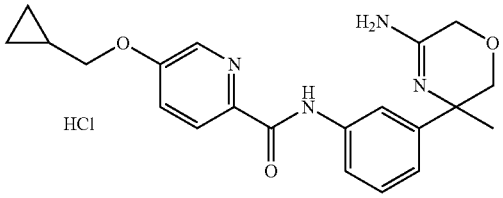

The 5-cyclopropylmethoxy-pyridine-2-carboxylic acid was prepared as follows:

a) 5-Cyclopropylmethoxy-pyridine-2-carboxylic acid methyl ester

A solution of 5-hydroxy-pyridine-2-carboxylic acid methyl ester (2.0 g, 13.1 mmol) in N,N-dimethylformamide was treated with potassium carbonate (2.71 g, 19.6 mmol) and 1-bromomethyl-cyclopropane (1.6 ml, 15.7 mmol). The reaction mixture was stirred at 100° C. for 16 hours. For the workup, the reaction mixture was diluted with ethyl acetate, solid material was filtered, and the filtrate evaporated at reduced pressure. The residue was purified by chromatography on silica using a gradient of n-heptane and ethyl acetate=100/0 to 20/80 as the eluent to give the 5-cyclopropylmethoxy-pyridine-2-carboxylic acid methyl ester as a yellow liquid (1.69 g, 62% of theory). Mass (calculated) $C_{11}H_{13}NO_3$ [207.228]; (found) $[M+H]^+=208$.

b) 5-Cyclopropylmethoxy-pyridine-2-carboxylic acid

In a manner analogous to that described in example 48b) the hydrolysis of 5-cyclopropylmethoxy-pyridine-2-carboxylic acid methyl ester with lithium hydroxide yielded the title compound as a white solid. Mass (calculated) $C_{10}H_{11}NO_3$ [193.201]; (found) [M+H]$^+$=194.

Example 61

With 5-(2-fluoro-ethoxy)-pyridine-2-carboxylic acid the 5-(2-fluoro-ethoxy)-pyridine-2-carboxylic acid [3-((RS)-5-amino-3-methyl-3,6-dihydro-2H-[1,4]oxazin-3-yl)-phenyl]-amide hydrochloride (61) (yield: 10% of theory). Mass (calculated) $C_{19}H_{21}FN_4O_3$·ClH [408.859]; (found) [M+H]$^+$=373.

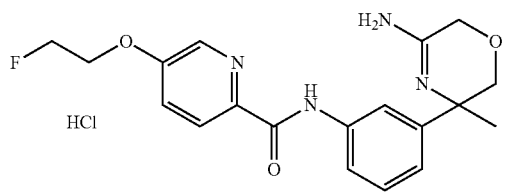

The 5-(2-fluoro-ethoxy)-pyridine-2-carboxylic acid was prepared in a reaction sequence analogous to that in example 60 for the preparation of the 5-cyclopropylmethoxy-pyridine-2-carboxylic acid: Alkylation of the 5-hydroxy-pyridine-2-carboxylic acid methyl ester with 1-bromo-2-fluoroethane and hydrolysis of the 5-(2-fluoro-ethoxy)-pyridine-2-carboxylic acid methyl ester yielded the 5-(2-fluoro-ethoxy)-pyridine-2-carboxylic acid as a white solid. Mass (calculated) $C_8H_8FNO_3$ [185.153]; (found) [M+H]$^+$=186.

Example 62

With 5-(2,2-difluoro-ethoxy)-pyridine-2-carboxylic acid the 5-(2,2-difluoro-ethoxy)-pyridine-2-carboxylic acid [3-((RS)-5-amino-3-methyl-3,6-dihydro-2H-[1,4]oxazin-3-yl)-phenyl]-amide hydrochloride (62) (yield: 12% of theory). Mass (calculated) $C_{19}H_{20}F_2N_4O_3$·ClH [426.849]; (found) [M+H]$^+$=391.

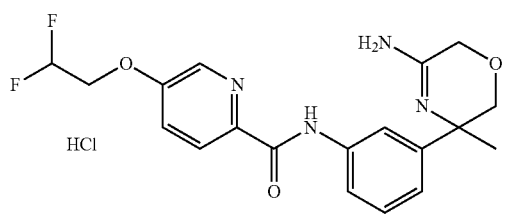

The 5-(2,2-difluoro-ethoxy)-pyridine-2-carboxylic acid was prepared in a reaction sequence analogous to that in example 60 for the preparation of the 5-cyclopropylmethoxy-pyridine-2-carboxylic acid: Alkylation of the 5-hydroxy-pyridine-2-carboxylic acid methyl ester with 2,2-difluoroethyl triflate and hydrolysis of the 5-(2,2-difluoro-ethoxy)-pyridine-2-carboxylic acid methyl ester yielded the 5-(2,2-difluoro-ethoxy)-pyridine-2-carboxylic acid as an off-white solid. Mass (calculated) $C_8H_7F_2NO_3$ [203.143]; (found) [M+H]$^+$=204.

Example 63

With pyrimidine-4-carboxylic acid the pyrimidine-4-carboxylic acid [3-((RS)-5-amino-3-methyl-3,6-dihydro-2H-[1, 4]oxazin-3-yl)-phenyl]-amide (63) (yield: 15% of theory). Mass (calculated) $C_{16}H_{17}N_5O_1$ [311.343]; (found) [M+H]$^+$=312.

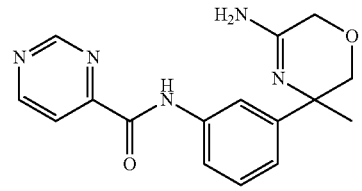

Example 64

With 5-but-3-enyloxy-pyridine-2-carboxylic acid the 5-but-3-enyloxy-pyridine-2-carboxylic acid [3-((RS)-5-amino-3-methyl-3,6-dihydro-2H-[1,4]oxazin-3-yl)-phenyl]-amide (64) (yield: 10% of theory). Mass (calculated) $C_{21}H_{24}N_4O_3$ [380.446]; (found) [M+H]$^+$=381.

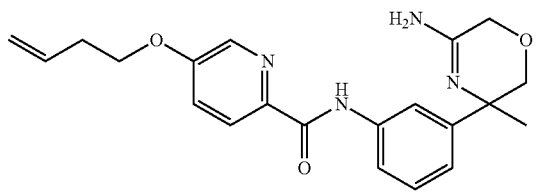

The 5-but-3-enyloxy-pyridine-2-carboxylic acid was prepared in a reaction sequence analogous to that in example 60 for the preparation of the 5-cyclopropylmethoxy-pyridine-2-carboxylic acid: Alkylation of the 5-hydroxy-pyridine-2-carboxylic acid methyl ester with 4-bromo-1-butene and hydrolysis of the 5-but-3-enyloxy-pyridine-2-carboxylic acid methyl ester yielded the 5-but-3-enyloxy-pyridine-2-carboxylic acid as a light yellow solid. Mass (calculated) $C_{10}H_{11}NO_3$ [193.201]; (found) [M+H]$^+$=194.

Example 65

With 5-methyl-pyrazine-2-carboxylic acid the 5-methyl-pyrazine-2-carboxylic acid [3-((RS)-5-amino-3-methyl-3,6-dihydro-2H-[1,4]oxazin-3-yl)-phenyl]-amide (65) (yield: 17.5% of theory). Mass (calculated) $C_{17}H_{19}N_5O_2$ [325.370]; (found) [M+H]$^+$=326.

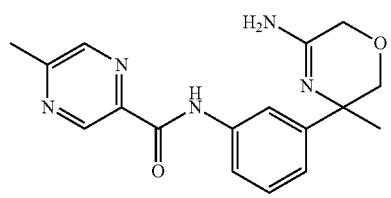

Example 66

With 5-benzyloxy-pyridine-2-carboxylic acid (CAS74386-55-3) the 5-benzyloxy-pyridine-2-carboxylic acid [3-((RS)-5-amino-3-methyl-3,6-dihydro-2H-[1,4]oxazin-3-yl)-phenyl]-amide hydrochloride (66).

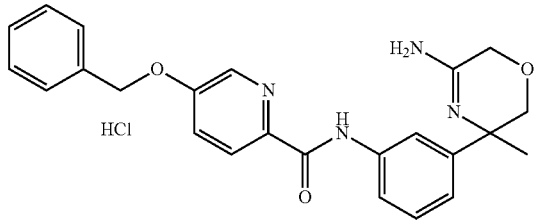

Example 67

Method C

3-Chloro-5-cyano-pyridine-2-carboxylic acid [3-((R)-5-amino-3-methyl-3,6-dihydro-2H-[1,4]oxazin-3-yl)-4-fluoro-phenyl]-amide hydrochloride

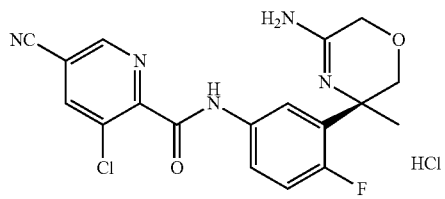

a) 3-Chloro-5-cyano-pyridine-2-carboxylic acid [3-((R)-5-{[bis-(4-methoxy-phenyl)-phenyl-methyl]-amino}-3-methyl-3,6-dihydro-2H-[1,4]oxazin-3-yl)-4-fluoro-phenyl]-amide In a manner analogous to that described in example E1 (method E), the reaction of 3-chloro-5-cyano-pyridine-2-carboxylic acid with Building block J, [(R)-5-(5-amino-2-fluoro-phenyl)-5-methyl-5,6-dihydro-2H-[1,4]oxazin-3-yl]-[bis-(4-methoxy-phenyl)-phenyl-methyl]-amine, using the 4-(4,6-dimethoxy-1,3,5-triazin-2-yl)-4-methylmorpholinium chloride hydrate (DMTMM) as the condensating agent, yielded the title compound as a yellow solid (44% of theory). Mass (calculated) $C_{39}H_{33}ClFN_5O_4$ [690.160]; (found) $[M]^+=690$.

b) 3-Chloro-5-cyano-pyridine-2-carboxylic acid [3-((R)-5-amino-3-methyl-3,6-dihydro-2H-[1,4]oxazin-3-yl)-4-fluoro-phenyl]amide hydrochloride A solution of 3-chloro-5-cyano-pyridine-2-carboxylic acid [3-((R)-5-{[bis-(4-methoxy-phenyl)-phenyl-methyl]-amino}-3-methyl-3,6-dihydro-2H-[1,4]oxazin-3-yl)-4-fluoro-phenyl]-amide (80 mg, 0.12 mmol) in dichloromethane (2 ml) was treated at room temperature with trifluoroacetic acid (0.89 ml, 1.16 mmol); the yellow solution immediately turned to orange. The reaction mixture was stirred at room temperature for 16 hours. For the workup, it was poured into a sodium carbonate solution (1 M, 2 ml), then extracted with dichloromethane (10 ml). The organic layer was washed with brine (5 ml), dried over sodium sulfate, and evaporated. After chromatography on silica gel using a gradient of dichloromethane and methanol=100/0 to 93/7 the 3-chloro-5-cyano-pyridine-2-carboxylic acid [3-((R)-5-amino-3-methyl-3,6-dihydro-2H-[1,4]oxazin-3-yl)-4-fluoro-phenyl]-amide was obtained. For further purification the product was dissolved in dioxane and hydrochloric acid (4 N, 0.15 ml) was added. After evaporation at reduced pressure the salt was triturated in diethylether (2 ml), the solid material filtrated and dried. The title compound was obtained as a white solid (5 mg, 10% of theory). Mass (calculated) $C_{18}H_{15}ClFN_5O_2$.ClH [424.260]; (found) $[M+H]^+=388$.

Examples 68-72

In a manner analogous to that described in example E1 (method E), the reaction of carboxylic acids with Building blocks I and J, using the 4-(4,6-dimethoxy-1,3,5-triazin-2-yl)-4-methylmorpholinium chloride hydrate (DMTMM) as the condensating agent, followed by the cleavage of the [bis-(4-methoxy-phenyl)-phenyl-methyl]-(DMTr) amino protecting group with acid yielded the following compounds:

Example 68

With 5-chloro-3-fluoro-pyridine-2-carboxylic acid and Building block I, (RS)-[5-(3-amino-phenyl)-5-methyl-5,6-dihydro-2H-[1,4]oxazin-3-yl]-[bis-(4-methoxy-phenyl)-phenyl-methyl]-amine, the 5-chloro-3-fluoro-pyridine-2-carboxylic acid [3-((RS)-5-amino-3-methyl-3,6-dihydro-2H-[1,4]oxazin-3-yl)-4-fluoro-phenyl]-amide hydrochloride (68) (yield: 45% of theory). Mass (calculated) $C_{17}H_{16}ClFN_4O_2$.ClH [399.251]; (found) $[M+H]^+=363$.

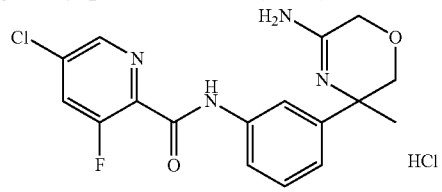

Example 69

With 5-cyano-pyridine-2-carboxylic acid and Building block I, (RS)-[5-(3-amino-phenyl)-5-methyl-5,6-dihydro-2H-[1,4]oxazin-3-yl]-[bis-(4-methoxy-phenyl)-phenyl-methyl]-amine, the 5-cyano-pyridine-2-carboxylic acid [3-((RS)-5-amino-3-methyl-3,6-dihydro-2H-[1,4]oxazin-3-yl)-phenyl]-amide hydrochloride (69) (yield: 5% of theory). Mass (calculated) $C_{18}H_{17}N_5O_2$.ClH [371.826]; (found) $[M+H]^+=363$.

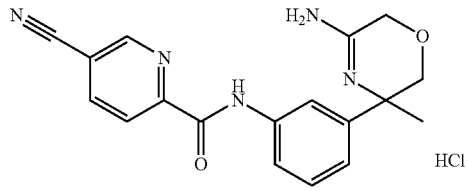

Example 70

With 5-chloro-3-ethyl-pyridine-2-carboxylic acid and Building block J, [(R)-5-(5-amino-2-fluoro-phenyl)-5-methyl-5,6-dihydro-2H-[1,4]oxazin-3-yl]-[bis-(4-methoxy-phenyl)-phenyl-methyl]-amine, the 5-chloro-3-ethyl-pyridine-2-carboxylic acid [3-((R)-5-amino-3-methyl-3,6- dihydro-2H-[1,4]oxazin-3-yl)-4-fluoro-phenyl]-amide hydrochloride (70) as a white solid. Mass (calculated) $C_{19}H_{20}ClFN_4O_2 \cdot ClH$ [427.305]; (found) [M+H]$^+$=391.

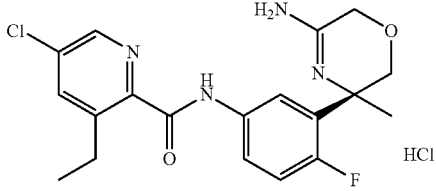

The 5-chloro-3-ethyl-pyridine-2-carboxylic acid was prepared as follows:

In a three necked round bottom flask under a nitrogen atmosphere at −78° C., a solution of n-butyllithium in hexane (1.6 M, 7 ml, 11.1 mmol) was added dropwise to a solution of diisopropylamine (1.56 ml, 11.1 mmol) in tetrahydrofuran (10 ml). The solution was stirred for 30 minutes, then a solution of 5-chloropyridine-2-carboxylic acid (800 mg, 5.0 mmol) in tetrahydrofuran (50 ml) was added dropwise over 1 hour and the reaction was stirred for 1 hour at −78° C. This solution was added dropwise via cannula to a solution of bromoethane (1.89 ml, 25.3 mmol) in tetrahydrofuran (10 ml) at −30° C. The reaction mixture was stirred overnight at room temperature. For the workup, water (10 ml) was added and the mixture was concentrated; hydrochloric acid (1 N) was added to reach pH 5 and the solution obtained was evaporated to dryness. The solid was solubilized in methanol and poured into acetonitrile. The solid formed was filtered off; the solution was collected and evaporated. The crude product was purified by chromatography to give the 5-chloro-3-ethyl-pyridine-2-carboxylic acid (90 mg, 10% of theory) as a white solid. Mass (calculated) $C_8H_8ClNO_2$ [185.611]; (found) [M+H]$^+$=185, [M+2-H]$^+$=187.

Example 71

With (RS)-3-sec-butyl-5-chloro-pyridine-2-carboxylic acid and Building block J, [(R)-5-(5-amino-2-fluoro-phenyl)-5-methyl-5,6-dihydro-2H-[1,4]oxazin-3-yl]-[bis-(4-methoxy-phenyl)-phenyl-methyl]-amine, the 3-((RS)-sec-butyl)-5-chloro-pyridine-2-carboxylic acid [3-((R)-5-amino-3-methyl-3,6-dihydro-2H-[1,4]oxazin-3-yl)-4-fluoro-phenyl]-amide hydrochloride (71) as a white solid. Mass (calculated) $C_{21}H_{24}ClFN_4O_2 \cdot ClH$ [455.358]; (found) [M+H]$^+$=419.

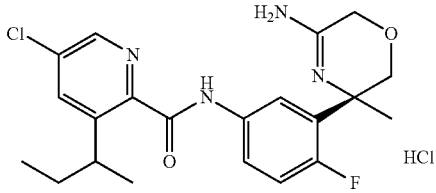

The (RS)-3-sec-butyl-5-chloro-pyridine-2-carboxylic acid was prepared in analogy to the preparation of 5-chloro-3-ethyl-pyridine-2-carboxylic acid by treatment of 5-chloropyridine-2-carboxylic acid with 2-bromo-butane. The (RS)-3-sec-butyl-5-chloro-pyridine-2-carboxylic acid was obtained as a white solid (yield: 6% of theory). Mass (calculated) $C_{10}H_{12}ClNO_2$ [213.66]; (found) [M+H]$^+$=213, [M+2-H]$^+$=215.

Example 72

With 5-cyano-pyridine-2-carboxylic acid and Building block J, [(R)-5-(5-amino-2-fluoro-phenyl)-5-methyl-5,6-dihydro-2H-[1,4]oxazin-3-yl]-[bis-(4-methoxy-phenyl)-phenyl-methyl]-amine, the 5-cyano-pyridine-2-carboxylic acid [3-((R)-5-amino-3-methyl-3,6-dihydro-2H-[1,4]oxazin-3-yl)-4-fluoro-phenyl]-amide hydrochloride (72) (yield: 59% of theory). Mass (calculated) $C_{18}H_{16}FN_5O_2 \cdot ClH$ [389.816]; (found) [M+H]$^+$=354.

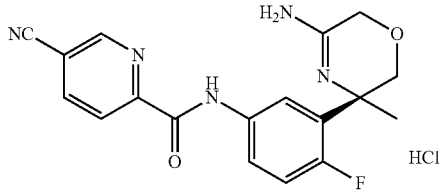

Example 73

With 5-difluoromethoxy-pyridine-2-carboxylic acid (CAS 117323-34-2) and Building block J, [(R)-5-(5-amino-2-fluoro-phenyl)-5-methyl-5,6-dihydro-2H-[1,4]oxazin-3-yl]-[bis-(4-methoxy-phenyl)-phenyl-methyl]-amine, the 5-difluoromethoxy-pyridine-2-carboxylic acid [3-((R)-5-amino-3-methyl-3,6-dihydro-2H-[1,4]oxazin-3-yl)-4-fluoro-phenyl]-amide hydrochloride (73) (yield: 41% of theory). Mass (calculated) $C_{18}H_{17}F_3N_4O_3 \cdot ClH$ [430.812]; (found) [M+H]$^+$=395.

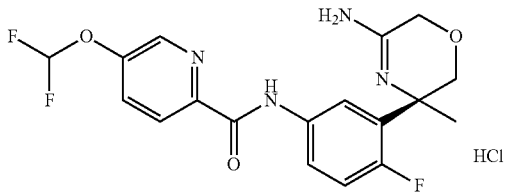

Example 74

5-Chloro-3-fluoro-pyridine-2-carboxylic acid [3-((R)-5-amino-3-methyl-3,6-dihydro-2H-[1,4]oxazin-3-yl)-4-fluoro-phenyl]-amide hydrochloride

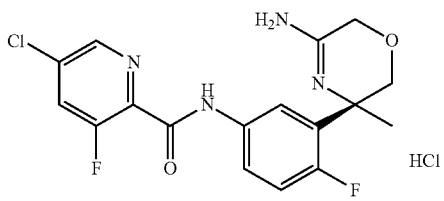

In analogy to example 22 a) the reaction of 5-chloro-3-fluoro-pyridine-2-carboxylic acid and Building block J, [(R)-5-(5-amino-2-fluoro-phenyl)-5-methyl-5,6-dihydro-2H-[1,4]oxazin-3-yl]-[bis-(4-methoxy-phenyl)-phenyl-methyl]-amine, using O-(7-azabenzotriazol-1-yl)-N,N,N',N'-tetramethyluronium hexafluorophosphate as the condensating agent in presence of Huenig's base, followed by the cleavage of the [bis-(4-methoxy-phenyl)-phenyl-methyl]-(DMTr) amino protecting group with trifluoroacetic acid in dichloromethane yielded the title compound (yield:

Example 75

5-Furan-2-yl-isoxazole-3-carboxylic acid [3-((RS)-5-amino-3-methyl-3,6-dihydro-2H-[1,4]oxazin-3-yl)-4-fluoro-phenyl]-amide

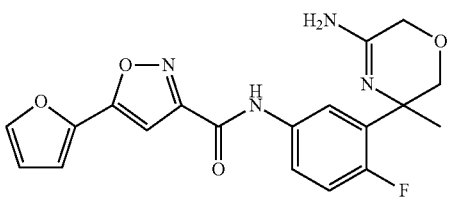

A solution of 5-furan-2-yl-isoxazole-3-carboxylic acid (CAS 98434-06-1) (77.3 mg, 0.42 mmol) in methanol (2 ml) was cooled to 0° C. 4-(4,6-Dimethoxy-1,3,5-triazin-2-yl)-4-methylmorpholinium chloride hydrate (DMTMM) (135 mg, 0.46 mmol) was added and the mixture stirred at 0° C. for 10 minutes. Thereafter, a solution of (RS)-5-(5-amino-2-fluoro-phenyl)-5-methyl-5,6-dihydro-2H-[1,4]oxazin-3-ylamine (85 mg, 0.38 mmol) in methanol (1 ml) was added and the reaction mixture stirred at 0° C. for 2 hours, then kept at 4° C. for 16 hours. For the workup, the reaction mixture was treated at 0° C. with sodium hydroxide (1 N, 6 ml). The yellow suspension was extracted with ethyl acetate (15 ml), then the aqueous layer re-extracted with ethyl acetate (10 ml). The combined organic layers were dried over sodium sulfate and evaporated at reduced pressure. After chromatography on a Silicycle-Si-amine phase using a gradient of dichloromethane and methanol=100/0 to 90/10 the 5-furan-2-yl-isoxazole-3-carboxylic acid [3-((RS)-5-amino-3-methyl-3,6-dihydro-2H-[1,4]oxazin-3-yl)-4-fluoro-phenyl]-amide was obtained as a white sold (16 mg, 11% of theory). Mass (calculated) $C_{19}H_{17}FN_4O_4$ [384.365]; (found) $[M+H]^+$=385.

Examples 76-78

In a manner analogous to that described in example E1 (method E), the condensation of carboxylic acids with Building block P, (RS)-5-(5-amino-2-fluoro-phenyl)-5-methyl-5,6-dihydro-2H-[1,4]oxazin-3-ylamine, yielded the following compounds:

Example 76

With 5-furan-2-yl-pyridine-2-carboxylic acid (CAS 930110-99-9) the 5-furan-2-yl-pyridine-2-carboxylic acid [3-((RS)-5-amino-3-methyl-3,6-dihydro-2H-[1,4]oxazin-3-yl)-4-fluoro-phenyl]-amide (76) as a light yellow solid. Mass (calculated) $C_{21}H_{19}FN_4O_3$ [394.404]; (found) $[M+H]^+$=395.

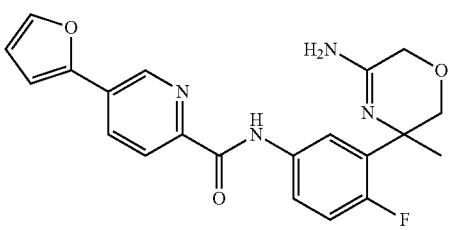

Example 77

With 5-pyrrolidin-1-yl-pyridine-2-carboxylic acid (CAS 950603-19-7) the 5-pyrrolidin-1-yl-pyridine-2-carboxylic acid [3-((RS)-5-amino-3-methyl-3,6-dihydro-2H-[1,4]oxazin-3-yl)-4-fluoro-phenyl]-amide (77) as a white solid. Mass (calculated) $C_{21}H_{24}FN_5O_2$ [397.452]; (found) $[M+H]^+$= 398.

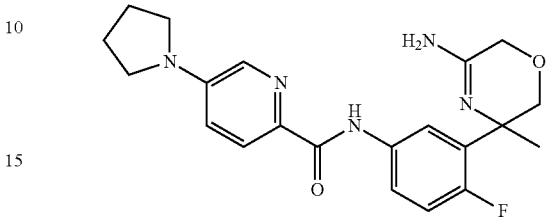

Example 78

With 5-thiophen-2-yl-isoxazole-3-carboxylic acid (CAS 763109-71-3) the 5-thiophen-2-yl-isoxazole-3-carboxylic acid [3-((RS)-5-amino-3-methyl-3,6-dihydro-2H-[1,4]oxazin-3-yl)-4-fluoro-phenyl]-amide (78) as a white solid. Mass (calculated) $C_{21}H_{24}FN_5O_2$ [397.452]; (found) $[M+H]^+$= 398.

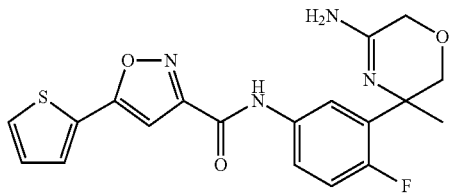

Example 79

(RS)-N-[3-(5-Amino-3-methyl-3,6-dihydro-2H-[1,4]oxazin-3-yl)-4-fluoro-phenyl]-3,3,3-trifluoro-propionamide In a manner analogous to that described in example E1 (method E), the condensation of 3,3,3-trifluoro-propionic acid with Building block P, (RS)-5-(5-amino-2-fluoro-phenyl)-5-methyl-5,6-dihydro-2H-[1,4]oxazin-3-ylamine, yielded the title compound as a yellow oil. Mass (calculated) $C_{14}H_{15}F_4N_3O_2$ [33.283]; (found) $[M+H]^+$=334.

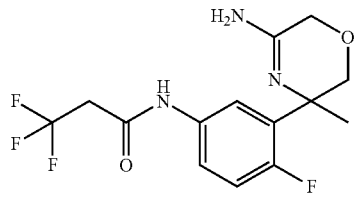

Examples 80-82

In a manner analogous to that described in example E1 (method E), the condensation of carboxylic acids with Building block Q, (R)-5-(5-amino-2-fluoro-phenyl)-5-methyl-5,6-dihydro-2H-[1,4]oxazin-3-ylamine, yielded the following compounds:

Example 80

With oxazole-2-carboxylic acid the oxazole-2-carboxylic acid [3-((R)-5-amino-3-methyl-3,6-dihydro-2H-[1,4]oxazin-3-yl)-4-fluoro-phenyl]-amide (80) as a white solid. Mass (calculated) $C_{15}H_{15}FN_4O_3$ [318.306]; (found) [M+H]$^+$= 319.

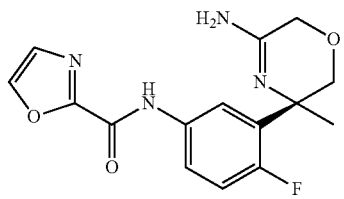

Example 81

With 5-trifluoromethyl-pyrazine-2-carboxylic acid the 5-trifluoromethyl-pyrazine-2-carboxylic acid [3-((R)-5-amino-3-methyl-3,6-dihydro-2H-[1,4]oxazin-3-yl)-4-fluoro-phenyl]-amide formate (81) as a white solid. Mass (calculated) $C_{17}H_{15}F_4N_5O_2.CH_2O_2$ [443.350]; (found) [M+H]$^+$=398.

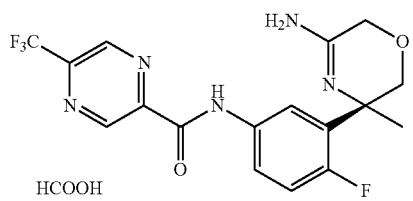

Example 82

With 5-trifluoromethyl-pyrimidine-2-carboxylic acid the 5-trifluoromethyl-pyrazine-2-carboxylic acid [3-((R)-5-amino-3-methyl-3,6-dihydro-2H-[1,4]oxazin-3-yl)-4-fluoro-phenyl]-amide formate (82) as a white solid. Mass (calculated) $C_{17}H_{15}F_4N_5O_2.CH_2O_2$ [443.350]; (found) [M+H]$^+$=398.

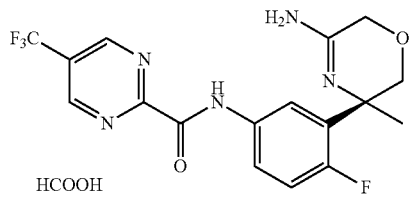

Examples 83-97

In a manner analogous to that described in example E1 (method E), the condensation of carboxylic acids with Building block Q, (R)-5-(5-amino-2-fluoro-phenyl)-5-methyl-5,6-dihydro-2H-[1,4]oxazin-3-ylamine, yielded the compounds below. These compounds were purified by preparative HPLC using a gradient of water and methanol (plus 0.05% formic acid)=95/5 to 0/100 as the eluent.

Example 83

With 2,2,3,3-tetrafluoro-propionic acid the N-[3-((R)-5-amino-3-methyl-3,6-dihydro-2H-[1,4]oxazin-3-yl)-4-fluoro-phenyl]-2,2,3,3-tetrafluoro-propionamide formate (83) as a colorless amorphous material. Mass (calculated) $C_{14}H_{14}F_5N_3O_2.CH_2O_2$ [397.300]; (found) [M+H]$^+$=352.

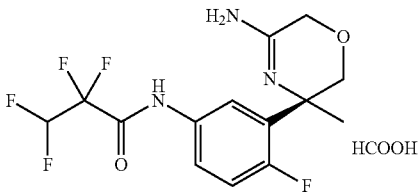

Example 84

With methoxy-acetic acid the N-[3-((R)-5-amino-3-methyl-3,6-dihydro-2H-[1,4]oxazin-3-yl)-4-fluoro-phenyl]-2-methoxy-acetamide formate (84) as a white amorphous material. Mass (calculated) $C_{14}H_{18}FN_3O_3.CH_2O_2$ [341.330]; (found) [M+H]$^+$=296.

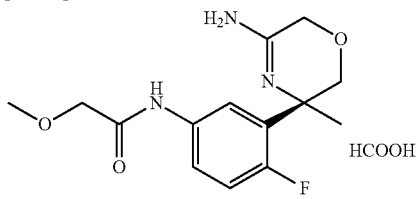

Example 85

With (RS)-3,3,3-trifluoro-2-[(RS)-1-(tetrahydro-furan-2-yl)methyl]-propionic acid the (RS)-N-[3-((R)-5-amino-3-methyl-3,6-dihydro-2H-[1,4]oxazin-3-yl)-4-fluoro-phenyl]-3,3,3-trifluoro-2-[(RS)-1-(tetrahydro-furan-2-yl)methyl]-propionamide formate (85) as a white amorphous material. Mass (calculated) $C_{19}H_{23}F_4N_3O_3.CH_2O_2$ [463.420]; (found) [M+H]$^+$=418.

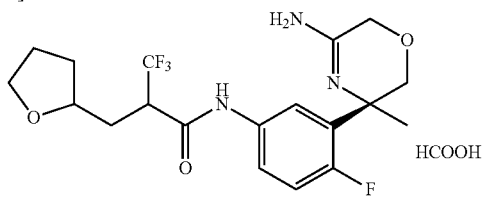

Example 86

With 1-methoxymethyl-cyclopropanecarboxylic acid the 1-methoxymethyl-cyclopropanecarboxylic acid [3-((R)-5-amino-3-methyl-3,6-dihydro-2H-[1,4]oxazin-3-yl)-4-fluoro-phenyl]-amide formate (86) as a white amorphous material. Mass (calculated) $C_{17}H_{22}FN_3O_3.CH_2O_2$ [381.400]; (found) [M+H]$^+$=336.

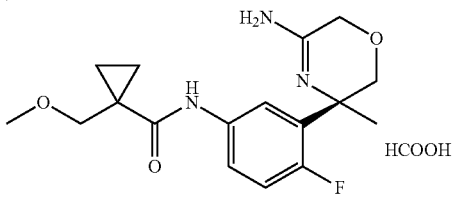

Example 87

With (RS)-2-fluoro-propionic acid the (RS)-N-[3-((R)-5-amino-3-methyl-3,6-dihydro-2H-[1,4]oxazin-3-yl)-4-fluoro-phenyl]-2-fluoro-propionamide formate (87) as a white amorphous material. Mass (calculated) $C_{14}H_{17}F_2N_3O_2 \cdot CH_2O_2$ [343.328]; (found) $[M+H]^+=298$.

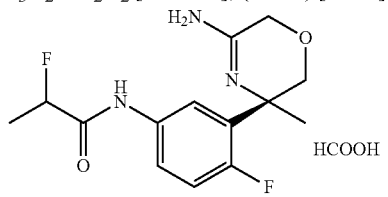

Example 88

With isobutyric acid the N-[3-((R)-5-amino-3-methyl-3,6-dihydro-2H-[1,4]oxazin-3-yl)-4-fluoro-phenyl]-isobutyramide formate (88) as a white amorphous material. Mass (calculated) $C_{15}H_{20}FN_3O_2 \cdot CH_2O_2$ [339.360]; (found) $[M+H]^+=294$.

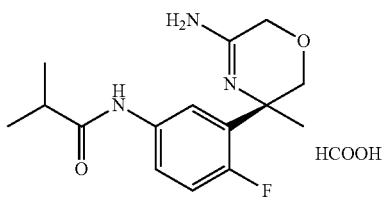

Example 89

With (RS)-2,3,3,3-tetrafluoro-propionic acid the (RS)-N-[3-((R)-5-amino-3-methyl-3,6-dihydro-2H-[1,4]oxazin-3-yl)-4-fluoro-phenyl]-2-fluoro-propionamide formate (89) as a white amorphous material. Mass (calculated) $C_{14}H_{14}F_5N_3O_2 \cdot CH_2O_2$ [397.298]; (found) $[M+H]^+=352$.

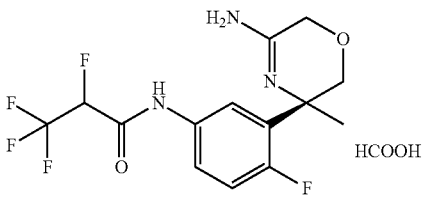

Example 90

With 2,2-difluoro-propionic acid the N-[3-((R)-5-amino-3-methyl-3,6-dihydro-2H-[1,4]oxazin-3-yl)-4-fluoro-phenyl]-2,2-difluoro-propionamide formate (90) as a white amorphous material. Mass (calculated) $C_{14}H_{16}F_3N_3O_2 \cdot CH_2O_2$ [361.320]; (found) $[M+H]^+=316$.

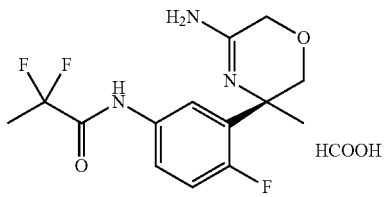

Example 91

With difluoro-acetic acid the N-[3-((R)-5-amino-3-methyl-3,6-dihydro-2H-[1,4]oxazin-3-yl)-4-fluoro-phenyl]-2,2-difluoro-acetamide formate (91) as a white foam. Mass (calculated) $C_{13}H_{14}F_3N_3O_2 \cdot CH_2O_2$ [347.290]; (found) $[M+H]^+=302$.

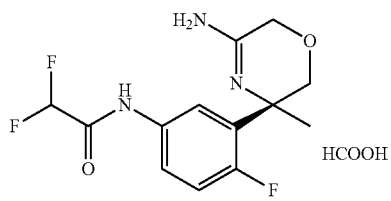

Example 92

With 2-fluoro-2-methyl-propionic acid the N-[3-((R)-5-amino-3-methyl-3,6-dihydro-2H-[1,4]oxazin-3-yl)-4-fluoro-phenyl]-2-fluoro-2-methyl-propionamide formate (92) as a white amorphous material. Mass (calculated) $C_{15}H_{19}F_2N_3O_2 \cdot CH_2O_2$ [357.350]; (found) $[M+H]^+=312$.

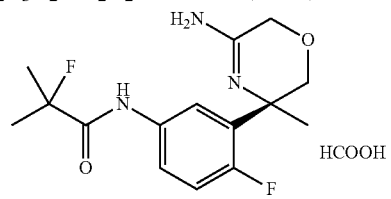

Example 93

With acetic acid the N-[3-((R)-5-amino-3-methyl-3,6-dihydro-2H-[1,4]oxazin-3-yl)-4-fluoro-phenyl]-acetamide formate (93) as a white amorphous material. Mass (calculated) $C_{13}H_{16}FN_3O_2 \cdot CH_2O_2$ [311.310]; (found) $[M+H]^+=266$.

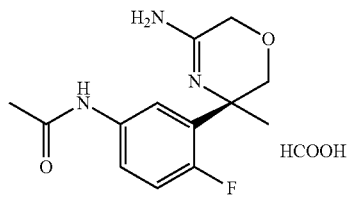

Example 94

With propionic acid the N-[3-((R)-5-amino-3-methyl-3,6-dihydro-2H-[1,4]oxazin-3-yl)-4-fluoro-phenyl]-propionamide formate (94) as a white amorphous material. Mass (calculated) $C_{14}H_{18}FN_3O_2 \cdot CH_2O_2$ [325.340]; (found) $[M+H]^+=280$.

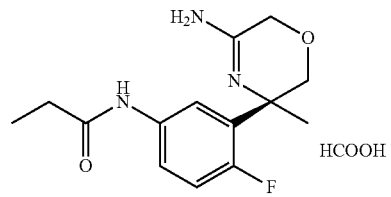

Example 95

With 3-methyl-butyric acid the N-[3-((R)-5-amino-3-methyl-3,6-dihydro-2H-[1,4]oxazin-3-yl)-4-fluoro-phenyl]-3-methyl-butyramide formate (95) as a white amorphous material. Mass (calculated) $C_{16}H_{22}FN_3O_2 \cdot CH_2O_2$ [353.390]; (found) $[M+H]^+=308$.

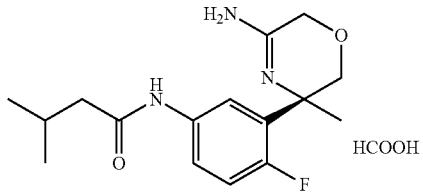

Example 96

With (RS)-tetrahydro-furan-3-carboxylic acid the (RS)-tetrahydro-furan-3-carboxylic acid [3-((R)-5-amino-3-methyl-3,6-dihydro-2H-[1,4]oxazin-3-yl)-4-fluoro-phenyl]-amide formate (96) as a white amorphous material. Mass (calculated) $C_{16}H_{20}FN_3O_3 \cdot CH_2O_2$ [367.375]; (found) $[M+H]^+=322$.

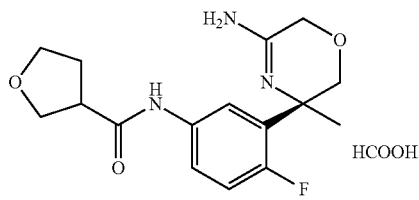

Example 97

With formic acid the N-[3-((R)-5-Amino-3-methyl-3,6-dihydro-2H-[1,4]oxazin-3-yl)-4-fluoro-phenyl]-formamide formate (97) as a white amorphous material. Mass (calculated) $C_{12}H_{14}FN_3O_2 \cdot CH_2O_2$ [297.280]; (found) $[M+H]^+=252$.

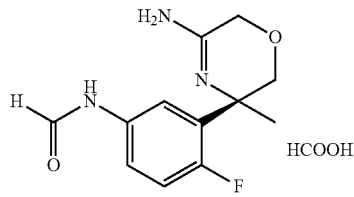

Examples 98-99

Method F

In a manner analogous to that described in example E1 (method E), the reaction of carboxylic acids with Building block H, (R)-5-(5-amino-2-fluoro-phenyl)-5-methyl-morpholine-3-thione, using the 4-(4,6-dimethoxy-1,3,5-triazin-2-yl)-4-methylmorpholinium chloride hydrate (DMTMM) as the condensating agent, followed by the treatment of the resulting thiones with a mixture of ammonia in water and tent-butyl hydroperoxide as described in example 22, yielded the following compounds:

Example 98

With 5-chloro-3-methyl-pyridine-2-carboxylic acid the 5-chloro-3-methyl-pyridine-2-carboxylic acid [3-((R)-5-amino-3-methyl-3,6-dihydro-2H-[1,4]oxazin-3-yl)-4-fluoro-phenyl]-amide (98) as a white foam. Mass (calculated) $C_{18}H_{18}ClFN_4O_2$ [376.817]; (found) $[M+H]^+=377$.

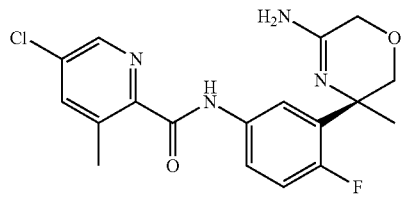

Example 99

With 5-fluoro-pyridine-2-carboxylic acid the 5-fluoro-pyridine-2-carboxylic acid [3-((R)-5-amino-3-methyl-3,6-dihydro-2H-[1,4]oxazin-3-yl)-4-fluoro-phenyl]-amide (99) as a white foam. Mass (calculated) $C_{17}H_{16}F_2N_4O_2$ [346.335]; (found) $[M+H]^+=347$.

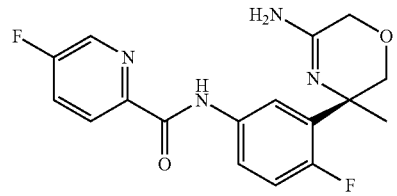

The invention claimed is:
1. A compound of formula I,

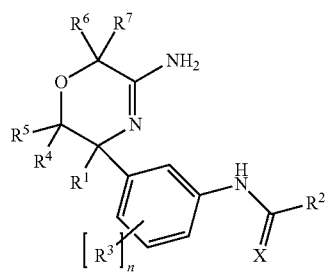

wherein
X is O or S,
$R^1$ is selected from the group consisting of
  i) lower alkyl,
  ii) lower alkyl substituted by 1-5 substituents individually selected from cycloalkyl, halogen, halogen-lower alkoxy and lower alkoxy, and
  iii) cycloalkyl,
$R^2$ is selected from the group consisting of
  i) H,
  ii) lower alkyl, and
  iii) lower alkyl substituted by 1-5 substituents individually selected from cycloalkyl, halogen, halogen-lower alkoxy, heterocyclyl and lower alkoxy,
$R^3$ is individually selected from the group consisting of
  i) halogen and
  ii) lower alkyl, R⁴ is individually selected from the group consisting of
  i) H and
  ii) lower alkyl,
R⁵ is individually selected from the group consisting of
  i) H and
  ii) lower alkyl,
R⁶ is individually selected from the group consisting of
  i) H and
  ii) lower alkyl,
R⁷ is individually selected from the group consisting of
  i) H,
  ii) aryl, and
  iii) lower alkyl, and
n is 0, 1 or 2,
or a pharmaceutically acceptable salt thereof.

2. A compound of claim 1, wherein
X is O or S,
R¹ is selected from the group consisting of
  i) lower alky, and
  ii) cycloalkyl,
R² is selected from the group consisting of
  i) H, and
  ii) lower alkyl substituted by 1-5 substituents individually selected from cycloalkyl, halogen, heterocyclyl and lower alkoxy,
R³ is halogen,
R⁴ is H or lower alkyl,
R⁵ is H or lower alkyl,
R⁶ is H or lower alkyl,
R⁷ is H, aryl or lower alkyl, and
n is 0 or 1
or a pharmaceutically acceptable salt thereof.

3. A compound of formula Ix according to claim 1, wherein

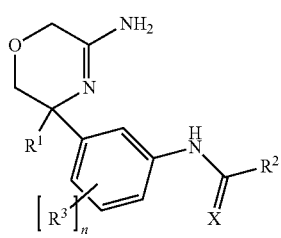

Ix wherein
X is O or S,
R¹ is selected from the group consisting of
  i) lower alkyl,
  ii) lower alkyl substituted by 1-5 substituents individually selected from cycloalkyl, halogen, halogen-lower alkoxy and lower alkoxy, and
  iii) cycloalkyl,
R² is selected from the group consisting of
  lower alkyl substituted by 1-5 halogen,
R³ is individually selected from the group consisting of
  i) halogen and
  ii) lower alkyl, and
n is 0, 1 or 2,
or a pharmaceutically acceptable salt thereof.

4. A compound of claim 1, wherein X is O.

5. A compound of claim 1, wherein R¹ is lower alkyl or cycloalkyl.

6. A compound of claim 5, wherein R¹ is methyl or cyclopropyl.

7. A compound of claim 1, wherein R² is selected from the group
  consisting of
  i) H, and
  ii) lower alkyl substituted by 1-5 substituents individually selected from cycloalkyl, halogen, heterocyclyl and lower alkoxy.

8. A compound of claim 1, wherein R² is lower alkyl substituted by 1-5 halogens.

9. A compound of claim 1, wherein R² is 1,1,1,2-tetrafluoro-ethyl, 1,1,2,2,2-pentafluoro-ethyl, 1,1,2,2-tetrafluoro-ethyl, 2,2,2-trifluoroethyl, 2,2-difluoro-ethyl, 2-fluoro-ethyl, difluoro-methyl, ethyl, fluoro-isopropyl, H, isopropyl, methyl, or methoxy-methyl.

10. A compound of claim 1, wherein n is 1.

11. A compound of claim 1, wherein R³ is halogen.

12. A compound of claim 11, wherein R³ is F.

13. A compound of claim 1, wherein n is 0.

14. A compound of claim 1, which is,
  (RS)—N-[3-(5-Amino-3-methyl-3,6-dihydro-2H-[1,4]oxazin-3-yl)-4-fluoro-phenyl]-2,2,3,3,3-pentafluoro-propionamide,
  or a pharmaceutically acceptable salt thereof.

15. A compound of claim 1, which is
  (RS)—N-[3-(5-Amino-3-methyl-3,6-dihydro-2H-[1,4]oxazin-3-yl)-4-fluoro-phenyl]-3,3,3-trifluoro-propionamide,
  or a pharmaceutically acceptable salt thereof.

16. A compound of claim 1, selected from the group consisting of
  N-[3-((R)-5-Amino-3-methyl-3,6-dihydro-2H-[1,4]oxazin-3-yl)-4-fluoro-phenyl]-2,2,3,3-tetrafluoro-propionamide,
  N-[3-((R)-5-Amino-3-methyl-3,6-dihydro-2H-[1,4]oxazin-3-yl)-4-fluoro-phenyl]-2-methoxy-acetamide,
  (RS)—N-[3-((R)-5-Amino-3-methyl-3,6-dihydro-2H-[1,4]oxazin-3-yl)-4-fluoro-phenyl]-3,3,3-trifluoro-2-[(RS)-1-(tetrahydro-furan-2-yl)methyl]-propionamide,
  N-[3-((R)-5-Amino-3-methyl-3,6-dihydro-2H-[1,4]oxazin-3-yl)-4-fluoro-phenyl]-isobutyramide,
  (RS)—N-[3-((R)-5-Amino-3-methyl-3,6-dihydro-2H-[1,4]oxazin-3-yl)-4-fluoro-phenyl]-2-fluoro-propionamide, and
  N-[3-((R)-5-Amino-3-methyl-3,6-dihydro-2H-[1,4]oxazin-3-yl)-4-fluoro-phenyl]-2,2-difluoro-propionamide
  or a pharmaceutically acceptable salt thereof.

17. A compound of claim 1, selected from the group consisting of
  N-[3-((R)-5-Amino-3-methyl-3,6-dihydro-2H-[1,4]oxazin-3-yl)-4-fluoro-phenyl]-2,2-difluoro-acetamide,
  (R)—N-(3-(5-Amino-3-methyl-3,6-dihydro-2H-1,4-oxazin-3-yl)-4-fluorophenyl)-2-fluoro-2-methylpropanamide,
  N-[3-((R)-5-Amino-3-methyl-3,6-dihydro-2H-[1,4]oxazin-3-yl)-4-fluoro-phenyl]-acetamide,
  N-[3-((R)-5-Amino-3-methyl-3,6-dihydro-2H-[1,4]oxazin-3-yl)-4-fluoro-phenyl]-propionamide,
  N-[3-((R)-5-Amino-3-methyl-3,6-dihydro-2H-[1,4]oxazin-3-yl)-4-fluoro-phenyl]-3-methyl-butyramide, and
  N-[3-((R)-5-Amino-3-methyl-3,6-dihydro-2H-[1,4]oxazin-3-yl)-4-fluoro-phenyl]-formamide,
  or a pharmaceutically acceptable salt thereof.

18. A compound of claim 1, which is
  N-[3-(5-Amino-3-methyl-3,6-dihydro-2H-[1,4]oxazin-3-yl)-4-fluoro-phenyl]-2,2,3,3,3-pentafluoro-propionamide, and
  or a pharmaceutically acceptable salt thereof.

19. A pharmaceutical composition comprising a therapeutically effective amount of a compound of formula I

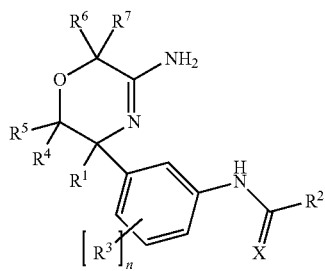

wherein
X is O or S,
R$^1$ is selected from the group consisting of
  i) lower alkyl,
  ii) lower alkyl substituted by 1-5 substituents individually selected from cycloalkyl, halogen, halogen-lower alkoxy and lower alkoxy, and
  iii) cycloalkyl,
R$^2$ is selected from the group consisting of
  i) H,
  ii) lower alkyl, and
  iii) lower alkyl substituted by 1-5 substituents individually selected from cycloalkyl, halogen, halogen-lower alkoxy, heterocyclyl and lower alkoxy,
R$^3$ is individually selected from the group consisting of
  i) halogen and
  ii) lower alkyl,
R$^4$ is individually selected from the group consisting of
  i) H and
  ii) lower alkyl,
R$^5$ is individually selected from the group consisting of
  i) H and
  ii) lower alkyl,
R$^6$ is individually selected from the group consisting of
  i) H and
  ii) lower alkyl,
R$^7$ is individually selected from the group consisting of
  i) H,
  ii) aryl, and
  iii) lower alkyl, and
n is 0, 1 or 2,
or a pharmaceutically acceptable salt thereof and a pharmaceutically acceptable carrier.

* * * * *

UNITED STATES PATENT AND TRADEMARK OFFICE
CERTIFICATE OF CORRECTION

PATENT NO. : 8,188,079 B2  
APPLICATION NO. : 12/852538  
DATED : May 29, 2012  
INVENTOR(S) : Andreini et al.

Page 1 of 1

It is certified that error appears in the above-identified patent and that said Letters Patent is hereby corrected as shown below:

TITLE PAGE:

Item 75:
• Inventor information: "Emanuele Gabellieri, Siena (IT)" should be added to the list of inventors.

• Assignee information reads: "(73) Assignee Hoffman-La Roche Inc., Nutley, NJ (US); Siena Biotech S.p.A., Siena (IT)". The Assignee information should read -- (73) Assignee Hoffmann-La Roche Inc., Nutley, NJ (US); Siena Biotech S.p.A., Siena (IT) --.

Signed and Sealed this

Seventeenth Day of July, 2012

David J. Kappos
*Director of the United States Patent and Trademark Office*